US010899801B2

(12) United States Patent
Meyers et al.

(10) Patent No.: US 10,899,801 B2
(45) Date of Patent: Jan. 26, 2021

(54) PRODUCTION OF SOLUBLE HIV ENVELOPE TRIMERS IN PLANTA

(71) Applicant: University of Cape Town, Cape Town (ZA)

(72) Inventors: Ann Elizabeth Meyers, Cape Town (ZA); Anna-Lise Williamson, Cape Town (ZA); Edward Peter Rybicki, Cape Town (ZA); Emmanuel Aubrey Margolin, Cape Town (ZA); Rosamund Chapman, Cape Town (ZA)

(73) Assignee: University of Cape Town, Cape Town (ZA)

( * ) Notice: Subject to any disclaimer, the term of this patent is extended or adjusted under 35 U.S.C. 154(b) by 0 days.

(21) Appl. No.: 16/382,933

(22) PCT Filed: Oct. 13, 2017

(86) PCT No.: PCT/IB2017/056349
§ 371 (c)(1),
(2) Date: Apr. 12, 2019

(87) PCT Pub. No.: WO2018/069878
PCT Pub. Date: Apr. 19, 2018

(65) Prior Publication Data
US 2019/0337994 A1 Nov. 7, 2019

(30) Foreign Application Priority Data
Oct. 14, 2016 (GB) .................................. 1617480.7

(51) Int. Cl.
| | | |
|---|---|---|
| *A61K 39/00* | (2006.01) | |
| *A61K 45/06* | (2006.01) | |
| *C07K 16/10* | (2006.01) | |
| *G01N 33/569* | (2006.01) | |
| *A61K 39/42* | (2006.01) | |
| *C07K 14/16* | (2006.01) | |
| *A61K 39/21* | (2006.01) | |
| *C12N 15/82* | (2006.01) | |

(52) U.S. Cl.
CPC ............ *C07K 14/162* (2013.01); *A61K 39/21* (2013.01); *C12N 15/8257* (2013.01); *C12N 2740/16051* (2013.01); *C12N 2740/16122* (2013.01); *C12N 2740/16134* (2013.01)

(58) Field of Classification Search
CPC ... A61P 31/18; C07K 14/005; C07K 2317/76; A61K 2039/505; A61K 45/06
See application file for complete search history.

(56) References Cited

U.S. PATENT DOCUMENTS

| | | | |
|---|---|---|---|
| 10,058,604 B2 * | 8/2018 | Wyatt | ................. C07K 14/005 |
| 2004/0040061 A1 | 2/2004 | Horn et al. | |
| 2012/0121635 A1 | 5/2012 | Horn et al. | |
| 2013/0344100 A1 | 12/2013 | D'Aoust et al. | |
| 2017/0035877 A1 | 9/2017 | Wyatt et al. | |

OTHER PUBLICATIONS

Ringe R. P., et al., "Influences on the Design and Purification of Soluble, Recombinant Native-Like HIV-1 Envelope Glycoprotein Trimers", Journal of Virology, Aug. 26, 2015, vol. 89, No. 23, pp. 12189-12210, American Society for Microbiology.
Margolin E., et al., "Development of a Plant-based Expression System for the Production of Soluble HIV-1 Subtype C Envelope Antigens", AIDS Research and Human Retroviruses, Oct. 17, 2016, p. 327, & HIVR4P, pp. 17-21, Oct. 2016, Chicago, Retrieved from the Internet: URL:http://online.liebertpub.com/doi/pdfplus/10.1089/aid.2016.5000.abstracts.
Margolin E. A., et al., "An Investigation into Improved HIV-1 Subtype C Envelope Based Vaccine Design", Dissertation, University of Cape Town, ZA, Feb. 1, 2014, Retrieved from the Internet: URL:http://open.uct.ac.za/bitstream/item/5967/thesis_hsf_2014_margolin_ea.pdf?sequence+1, Abstract; Chapter 3 & 4.
Rosenberg Y., et al., "Rapid High-Level Production of Functional HIV Broadly Neutralizing Monoclonal Antibodies in Transient Plant Expression Systems", PLOS ONE, Mar. 22, 2013, vol. 8, No. 3, p. e58724.

* cited by examiner

*Primary Examiner* — Barry A Chestnut
(74) *Attorney, Agent, or Firm* — Womble Bond Dickinson (US) LLP; Cristin Cowles; Soo Kim

(57) ABSTRACT

The present invention relates to a method for producing a recombinant HIV glycoprotein polypeptide in a plant and to trimeric complexes of the recombinant, plant-produced HIV glycoprotein polypeptide which mimic the native HIV Env complex. The invention also relates to nucleic acids encoding the recombinant polypeptides, expression vectors containing the aforementioned nucleic acids and to pharmaceutical compositions, uses and methods of eliciting an immune response against HIV in a subject using the recombinant polypeptides and trimeric complexes.

20 Claims, 10 Drawing Sheets
Specification includes a Sequence Listing.

```
1    MEWSWIFLFL LSGTAGVHSS GGLWVTVYYG VPVWREAKTT LFCASDAKSY EKEVHNVWAT
61   HACVPTDPNP QELVLKNVTE NFNMWKNDMV DQMHEDIISL WDQSLKPCVK LTPLCVTLNC
121  SDAKVNINAT YNGTREEIKN CSFNATTELR DKKKKEYALF YRLDIVPLNK EGNNNSEYRL
181  INCNTSVITQ ACPKVTFDPI PIHYCAPAGY AILKCNNKTF NGTGPCNNVS TVQCTHGIKP
241  VVSTQLLLNG SLAEEEIIIR SENLTDNVKT IIVHLNESVE INCTRPNNNT RKSIRIGPGQ
301  TFYATGDIIG DIRQAHCNIS EIKWEKTLQR VSEKLREHFN KTIIFNQSSG GDLEITTHSF
361  NCGGEFFYCN TSDLFFNKTF DETYSTGSNS TNSTITLPCR IKQIINMWQE VGRAMYASPI
421  AGEITCKSNI TGLLLTRDGG GNNSTEETFR PGGGNMRDNW RSELYKYKVV EVKPLGIAPT
481  EARRRVVQQG GGGSGGGGSA VVGLGAVFLG FLGTAGSTMG AASITLTVQA RQLLSGIVQQ
541  QSNLLRAPEA QQHMLQLTVW GIKQLQARVL AIERYLKDQQ LLGMWGCSGK LICTTNVYWN
601  SSWSNKTYNE IWDNMTWMQW DREIDNYTDT IYKLLEVSQK QQESNEKDLL ALDSWNNLWN
661  WFDISKWLWY IQILSIYSTV ASSLALAIMV AGLSLWMCSN GSLQCRAAA*
```

Figure 10

```
1    MEWSWIFLFL LSGTAGVHSS GGLWVTVYYG VPVWREAKTT LFCASDAKSY EKEVHNVWAT
61   HACVPTDPNP QELVLKNVTE NFNMWKNDMV DQMHEDIISL WDQSLKPCVK LTPLCVTLNC
121  SDAKVNINAT YNGTREEIKN CSFNATTELR DKKKKEYALF YRLDIVPLNK EGNNNSEYRL
181  INCNTSVITQ ACPKVTFDPI PIHYCAPAGY AILKCNNKTF NGTGPCNNVS TVQCTHGIKP
241  VVSTQLLLNG SLAEEEIIIR SENLTDNVKT IIVHLNESVE INCTRPNNNT RKSIRIGPGQ
301  TFYATGDIIG DIRQAHCNIS EIKWEKTLQR VSEKLREHFN KTIIFNQSSG GDLEITTHSF
361  NCGGEFFYCN TSDLFFNKTF DETYSTGSNS TNSTITLPCR IKQIINMWQE VGRAMYASPI
421  AGEITCKSNI TGLLLTRDGG GNNSTEETFR PGGGNMRDNW RSELYKYKVV EVKPLGIAPT
481  EARRRVVQQG GGGSGGGGSE GGWQGMVDGW YGYHHSNEQG SGYAADKEST QKAIDGVTNK
541  VNSIIDKMNT QFEAVGREFN NLERRIENLN KKMEDGFLDV WTYNAELLVL MENERTLDFH
601  DSNVKNLYDK VRLQLRDNAK ELGNGCFEFY HKCDNECMES VRNGTYDYPQ YSEEARLKRE
661  EISGVKLESI GIYQILSIYS TVASSLALAI MVAGLSLWMC SNGSLQCRAA A*
```

Figure 11

```
1    MEWSWIFLFL LSGTAGVHSS GGLWVTVYYG VPVWREAKTT LFCASDAKSY EKEVHNVWAT
61   HACVPTDPNP QELVLKNVTE NFNMWKNDMV DQMHEDIISL WDQSLKPCVK LTPLCVTLNC
121  SDAKVNINAT YNGTREEIKN CSFNATTELR DKKKKEYALF YRLDIVPLNK EGNNNSEYRL
181  INCNTSVITQ ACPKVTFDPI PIHYCAPAGY AILKCNNKTF NGTGPCNNVS TVQCTHGIKP
241  VVSTQLLLNG SLAEEEIIIR SENLTDNVKT IIVHLNESVE INCTRPNNNT RKSIRIGPGQ
301  TFYATGDIIG DIRQAHCNIS EIKWEKTLQR VSEKLREHFN KTIIFNQSSG GDLEITTHSF
361  NCGGEFFYCN TSDLFFNKTF DETYSTGSNS TNSTITLPCR IKQIINMWQE VGRAMYASPI
421  AGEITCKSNI TGLLLTRDGG GNNSTEETFR PGGGNMRDNW RSELYKYKVV EVKPLGIAPT
481  EARRRVVQQG GGGSGGGGSA VVGLGAVFLG FLGTAGSTMG AASITLTVQA RQLLSGIVQQ
541  QSNLLRAPEA QQHMLQLTVW GIKQLQARVL AIERYLKDQQ LLGMWGCSGK LICTTNVYWN
601  SSWSNKTYNE IWDNMTWMQW DREIDNYTDT IYKLLEVSQK QQESNEKDLL ALDSWNNLWN
661  WFDISKWLWY IKIFIMIVGG LIGLRIIFAV LSLVNRVRQG YSPLSFQTLT PNPRELDRLG
721  GIEEEGGEQD RDAAA*
```

Figure 12

```
1    MEWSWIFLFL LSGTAGVHSS GGLWVTVYYG VPVWREAKTT LFCASDAKSY EKEVHNVWAT
61   HACVPTDPNP QELVLKNVTE NFNMWKNDMV DQMHEDIISL WDQSLKPCVK LTPLCVTLNC
121  SDAKVNINAT YNGTREEIKN CSFNATTELR DKKKKEYALF YRLDIVPLNK EGNNNSEYRL
181  INCNTSVITQ ACPKVTFDPI PIHYCAPAGY AILKCNNKTF NGTGPCNNVS TVQCTHGIKP
241  VVSTQLLLNG SLAEEEIIIR SENLTDNVKT IIVHLNESVE INCTRPNNNT RKSIRIGPGQ
301  TFYATGDIIG DIRQAHCNIS EIKWEKTLQR VSEKLREHFN KTIIFNQSSG GDLEITTHSF
361  NCGGEFFYCN TSDLFFNKTF DETYSTGSNS TNSTITLPCR IKQIINMWQE VGRAMYASPI
421  AGEITCKSNI TGLLLTRDGG GNNSTEETFR PGGGNMRDNW RSELYKYKVV EVKPLGIAPT
481  EARRRVVQQG GGGSGGGGSA VVGLGAVFLG FLGTAGSTMG AASITLTVQA RQLLSGIVQQ
541  QSNLLRAPEA QQHMLQLTVW GIKQLQARVL AIERYLKDQQ LLGMWGCSGK LICTTNVYWN
601  SSWSNKTYNE IWDNMTWMQW DREIDNYTDT IYKLLEVSQK QQESNEKDLL ALDSWNNLWN
661  WFDISKWLWY IKIFIMIVGG LIGLRIIFAV LSLVNRVRQG YSPLSFQTLT PNPRELDRLG
721  GIEEEGGEQD RDRSIRLVSG FFSLAWNDLR SLCLFCYHRL RDFILIAGRA VELLGRSSLQ
781  GLQRGWEILK YLGSLVQYWG LELKKSAINL FDTIAIAVAE GTDRIIEEFL QRIVRAILHI
841  PRRIRQGFEA ALQ
```

Figure 13

```
1    MEWSWIFLFL LSGTAGVHSS GVGNLNLWVT VYYGVPVWKE AKTTLFCASD AKAYDKEVHN
61   VWATHACVPT DPNPREIVLE NVTENFNMWK NDMVDQMHED IISLWDQSLK PCVKLTPLCV
121  TLNCTNAPAY NNSMHGEMKN CSFNTTTEIR DRKQKAYALF YKPDVVPLNR REENNGTGEY
181  ILINCNSSTI TQACPKVTFD PIPIHYCAPA GYAILKCNNK TFNGTGPCNN VSTVQCTHGI
241  MPVVSTQLLL NGSLAEEEII IRSENLTNNI KTIIVHLNKS VEIVCTRPNN NTRKSIRIGP
301  GQTFYATGEI IGNIREAHCN ISKSNWTSTL EQVKKKLKEH YNKTIEFNPP SGGDLEVTTH
361  SFNCRGEFFY CNTTKLFSNN SDSNNETITL PCKIKQIINM WQKVGRAMYA PPIEGNITCK
421  SNITGLLLTR DGGKNTTNEI FRPGGGNMKD NWRSELYKYK VVEIEPLGVA PTKSKRRVVE
481  GGGGSGGGGS AVGLGAVLLG FLGAAGSTMG AASITLTVQA RQLLSGIVQQ QSNLLRAPEA
541  QQHMLQLTVW GIKQLQTRVL AIERYLKDQQ LLGLWGCSGK IICTTAVPWN SSWSNKSQED
601  IWDNMTWMQW DREISNYTGT IYRLLEDSQN QQEKNEKDLL ALDSWKNLWN WFNITNWLWY
661  IQILSIYSTV ASSLALAIMV AGLSLWMCSN GSLQCRAAA*
```

Figure 14

```
1    MEWSWIFLFL LSGTAGVHSS GVGNLNLWVT VYYGVPVWKE AKTTLFCASD AKAYDKEVHN
61   VWATHACVPT DPNPREIVLE NVTENFNMWK NDMVDQMHED IISLWDQSLK PCVKLTPLCV
121  TLNCTNAPAY NNSMHGEMKN CSFNTTTEIR DRKQKAYALF YKPDVVPLNR REENNGTGEY
181  ILINCNSSTI TQACPKVTFD PIPIHYCAPA GYAILKCNNK TFNGTGPCNN VSTVQCTHGI
241  MPVVSTQLLL NGSLAEEEII IRSENLTNNI KTIIVHLNKS VEIVCTRPNN NTRKSIRIGP
301  GQTFYATGEI IGNIREAHCN ISKSNWTSTL EQVKKKLKEH YNKTIEFNPP SGGDLEVTTH
361  SFNCRGEFFY CNTTKLFSNN SDSNNETITL PCKIKQIINM WQKVGRAMYA PPIEGNITCK
421  SNITGLLLTR DGGKNTTNEI FRPGGGNMKD NWRSELYKYK VVEIEPLGVA PTKSKRRVVE
481  GGGGSGGGGS EGGWQGMVDG WYGYHHSNEQ GSGYAADKES TQKAIDGVTN KVNSIIDKMN
541  TQFEAVGREF NNLERRIENL NKKMEDGFLD VWTYNAELLV LMENERTLDF HDSNVKNLYD
601  KVRLQLRDNA KELGNGCFEF YHKCDNECME SVRNGTYDYP QYSEEARLKR EEISGVKLES
661  IGIYQILSIY STVASSLALA IMVAGLSLWM CSNGSLQCRA AA*
```

Figure 15

```
1    MEWSWIFLFL LSGTAGVHSS GVGNLNLWVT VYYGVPVWKE AKTTLFCASD AKAYDKEVHN
61   VWATHACVPT DPNPREIVLE NVTENFNMWK NDMVDQMHED IISLWDQSLK PCVKLTPLCV
121  TLNCTNAPAY NNSMHGEMKN CSFNTTTEIR DRKQKAYALF YKPDVVPLNR REENNGTGEY
181  ILINCNSSTI TQACPKVTFD PIPIHYCAPA GYAILKCNNK TFNGTGPCNN VSTVQCTHGI
241  MPVVSTQLLL NGSLAEEEII IRSENLTNNI KTIIVHLNKS VEIVCTRPNN NTRKSIRIGP
301  GQTFYATGEI IGNIREAHCN ISKSNWTSTL EQVKKKLKEH YNKTIEFNPP SGGDLEVTTH
361  SFNCRGEFFY CNTTKLFSNN SDSNNETITL PCKIKQIINM WQKVGRAMYA PPIEGNITCK
421  SNITGLLLTR DGGKNTTNEI FRPGGGNMKD NWRSELYKYK VVEIEPLGVA PTKSKRRVVE
481  GGGGSGGGGS AVGLGAVLLG FLGAAGSTMG AASITLTVQA RQLLSGIVQQ QSNLLRAPEA
541  QQHMLQLTVW GIKQLQTRVL AIERYLKDQQ LLGLWGCSGK IICTTAVPWN SSWSNKSQED
601  IWDNMTWMQW DREISNYTGT IYRLLEDSQN QQEKNEKDLL ALDSWKNLWN WFNITNWLWY
661  IKIFIMIVGG LIGLRIIFGV LAIVKRVRQG YSPLSFQTLT PSPRGPDRLG RIEEEGGEQD
721  KDAAA*
```

Figure 16

```
1    MEWSWIFLFL LSGTAGVHSS GVGNLNLWVT VYYGVPVWKE AKTTLFCASD AKAYDKEVHN
61   VWATHACVPT DPNPREIVLE NVTENFNMWK NDMVDQMHED IISLWDQSLK PCVKLTPLCV
121  TLNCTNAPAY NNSMHGEMKN CSFNTTTEIR DRKQKAYALF YKPDVVPLNR REENNGTGEY
181  ILINCNSSTI TQACPKVTFD PIPIHYCAPA GYAILKCNNK TFNGTGPCNN VSTVQCTHGI
241  MPVVSTQLLL NGSLAEEEII IRSENLTNNI KTIIVHLNKS VEIVCTRPNN NTRKSIRIGP
301  GQTFYATGEI IGNIREAHCN ISKSNWTSTL EQVKKKLKEH YNKTIEFNPP SGGDLEVTTH
361  SFNCRGEFFY CNTTKLFSNN SDSNNETITL PCKIKQIINM WQKVGRAMYA PPIEGNITCK
421  SNITGLLLTR DGGKNTTNEI FRPGGGNMKD NWRSELYKYK VVEIEPLGVA PTKSKRRVVE
481  GGGGSGGGGS AVGLGAVLLG FLGAAGSTMG AASITLTVQA RQLLSGIVQQ QSNLLRAPEA
541  QQHMLQLTVW GIKQLQTRVL AIERYLKDQQ LLGLWGCSGK IICTTAVPWN SSWSNKSQED
601  IWDNMTWMQW DREISNYTGT IYRLLEDSQN QQEKNEKDLL ALDSWKNLWN WFNITNWLWY
661  IKIFIMIVGG LIGLRIIFGV LAIVKRVRQG YSPLSFQTLT PSPRGPDRLG RIEEEGGEQD
721  KDRSIRLVSG FLALAWDDLR SLCLFSYHHL RDFILIAARA AELLGRSSLR GLQRGWEALK
781  YLGNLVQYGG LELKRSAIKL FDTIAIAVAE GTDRILEVIQ RICRAIRHIP IRIRQGFEAA
841  LQ*
```

Figure 17

```
1    MEWSWIFLFL LSGTAGVHSS GGLWVTVYYG VPVWREAKTT LFCASDAKSY EKEVHNVWAT
61   HACVPTDPNP QELVLKNVTE NFMWKNDMV DQMHEDIISL WDQSLKPCVK LTPLCVTLNC
121  SDAKVNINAT YNGTREEIKN CSFNATTELR DKKKKEYALF YRLDIVPLNK EGNNNSEYRL
181  INCNTSVITQ ACPKVTFDPI PIHYCAPAGY AILKCNNKTF NGTGPCNNVS TVQCTHGIKP
241  VVSTQLLLNG SLAEEEIIIR SENLTDNVKT IIVHLNESVE INCTRPNNNT RKSIRIGPGQ
301  TFYATGDIIG DIRQAHCNIS EIKWEKTLQR VSEKLREHFN KTIIFNQSSG GDLEITTHSF
361  NCGGEFFYCN TSDLFFNKTF DETYSTGSNS TNSTITLPCR IKQIINMWQE VGRAMYASPI
421  AGEITCKSNI TGLLLTRDGG GNNSTEETFR PGGGNMRDNW RSELYKYKVV EVKPLGIAPT
481  EARRRVVQQG GGGSGGGGSA VVGLGAVFLG FLGTAGSTMG AASITLTVQA RQLLSGIVQQ
541  QSNLLRAPEA QQHMLQLTVW GIKQLQARVL AIERYLKDQQ LLGMWGCSGK LICTTNVYWN
601  SSWSNKTYNE IWDNMTWMQW DREIDNYTDT IYKLLEVSQK QQESNEKDLL ALDAAA*
```

Figure 18

```
1    MEWSWIFLFL LSGTAGVHSS GVGNLNLWVT VYYGVPVWKE AKTTLFCASD AKAYDKEVHN
61   VWATHACVPT DPNPREIVLE NVTENFNMWK NDMVDQMHED IISLWDQSLK PCVKLTPLCV
121  TLNCTNAPAY NNSMHGEMKN CSFNTTTEIR DRKQKAYALF YKPDVVPLNR REENNGTGEY
181  ILINCNSSTI TQACPKVTFD PIPIHYCAPA GYAILKCNNK TFNGTGPCNN VSTVQCTHGI
241  MPVVSTQLLL NGSLAEEEII IRSENLTNNI KTIIVHLNKS VEIVCTRPNN NTRKSIRIGP
301  GQTFYATGEI IGNIREAHCN ISKSNWTSTL EQVKKKLKEH YNKTIEFNPP SGGDLEVTTH
361  SFNCRGEFFY CNTTKLFSNN SDSNNETITL PCKIKQIINM WQKVGRAMYA PPIEGNITCK
421  SNITGLLLTR DGGKNTTNEI FRPGGGNMKD NWRSELYKYK VVEIEPLGVA PTKSKRRVVE
481  *GGGGSGGGGS* AVGLGAVLLG FLGAAGSTMG AASITLTVQA RQLLSGIVQQ QSNLLRAPEA
541  QQHMLQLTVW GIKQLQTRVL AIERYLKDQQ LLGLWGCSGK IICTTAVPWN SSWSNKSQED
601  IWDNMTWMQW DREISNYTGT IYRLLEDSQN QQEKNEKDLL ALDSWKNLWN WFNITNWLWY
661  IQILSIYSTV ASSLALAIMV AGLSLWMCSN GSLQCRAAA*
```

Figure 19

SEQUENCE LISTING

<160> NUMBER OF SEQ ID NOS: 22

<210> SEQ ID NO 1
<211> LENGTH: 853
<212> TYPE: PRT
<213> ORGANISM: HIV-1

<400> SEQUENCE: 1

Met Thr Val Thr Gly Thr Trp Arg Asn Tyr Gln Gln Trp Trp Ile Trp
1               5                   10                  15

Gly Ile Leu Gly Phe Trp Met Leu Met Ile Cys Asn Gly Leu Trp Val
            20                  25                  30

Thr Val Tyr Tyr Gly Val Pro Val Trp Arg Glu Ala Lys Thr Thr Leu
        35                  40                  45

Phe Cys Ala Ser Asp Ala Lys Ser Tyr Glu Lys Glu Val His Asn Val
    50                  55                  60

```
Trp Ala Thr His Ala Cys Val Pro Thr Asp Pro Asn Pro Gln Glu Leu
 65                  70                  75                  80

Val Leu Lys Asn Val Thr Glu Asn Phe Asn Met Trp Lys Asn Asp Met
                 85                  90                  95

Val Asp Gln Met His Glu Asp Ile Ile Ser Leu Trp Asp Gln Ser Leu
            100                 105                 110

Lys Pro Cys Val Lys Leu Thr Pro Leu Cys Val Thr Leu Asn Cys Ser
        115                 120                 125

Asp Ala Lys Val Asn Ile Asn Ala Thr Tyr Asn Gly Thr Arg Glu Glu
    130                 135                 140

Ile Lys Asn Cys Ser Phe Asn Ala Thr Thr Glu Leu Arg Asp Lys Lys
145                 150                 155                 160

Lys Lys Glu Tyr Ala Leu Phe Tyr Arg Leu Asp Ile Val Pro Leu Asn
                165                 170                 175

Lys Glu Gly Asn Asn Asn Ser Glu Tyr Arg Leu Ile Asn Cys Asn Thr
            180                 185                 190

Ser Val Ile Thr Gln Ala Cys Pro Lys Val Thr Phe Asp Pro Ile Pro
        195                 200                 205

Ile His Tyr Cys Ala Pro Ala Gly Tyr Ala Ile Leu Lys Cys Asn Asn
210                 215                 220

Lys Thr Phe Asn Gly Thr Gly Pro Cys Asn Asn Val Ser Thr Val Gln
225                 230                 235                 240

Cys Thr His Gly Ile Lys Pro Val Val Ser Thr Gln Leu Leu Leu Asn
            245                 250                 255

Gly Ser Leu Ala Glu Glu Glu Ile Ile Ile Arg Ser Glu Asn Leu Thr
            260                 265                 270

Asp Asn Val Lys Thr Ile Ile Val His Leu Asn Glu Ser Val Glu Ile
            275                 280                 285

Asn Cys Thr Arg Pro Asn Asn Asn Thr Arg Lys Ser Ile Arg Ile Gly
            290                 295                 300

Pro Gly Gln Thr Phe Tyr Ala Thr Gly Asp Ile Ile Gly Asp Ile Arg
305                 310                 315                 320

Gln Ala His Cys Asn Ile Ser Glu Ile Lys Trp Glu Lys Thr Leu Gln
                325                 330                 335

Arg Val Ser Glu Lys Leu Arg Glu His Phe Asn Lys Thr Ile Ile Phe
            340                 345                 350

Asn Gln Ser Ser Gly Gly Asp Leu Glu Ile Thr Thr His Ser Phe Asn
            355                 360                 365

Cys Gly Gly Glu Phe Phe Tyr Cys Asn Thr Ser Asp Leu Phe Phe Asn
            370                 375                 380

Lys Thr Phe Asp Glu Thr Tyr Ser Thr Gly Ser Asn Ser Thr Asn Ser
385                 390                 395                 400

Thr Ile Thr Leu Pro Cys Arg Ile Lys Gln Ile Ile Asn Met Trp Gln
                405                 410                 415

Glu Val Gly Arg Ala Met Tyr Ala Ser Pro Ile Ala Gly Glu Ile Thr
            420                 425                 430

Cys Lys Ser Asn Ile Thr Gly Leu Leu Leu Thr Arg Asp Gly Gly Gly
            435                 440                 445

Asn Asn Ser Thr Glu Glu Thr Phe Arg Pro Gly Gly Gly Asn Met Arg
            450                 455                 460

Asp Asn Trp Arg Ser Glu Leu Tyr Lys Tyr Lys Val Val Glu Val Lys
465                 470                 475                 480
```

-continued

Pro Leu Gly Ile Ala Pro Thr Glu Ala Arg Arg Val Val Gln Lys
              485                 490                 495

Glu Lys Arg Ala Val Val Gly Leu Gly Ala Val Phe Leu Gly Phe Leu
          500                 505                 510

Gly Thr Ala Gly Ser Thr Met Gly Ala Ala Ser Ile Thr Leu Thr Val
          515                 520                 525

Gln Ala Arg Gln Leu Leu Ser Gly Ile Val Gln Gln Ser Asn Leu
  530                 535                 540

Leu Arg Ala Ile Glu Ala Gln Gln His Met Leu Gln Leu Thr Val Trp
545                 550                 555                 560

Gly Ile Lys Gln Leu Gln Ala Arg Val Leu Ala Ile Glu Arg Tyr Leu
              565                 570                 575

Lys Asp Gln Gln Leu Leu Gly Met Trp Gly Cys Ser Gly Lys Leu Ile
              580                 585                 590

Cys Thr Thr Asn Val Tyr Trp Asn Ser Ser Trp Ser Asn Lys Thr Tyr
          595                 600                 605

Asn Glu Ile Trp Asp Asn Met Thr Trp Met Gln Trp Asp Arg Glu Ile
      610                 615                 620

Asp Asn Tyr Thr Asp Thr Ile Tyr Lys Leu Leu Glu Val Ser Gln Lys
625                 630                 635                 640

Gln Gln Glu Ser Asn Glu Lys Asp Leu Leu Ala Leu Asp Ser Trp Asn
              645                 650                 655

Asn Leu Trp Asn Trp Phe Asp Ile Ser Lys Trp Leu Trp Tyr Ile Lys
              660                 665                 670

Ile Phe Ile Met Ile Val Gly Gly Leu Ile Gly Leu Arg Ile Ile Phe
      675                 680                 685

Ala Val Leu Ser Leu Val Asn Arg Val Arg Gln Gly Tyr Ser Pro Leu
690                 695                 700

Ser Phe Gln Thr Leu Thr Pro Asn Pro Arg Glu Leu Asp Arg Leu Gly
705                 710                 715                 720

Gly Ile Glu Glu Glu Gly Gly Glu Gln Asp Arg Asp Arg Ser Ile Arg
              725                 730                 735

Leu Val Ser Gly Phe Phe Ser Leu Ala Trp Asn Asp Leu Arg Ser Leu
          740                 745                 750

Cys Leu Phe Cys Tyr His Arg Leu Arg Asp Phe Ile Leu Ile Ala Gly
      755                 760                 765

Arg Ala Val Glu Leu Leu Gly Arg Ser Ser Leu Gln Gly Leu Gln Arg
    770                 775                 780

Gly Trp Glu Ile Leu Lys Tyr Leu Gly Ser Leu Val Gln Tyr Trp Gly
785                 790                 795                 800

Leu Glu Leu Lys Lys Ser Ala Ile Asn Leu Phe Asp Thr Ile Ala Ile
              805                 810                 815

Ala Val Ala Glu Gly Thr Asp Arg Ile Ile Glu Glu Phe Leu Gln Arg
          820                 825                 830

Ile Val Arg Ala Ile Leu His Ile Pro Arg Arg Ile Arg Gln Gly Phe
      835                 840                 845

Glu Ala Ala Leu Gln
    850

<210> SEQ ID NO 2
<211> LENGTH: 844
<212> TYPE: PRT
<213> ORGANISM: HIV-1

<400> SEQUENCE: 2

```
Met Arg Val Met Gly Ile Gln Arg Asn Trp Pro Gln Trp Ile Trp
1               5                   10                  15

Gly Thr Leu Gly Phe Trp Met Ile Ile Ile Cys Arg Val Val Gly Asn
            20                  25                  30

Leu Asn Leu Trp Val Thr Val Tyr Tyr Gly Val Pro Val Trp Lys Glu
        35                  40                  45

Ala Lys Thr Thr Leu Phe Cys Ala Ser Asp Ala Lys Ala Tyr Asp Lys
    50                  55                  60

Glu Val His Asn Val Trp Ala Thr His Ala Cys Val Pro Thr Asp Pro
65                  70                  75                  80

Asn Pro Arg Glu Ile Val Leu Glu Asn Val Thr Glu Asn Phe Asn Met
                85                  90                  95

Trp Lys Asn Asp Met Val Asp Gln Met His Glu Asp Ile Ile Ser Leu
            100                 105                 110

Trp Asp Gln Ser Leu Lys Pro Cys Val Lys Leu Thr Pro Leu Cys Val
        115                 120                 125

Thr Leu Asn Cys Thr Asn Ala Pro Ala Tyr Asn Asn Ser Met His Gly
    130                 135                 140

Glu Met Lys Asn Cys Ser Phe Asn Thr Thr Glu Ile Arg Asp Arg
145                 150                 155                 160

Lys Gln Lys Ala Tyr Ala Leu Phe Tyr Lys Pro Asp Val Val Pro Leu
                165                 170                 175

Asn Arg Arg Glu Glu Asn Asn Gly Thr Gly Glu Tyr Ile Leu Ile Asn
            180                 185                 190

Cys Asn Ser Ser Thr Ile Thr Gln Ala Cys Pro Lys Val Thr Phe Asp
        195                 200                 205

Pro Ile Pro Ile His Tyr Cys Ala Pro Ala Gly Tyr Ala Ile Leu Lys
    210                 215                 220

Cys Asn Asn Lys Thr Phe Asn Gly Thr Gly Pro Cys Asn Asn Val Ser
225                 230                 235                 240

Thr Val Gln Cys Thr His Gly Ile Met Pro Val Val Ser Thr Gln Leu
                245                 250                 255

Leu Leu Asn Gly Ser Leu Ala Glu Glu Glu Ile Ile Arg Ser Glu
            260                 265                 270

Asn Leu Thr Asn Asn Ile Lys Thr Ile Ile Val His Leu Asn Lys Ser
        275                 280                 285

Val Glu Ile Val Cys Thr Arg Pro Asn Asn Thr Arg Lys Ser Ile
    290                 295                 300

Arg Ile Gly Pro Gly Gln Thr Phe Tyr Ala Thr Gly Glu Ile Ile Gly
305                 310                 315                 320

Asn Ile Arg Glu Ala His Cys Asn Ile Ser Lys Ser Asn Trp Thr Ser
                325                 330                 335

Thr Leu Glu Gln Val Lys Lys Leu Lys Glu His Tyr Asn Lys Thr
            340                 345                 350

Ile Glu Phe Asn Pro Pro Ser Gly Gly Asp Leu Glu Val Thr Thr His
        355                 360                 365

Ser Phe Asn Cys Arg Gly Glu Phe Phe Tyr Cys Asn Thr Thr Lys Leu
    370                 375                 380

Phe Ser Asn Asn Ser Asp Ser Asn Asn Glu Thr Ile Thr Leu Pro Cys
385                 390                 395                 400

Lys Ile Lys Gln Ile Ile Asn Met Trp Gln Lys Val Gly Arg Ala Met
                405                 410                 415
```

```
Tyr Ala Pro Pro Ile Glu Gly Asn Ile Thr Cys Lys Ser Asn Ile Thr
                420                 425                 430
Gly Leu Leu Leu Thr Arg Asp Gly Lys Asn Thr Thr Asn Glu Ile
        435                 440                 445
Phe Arg Pro Gly Gly Asn Met Lys Asp Asn Trp Arg Ser Glu Leu
        450                 455                 460
Tyr Lys Tyr Lys Val Val Glu Ile Glu Pro Leu Gly Val Ala Pro Thr
465                 470                 475                 480
Lys Ser Lys Arg Arg Val Val Glu Arg Glu Lys Arg Ala Val Gly Leu
                485                 490                 495
Gly Ala Val Leu Leu Gly Phe Leu Gly Ala Ala Gly Ser Thr Met Gly
            500                 505                 510
Ala Ala Ser Ile Thr Leu Thr Val Gln Ala Arg Gln Leu Leu Ser Gly
            515                 520                 525
Ile Val Gln Gln Gln Ser Asn Leu Leu Arg Ala Ile Glu Ala Gln Gln
            530                 535                 540
His Met Leu Gln Leu Thr Val Trp Gly Ile Lys Gln Leu Gln Thr Arg
545                 550                 555                 560
Val Leu Ala Ile Glu Arg Tyr Leu Lys Asp Gln Gln Leu Leu Gly Leu
                565                 570                 575
Trp Gly Cys Ser Gly Lys Ile Ile Cys Thr Thr Ala Val Pro Trp Asn
            580                 585                 590
Ser Ser Trp Ser Asn Lys Ser Gln Glu Asp Ile Trp Asp Asn Met Thr
            595                 600                 605
Trp Met Gln Trp Asp Arg Glu Ile Ser Asn Tyr Thr Gly Thr Ile Tyr
            610                 615                 620
Arg Leu Leu Glu Asp Ser Gln Asn Gln Gln Glu Lys Asn Glu Lys Asp
625                 630                 635                 640
Leu Leu Ala Leu Asp Ser Trp Lys Asn Leu Trp Asn Trp Phe Asn Ile
                645                 650                 655
Thr Asn Trp Leu Trp Tyr Ile Lys Ile Phe Ile Met Ile Val Gly Gly
            660                 665                 670
Leu Ile Gly Leu Arg Ile Ile Phe Gly Val Leu Ala Ile Val Lys Arg
            675                 680                 685
Val Arg Gln Gly Tyr Ser Pro Leu Ser Phe Gln Thr Leu Thr Pro Ser
690                 695                 700
Pro Arg Gly Pro Asp Arg Leu Gly Arg Ile Glu Glu Gly Gly Glu
705                 710                 715                 720
Gln Asp Lys Asp Arg Ser Ile Arg Leu Val Ser Gly Phe Leu Ala Leu
                725                 730                 735
Ala Trp Asp Asp Leu Arg Ser Leu Cys Leu Phe Ser Tyr His His Leu
            740                 745                 750
Arg Asp Phe Ile Leu Ile Ala Ala Arg Ala Ala Glu Leu Leu Gly Arg
            755                 760                 765
Ser Ser Leu Arg Gly Leu Gln Arg Gly Trp Glu Ala Leu Lys Tyr Leu
            770                 775                 780
Gly Asn Leu Val Gln Tyr Gly Gly Leu Glu Leu Lys Arg Ser Ala Ile
785                 790                 795                 800
Lys Leu Phe Asp Thr Ile Ala Ile Ala Val Ala Glu Gly Thr Asp Arg
                805                 810                 815
Ile Leu Glu Val Ile Gln Arg Ile Cys Arg Ala Ile Arg His Ile Pro
            820                 825                 830
Ile Arg Ile Arg Gln Gly Phe Glu Ala Ala Leu Gln
```

<210> SEQ ID NO 3
<211> LENGTH: 656
<212> TYPE: PRT
<213> ORGANISM: Artificial
<220> FEATURE:
<223> OTHER INFORMATION: CAP256SU Gp140NFL

<400> SEQUENCE: 3

```
Met Glu Trp Ser Trp Ile Phe Leu Phe Leu Leu Ser Gly Thr Ala Gly
1               5                   10                  15

Val His Ser Ser Gly Gly Leu Trp Val Thr Val Tyr Tyr Gly Val Pro
            20                  25                  30

Val Trp Arg Glu Ala Lys Thr Thr Leu Phe Cys Ala Ser Asp Ala Lys
        35                  40                  45

Ser Tyr Glu Lys Glu Val His Asn Val Trp Ala Thr His Ala Cys Val
    50                  55                  60

Pro Thr Asp Pro Asn Pro Gln Glu Leu Val Leu Lys Asn Val Thr Glu
65                  70                  75                  80

Asn Phe Asn Met Trp Lys Asn Asp Met Val Asp Gln Met His Glu Asp
                85                  90                  95

Ile Ile Ser Leu Trp Asp Gln Ser Leu Lys Pro Cys Val Lys Leu Thr
            100                 105                 110

Pro Leu Cys Val Thr Leu Asn Cys Ser Asp Ala Lys Val Asn Ile Asn
        115                 120                 125

Ala Thr Tyr Asn Gly Thr Arg Glu Glu Ile Lys Asn Cys Ser Phe Asn
    130                 135                 140

Ala Thr Thr Glu Leu Arg Asp Lys Lys Lys Glu Tyr Ala Leu Phe
145                 150                 155                 160

Tyr Arg Leu Asp Ile Val Pro Leu Asn Lys Glu Gly Asn Asn Asn Ser
                165                 170                 175

Glu Tyr Arg Leu Ile Asn Cys Asn Thr Ser Val Ile Thr Gln Ala Cys
            180                 185                 190

Pro Lys Val Thr Phe Asp Pro Ile Pro Ile His Tyr Cys Ala Pro Ala
        195                 200                 205

Gly Tyr Ala Ile Leu Lys Cys Asn Asn Lys Thr Phe Asn Gly Thr Gly
    210                 215                 220

Pro Cys Asn Asn Val Ser Thr Val Gln Cys Thr His Gly Ile Lys Pro
225                 230                 235                 240

Val Val Ser Thr Gln Leu Leu Leu Asn Gly Ser Leu Ala Glu Glu Glu
                245                 250                 255

Ile Ile Ile Arg Ser Glu Asn Leu Thr Asp Asn Val Lys Thr Ile Ile
            260                 265                 270

Val His Leu Asn Glu Ser Val Glu Ile Asn Cys Thr Arg Pro Asn Asn
        275                 280                 285

Asn Thr Arg Lys Ser Ile Arg Ile Gly Pro Gly Gln Thr Phe Tyr Ala
    290                 295                 300

Thr Gly Asp Ile Ile Gly Asp Ile Arg Gln Ala His Cys Asn Ile Ser
305                 310                 315                 320

Glu Ile Lys Trp Glu Lys Thr Leu Gln Arg Val Ser Glu Lys Leu Arg
                325                 330                 335

Glu His Phe Asn Lys Thr Ile Ile Phe Asn Gln Ser Ser Gly Gly Asp
            340                 345                 350

Leu Glu Ile Thr Thr His Ser Phe Asn Cys Gly Gly Glu Phe Phe Tyr
```

```
                355                 360                 365
        Cys Asn Thr Ser Asp Leu Phe Phe Asn Lys Thr Phe Asp Glu Thr Tyr
            370                 375                 380

Ser Thr Gly Ser Asn Ser Thr Asn Ser Thr Ile Thr Leu Pro Cys Arg
        385                 390                 395                 400

Ile Lys Gln Ile Ile Asn Met Trp Gln Glu Val Gly Arg Ala Met Tyr
                        405                 410                 415

Ala Ser Pro Ile Ala Gly Glu Ile Thr Cys Lys Ser Asn Ile Thr Gly
                    420                 425                 430

Leu Leu Leu Thr Arg Asp Gly Gly Asn Asn Ser Thr Glu Glu Thr
                435                 440                 445

Phe Arg Pro Gly Gly Gly Asn Met Arg Asp Asn Trp Arg Ser Glu Leu
            450                 455                 460

Tyr Lys Tyr Lys Val Val Glu Val Lys Pro Leu Gly Ile Ala Pro Thr
        465                 470                 475                 480

Glu Ala Arg Arg Arg Val Val Gln Gln Gly Gly Gly Ser Gly Gly
                        485                 490                 495

Gly Gly Ser Ala Val Val Gly Leu Gly Ala Val Phe Leu Gly Phe Leu
                    500                 505                 510

Gly Thr Ala Gly Ser Thr Met Gly Ala Ala Ser Ile Thr Leu Thr Val
                515                 520                 525

Gln Ala Arg Gln Leu Leu Ser Gly Ile Val Gln Gln Ser Asn Leu
            530                 535                 540

Leu Arg Ala Pro Glu Ala Gln Gln His Met Leu Gln Leu Thr Val Trp
        545                 550                 555                 560

Gly Ile Lys Gln Leu Gln Ala Arg Val Leu Ala Ile Glu Arg Tyr Leu
                        565                 570                 575

Lys Asp Gln Gln Leu Leu Gly Met Trp Gly Cys Ser Gly Lys Leu Ile
                    580                 585                 590

Cys Thr Thr Asn Val Tyr Trp Asn Ser Ser Trp Ser Asn Lys Thr Tyr
                595                 600                 605

Asn Glu Ile Trp Asp Asn Met Thr Trp Met Gln Trp Asp Arg Glu Ile
            610                 615                 620

Asp Asn Tyr Thr Asp Thr Ile Tyr Lys Leu Leu Glu Val Ser Gln Lys
        625                 630                 635                 640

Gln Gln Glu Ser Asn Glu Lys Asp Leu Leu Ala Leu Asp Ala Ala Ala
                        645                 650                 655

<210> SEQ ID NO 4
<211> LENGTH: 709
<212> TYPE: PRT
<213> ORGANISM: Artificial
<220> FEATURE:
<223> OTHER INFORMATION: CAP256SU Gp140FL fused to HA2 of influenza

<400> SEQUENCE: 4

Met Glu Trp Ser Trp Ile Phe Leu Phe Leu Leu Ser Gly Thr Ala Gly
        1               5                   10                  15

Val His Ser Ser Gly Gly Leu Trp Val Thr Val Tyr Tyr Gly Val Pro
                        20                  25                  30

Val Trp Arg Glu Ala Lys Thr Thr Leu Phe Cys Ala Ser Asp Ala Lys
                    35                  40                  45

Ser Tyr Glu Lys Glu Val His Asn Val Trp Ala Thr His Ala Cys Val
                50                  55                  60

Pro Thr Asp Pro Asn Pro Gln Glu Leu Val Leu Lys Asn Val Thr Glu
```

```
                65                  70                  75                  80
Asn Phe Asn Met Trp Lys Asn Asp Met Val Asp Gln Met His Glu Asp
                    85                  90                  95
Ile Ile Ser Leu Trp Asp Gln Ser Leu Lys Pro Cys Val Lys Leu Thr
                100                 105                 110
Pro Leu Cys Val Thr Leu Asn Cys Ser Asp Ala Lys Val Asn Ile Asn
                115                 120                 125
Ala Thr Tyr Asn Gly Thr Arg Glu Ile Lys Asn Cys Ser Phe Asn
130                 135                 140
Ala Thr Thr Glu Leu Arg Asp Lys Lys Lys Glu Tyr Ala Leu Phe
145                 150                 155                 160
Tyr Arg Leu Asp Ile Val Pro Leu Asn Lys Glu Gly Asn Asn Asn Ser
                165                 170                 175
Glu Tyr Arg Leu Ile Asn Cys Asn Thr Ser Val Ile Thr Gln Ala Cys
                180                 185                 190
Pro Lys Val Thr Phe Asp Pro Ile Pro Ile His Tyr Cys Ala Pro Ala
                195                 200                 205
Gly Tyr Ala Ile Leu Lys Cys Asn Asn Lys Thr Phe Asn Gly Thr Gly
                210                 215                 220
Pro Cys Asn Asn Val Ser Thr Val Gln Cys Thr His Gly Ile Lys Pro
225                 230                 235                 240
Val Val Ser Thr Gln Leu Leu Leu Asn Gly Ser Leu Ala Glu Glu
                245                 250                 255
Ile Ile Ile Arg Ser Glu Asn Leu Thr Asp Asn Val Lys Thr Ile Ile
                260                 265                 270
Val His Leu Asn Glu Ser Val Glu Ile Asn Cys Thr Arg Pro Asn Asn
                275                 280                 285
Asn Thr Arg Lys Ser Ile Arg Ile Gly Pro Gly Gln Thr Phe Tyr Ala
                290                 295                 300
Thr Gly Asp Ile Ile Gly Asp Ile Arg Gln Ala His Cys Asn Ile Ser
305                 310                 315                 320
Glu Ile Lys Trp Glu Lys Thr Leu Gln Arg Val Ser Glu Lys Leu Arg
                325                 330                 335
Glu His Phe Asn Lys Thr Ile Ile Phe Asn Gln Ser Ser Gly Gly Asp
                340                 345                 350
Leu Glu Ile Thr Thr His Ser Phe Asn Cys Gly Gly Glu Phe Phe Tyr
                355                 360                 365
Cys Asn Thr Ser Asp Leu Phe Phe Asn Lys Thr Phe Asp Glu Thr Tyr
                370                 375                 380
Ser Thr Gly Ser Asn Ser Thr Asn Ser Thr Ile Thr Leu Pro Cys Arg
385                 390                 395                 400
Ile Lys Gln Ile Ile Asn Met Trp Gln Glu Val Gly Arg Ala Met Tyr
                405                 410                 415
Ala Ser Pro Ile Ala Gly Glu Ile Thr Cys Lys Ser Asn Ile Thr Gly
                420                 425                 430
Leu Leu Leu Thr Arg Asp Gly Gly Asn Asn Ser Thr Glu Glu Thr
                435                 440                 445
Phe Arg Pro Gly Gly Gly Asn Met Arg Asp Asn Trp Arg Ser Glu Leu
                450                 455                 460
Tyr Lys Tyr Lys Val Val Glu Val Lys Pro Leu Gly Ile Ala Pro Thr
465                 470                 475                 480
Glu Ala Arg Arg Arg Val Val Gln Gln Gly Gly Gly Ser Gly Gly
                485                 490                 495
```

Gly Gly Ser Ala Val Val Gly Leu Gly Ala Val Phe Leu Gly Phe Leu
              500                 505                 510

Gly Thr Ala Gly Ser Thr Met Gly Ala Ala Ser Ile Thr Leu Thr Val
              515                 520                 525

Gln Ala Arg Gln Leu Leu Ser Gly Ile Val Gln Gln Gln Ser Asn Leu
              530                 535                 540

Leu Arg Ala Pro Glu Ala Gln Gln His Met Leu Gln Leu Thr Val Trp
545                 550                 555                 560

Gly Ile Lys Gln Leu Gln Ala Arg Val Leu Ala Ile Glu Arg Tyr Leu
              565                 570                 575

Lys Asp Gln Gln Leu Leu Gly Met Trp Gly Cys Ser Gly Lys Leu Ile
              580                 585                 590

Cys Thr Thr Asn Val Tyr Trp Asn Ser Ser Trp Ser Asn Lys Thr Tyr
              595                 600                 605

Asn Glu Ile Trp Asp Asn Met Thr Trp Met Gln Trp Asp Arg Glu Ile
              610                 615                 620

Asp Asn Tyr Thr Asp Thr Ile Tyr Lys Leu Leu Glu Val Ser Gln Lys
625                 630                 635                 640

Gln Gln Glu Ser Asn Glu Lys Asp Leu Leu Ala Leu Asp Ser Trp Asn
              645                 650                 655

Asn Leu Trp Asn Trp Phe Asp Ile Ser Lys Trp Leu Trp Tyr Ile Gln
              660                 665                 670

Ile Leu Ser Ile Tyr Ser Thr Val Ala Ser Ser Leu Ala Leu Ala Ile
              675                 680                 685

Met Val Ala Gly Leu Ser Leu Trp Met Cys Ser Asn Gly Ser Leu Gln
              690                 695                 700

Cys Arg Ala Ala Ala
705

<210> SEQ ID NO 5
<211> LENGTH: 711
<212> TYPE: PRT
<213> ORGANISM: Artificial
<220> FEATURE:
<223> OTHER INFORMATION: CAP256SU Gp120FL fused to HA2 of influenza

<400> SEQUENCE: 5

Met Glu Trp Ser Trp Ile Phe Leu Phe Leu Leu Ser Gly Thr Ala Gly
1               5                   10                  15

Val His Ser Ser Gly Gly Leu Trp Val Thr Val Tyr Tyr Gly Val Pro
              20                  25                  30

Val Trp Arg Glu Ala Lys Thr Thr Leu Phe Cys Ala Ser Asp Ala Lys
              35                  40                  45

Ser Tyr Glu Lys Glu Val His Asn Val Trp Ala Thr His Ala Cys Val
              50                  55                  60

Pro Thr Asp Pro Asn Pro Gln Glu Leu Val Leu Lys Asn Val Thr Glu
65                  70                  75                  80

Asn Phe Asn Met Trp Lys Asn Asp Met Val Asp Gln Met His Glu Asp
              85                  90                  95

Ile Ile Ser Leu Trp Asp Gln Ser Leu Lys Pro Cys Val Lys Leu Thr
              100                 105                 110

Pro Leu Cys Val Thr Leu Asn Cys Ser Asp Ala Lys Val Asn Ile Asn
              115                 120                 125

Ala Thr Tyr Asn Gly Thr Arg Glu Glu Ile Lys Asn Cys Ser Phe Asn
              130                 135                 140

```
Ala Thr Thr Glu Leu Arg Asp Lys Lys Lys Glu Tyr Ala Leu Phe
145                 150                 155                 160

Tyr Arg Leu Asp Ile Val Pro Leu Asn Lys Glu Gly Asn Asn Asn Ser
            165                 170                 175

Glu Tyr Arg Leu Ile Asn Cys Asn Thr Ser Val Ile Thr Gln Ala Cys
            180                 185                 190

Pro Lys Val Thr Phe Asp Pro Ile Pro Ile His Tyr Cys Ala Pro Ala
            195                 200                 205

Gly Tyr Ala Ile Leu Lys Cys Asn Asn Lys Thr Phe Asn Gly Thr Gly
            210                 215                 220

Pro Cys Asn Asn Val Ser Thr Val Gln Cys Thr His Gly Ile Lys Pro
225                 230                 235                 240

Val Val Ser Thr Gln Leu Leu Leu Asn Gly Ser Leu Ala Glu Glu
                245                 250                 255

Ile Ile Ile Arg Ser Glu Asn Leu Thr Asp Asn Val Lys Thr Ile Ile
            260                 265                 270

Val His Leu Asn Glu Ser Val Glu Ile Asn Cys Thr Arg Pro Asn Asn
            275                 280                 285

Asn Thr Arg Lys Ser Ile Arg Ile Gly Pro Gly Gln Thr Phe Tyr Ala
290                 295                 300

Thr Gly Asp Ile Ile Gly Asp Ile Arg Gln Ala His Cys Asn Ile Ser
305                 310                 315                 320

Glu Ile Lys Trp Glu Lys Thr Leu Gln Arg Val Ser Glu Lys Leu Arg
            325                 330                 335

Glu His Phe Asn Lys Thr Ile Ile Phe Asn Gln Ser Ser Gly Gly Asp
            340                 345                 350

Leu Glu Ile Thr Thr His Ser Phe Asn Cys Gly Gly Glu Phe Phe Tyr
            355                 360                 365

Cys Asn Thr Ser Asp Leu Phe Phe Asn Lys Thr Phe Asp Glu Thr Tyr
    370                 375                 380

Ser Thr Gly Ser Asn Ser Thr Asn Ser Thr Ile Thr Leu Pro Cys Arg
385                 390                 395                 400

Ile Lys Gln Ile Ile Asn Met Trp Gln Glu Val Gly Arg Ala Met Tyr
            405                 410                 415

Ala Ser Pro Ile Ala Gly Glu Ile Thr Cys Lys Ser Asn Ile Thr Gly
            420                 425                 430

Leu Leu Leu Thr Arg Asp Gly Gly Asn Asn Ser Thr Glu Glu Thr
                435                 440                 445

Phe Arg Pro Gly Gly Gly Asn Met Arg Asp Asn Trp Arg Ser Glu Leu
            450                 455                 460

Tyr Lys Tyr Lys Val Val Glu Val Lys Pro Leu Gly Ile Ala Pro Thr
465                 470                 475                 480

Glu Ala Arg Arg Arg Val Val Gln Gln Gly Gly Gly Ser Gly Gly
                485                 490                 495

Gly Gly Ser Glu Gly Gly Trp Gln Gly Met Val Asp Gly Trp Tyr Gly
            500                 505                 510

Tyr His His Ser Asn Glu Gln Gly Ser Gly Tyr Ala Ala Asp Lys Glu
            515                 520                 525

Ser Thr Gln Lys Ala Ile Asp Gly Val Thr Asn Lys Val Asn Ser Ile
            530                 535                 540

Ile Asp Lys Met Asn Thr Gln Phe Glu Ala Val Gly Arg Glu Phe Asn
545                 550                 555                 560
```

Asn Leu Glu Arg Arg Ile Glu Asn Leu Asn Lys Lys Met Glu Asp Gly
            565                 570                 575

Phe Leu Asp Val Trp Thr Tyr Asn Ala Glu Leu Leu Val Leu Met Glu
            580                 585                 590

Asn Glu Arg Thr Leu Asp Phe His Asp Ser Asn Val Lys Asn Leu Tyr
            595                 600                 605

Asp Lys Val Arg Leu Gln Leu Arg Asp Asn Ala Lys Glu Leu Gly Asn
    610                 615                 620

Gly Cys Phe Glu Phe Tyr His Lys Cys Asp Asn Glu Cys Met Glu Ser
625                 630                 635                 640

Val Arg Asn Gly Thr Tyr Asp Tyr Pro Gln Tyr Ser Glu Glu Ala Arg
                645                 650                 655

Leu Lys Arg Glu Glu Ile Ser Gly Val Lys Leu Glu Ser Ile Gly Ile
            660                 665                 670

Tyr Gln Ile Leu Ser Ile Tyr Ser Thr Val Ala Ser Ser Leu Ala Leu
            675                 680                 685

Ala Ile Met Val Ala Gly Leu Ser Leu Trp Met Cys Ser Asn Gly Ser
            690                 695                 700

Leu Gln Cys Arg Ala Ala Ala
705                 710

<210> SEQ ID NO 6
<211> LENGTH: 735
<212> TYPE: PRT
<213> ORGANISM: Artificial
<220> FEATURE:
<223> OTHER INFORMATION: CAP256SU Gp150FL

<400> SEQUENCE: 6

Met Glu Trp Ser Trp Ile Phe Leu Phe Leu Leu Ser Gly Thr Ala Gly
1               5                   10                  15

Val His Ser Ser Gly Gly Leu Trp Val Thr Val Tyr Tyr Gly Val Pro
            20                  25                  30

Val Trp Arg Glu Ala Lys Thr Thr Leu Phe Cys Ala Ser Asp Ala Lys
        35                  40                  45

Ser Tyr Glu Lys Glu Val His Asn Val Trp Ala Thr His Ala Cys Val
    50                  55                  60

Pro Thr Asp Pro Asn Pro Gln Glu Leu Val Leu Lys Asn Val Thr Glu
65                  70                  75                  80

Asn Phe Asn Met Trp Lys Asn Asp Met Val Asp Gln Met His Glu Asp
                85                  90                  95

Ile Ile Ser Leu Trp Asp Gln Ser Leu Lys Pro Cys Val Lys Leu Thr
            100                 105                 110

Pro Leu Cys Val Thr Leu Asn Cys Ser Asp Ala Lys Val Asn Ile Asn
        115                 120                 125

Ala Thr Tyr Asn Gly Thr Arg Glu Glu Ile Lys Asn Cys Ser Phe Asn
    130                 135                 140

Ala Thr Thr Glu Leu Arg Asp Lys Lys Lys Glu Tyr Ala Leu Phe
145                 150                 155                 160

Tyr Arg Leu Asp Ile Val Pro Leu Asn Lys Glu Gly Asn Asn Ser
                165                 170                 175

Glu Tyr Arg Leu Ile Asn Cys Asn Thr Ser Val Ile Thr Gln Ala Cys
            180                 185                 190

Pro Lys Val Thr Phe Asp Pro Ile Pro Ile His Tyr Cys Ala Pro Ala
        195                 200                 205

```
Gly Tyr Ala Ile Leu Lys Cys Asn Asn Lys Thr Phe Asn Gly Thr Gly
    210                 215                 220
Pro Cys Asn Asn Val Ser Thr Val Gln Cys Thr His Gly Ile Lys Pro
225                 230                 235                 240
Val Val Ser Thr Gln Leu Leu Leu Asn Gly Ser Leu Ala Glu Glu Glu
                245                 250                 255
Ile Ile Ile Arg Ser Glu Asn Leu Thr Asp Asn Val Lys Thr Ile Ile
            260                 265                 270
Val His Leu Asn Glu Ser Val Glu Ile Asn Cys Thr Arg Pro Asn Asn
        275                 280                 285
Asn Thr Arg Lys Ser Ile Arg Ile Gly Pro Gly Gln Thr Phe Tyr Ala
290                 295                 300
Thr Gly Asp Ile Ile Gly Asp Ile Arg Gln Ala His Cys Asn Ile Ser
305                 310                 315                 320
Glu Ile Lys Trp Glu Lys Thr Leu Gln Arg Val Ser Glu Lys Leu Arg
                325                 330                 335
Glu His Phe Asn Lys Thr Ile Ile Phe Asn Gln Ser Ser Gly Gly Asp
            340                 345                 350
Leu Glu Ile Thr Thr His Ser Phe Asn Cys Gly Gly Glu Phe Phe Tyr
        355                 360                 365
Cys Asn Thr Ser Asp Leu Phe Phe Asn Lys Thr Phe Asp Glu Thr Tyr
370                 375                 380
Ser Thr Gly Ser Asn Ser Thr Asn Ser Thr Ile Thr Leu Pro Cys Arg
385                 390                 395                 400
Ile Lys Gln Ile Ile Asn Met Trp Gln Glu Val Gly Arg Ala Met Tyr
                405                 410                 415
Ala Ser Pro Ile Ala Gly Glu Ile Thr Cys Lys Ser Asn Ile Thr Gly
            420                 425                 430
Leu Leu Leu Thr Arg Asp Gly Gly Asn Asn Ser Thr Glu Glu Thr
        435                 440                 445
Phe Arg Pro Gly Gly Gly Asn Met Arg Asp Asn Trp Arg Ser Glu Leu
450                 455                 460
Tyr Lys Tyr Lys Val Val Glu Val Lys Pro Leu Gly Ile Ala Pro Thr
465                 470                 475                 480
Glu Ala Arg Arg Arg Val Val Gln Gln Gly Gly Gly Ser Gly Gly
                485                 490                 495
Gly Gly Ser Ala Val Val Gly Leu Gly Ala Val Phe Leu Gly Phe Leu
            500                 505                 510
Gly Thr Ala Gly Ser Thr Met Gly Ala Ala Ser Ile Thr Leu Thr Val
        515                 520                 525
Gln Ala Arg Gln Leu Leu Ser Gly Ile Val Gln Gln Gln Ser Asn Leu
530                 535                 540
Leu Arg Ala Pro Glu Ala Gln Gln His Met Leu Gln Leu Thr Val Trp
545                 550                 555                 560
Gly Ile Lys Gln Leu Gln Ala Arg Val Leu Ala Ile Glu Arg Tyr Leu
                565                 570                 575
Lys Asp Gln Gln Leu Leu Gly Met Trp Gly Cys Ser Gly Lys Leu Ile
            580                 585                 590
Cys Thr Thr Asn Val Tyr Trp Asn Ser Ser Trp Ser Asn Lys Thr Tyr
        595                 600                 605
Asn Glu Ile Trp Asp Asn Met Thr Trp Met Gln Trp Asp Arg Glu Ile
610                 615                 620
Asp Asn Tyr Thr Asp Thr Ile Tyr Lys Leu Leu Glu Val Ser Gln Lys
```

-continued

```
                625                 630                 635                 640
        Gln Gln Glu Ser Asn Glu Lys Asp Leu Leu Ala Leu Asp Ser Trp Asn
                        645                 650                 655

Asn Leu Trp Asn Trp Phe Asp Ile Ser Lys Trp Leu Trp Tyr Ile Lys
                        660                 665                 670

Ile Phe Ile Met Ile Val Gly Gly Leu Ile Gly Leu Arg Ile Ile Phe
                        675                 680                 685

Ala Val Leu Ser Leu Val Asn Arg Val Arg Gln Gly Tyr Ser Pro Leu
                        690                 695                 700

Ser Phe Gln Thr Leu Thr Pro Asn Pro Arg Glu Leu Asp Arg Leu Gly
        705                 710                 715                 720

Gly Ile Glu Glu Glu Gly Gly Glu Gln Asp Arg Asp Ala Ala Ala
                        725                 730                 735

<210> SEQ ID NO 7
<211> LENGTH: 853
<212> TYPE: PRT
<213> ORGANISM: Artificial
<220> FEATURE:
<223> OTHER INFORMATION: CAP256SU Gp160FL

<400> SEQUENCE: 7

Met Glu Trp Ser Trp Ile Phe Leu Phe Leu Leu Ser Gly Thr Ala Gly
        1               5                   10                  15

Val His Ser Ser Gly Gly Leu Trp Val Thr Val Tyr Tyr Gly Val Pro
                        20                  25                  30

Val Trp Arg Glu Ala Lys Thr Thr Leu Phe Cys Ala Ser Asp Ala Lys
                        35                  40                  45

Ser Tyr Glu Lys Glu Val His Asn Val Trp Ala Thr His Ala Cys Val
                        50                  55                  60

Pro Thr Asp Pro Asn Pro Gln Glu Leu Val Leu Lys Asn Val Thr Glu
        65                  70                  75                  80

Asn Phe Asn Met Trp Lys Asn Asp Met Val Asp Gln Met His Glu Asp
                        85                  90                  95

Ile Ile Ser Leu Trp Asp Gln Ser Leu Lys Pro Cys Val Lys Leu Thr
                        100                 105                 110

Pro Leu Cys Val Thr Leu Asn Cys Ser Asp Ala Lys Val Asn Ile Asn
                        115                 120                 125

Ala Thr Tyr Asn Gly Thr Arg Glu Glu Ile Lys Asn Cys Ser Phe Asn
                        130                 135                 140

Ala Thr Thr Glu Leu Arg Asp Lys Lys Lys Glu Tyr Ala Leu Phe
        145                 150                 155                 160

Tyr Arg Leu Asp Ile Val Pro Leu Asn Lys Glu Gly Asn Asn Asn Ser
                        165                 170                 175

Glu Tyr Arg Leu Ile Asn Cys Asn Thr Ser Val Ile Thr Gln Ala Cys
                        180                 185                 190

Pro Lys Val Thr Phe Asp Pro Ile Pro Ile His Tyr Cys Ala Pro Ala
                        195                 200                 205

Gly Tyr Ala Ile Leu Lys Cys Asn Asn Lys Thr Phe Asn Gly Thr Gly
                        210                 215                 220

Pro Cys Asn Asn Val Ser Thr Val Gln Cys Thr His Gly Ile Lys Pro
        225                 230                 235                 240

Val Val Ser Thr Gln Leu Leu Leu Asn Gly Ser Leu Ala Glu Glu Glu
                        245                 250                 255

Ile Ile Ile Arg Ser Glu Asn Leu Thr Asp Asn Val Lys Thr Ile Ile
```

```
              260              265              270
    Val His Leu Asn Glu Ser Val Glu Ile Asn Cys Thr Arg Pro Asn Asn
                275              280              285
    Asn Thr Arg Lys Ser Ile Arg Ile Gly Pro Gly Gln Thr Phe Tyr Ala
                290              295              300
    Thr Gly Asp Ile Ile Gly Asp Ile Arg Gln Ala His Cys Asn Ile Ser
    305              310              315              320
    Glu Ile Lys Trp Glu Lys Thr Leu Gln Arg Val Ser Glu Lys Leu Arg
                325              330              335
    Glu His Phe Asn Lys Thr Ile Ile Phe Asn Gln Ser Ser Gly Gly Asp
                340              345              350
    Leu Glu Ile Thr Thr His Ser Phe Asn Cys Gly Gly Glu Phe Phe Tyr
                355              360              365
    Cys Asn Thr Ser Asp Leu Phe Phe Asn Lys Thr Phe Asp Glu Thr Tyr
                370              375              380
    Ser Thr Gly Ser Asn Ser Thr Asn Ser Thr Ile Thr Leu Pro Cys Arg
    385              390              395              400
    Ile Lys Gln Ile Ile Asn Met Trp Gln Glu Val Gly Arg Ala Met Tyr
                405              410              415
    Ala Ser Pro Ile Ala Gly Glu Ile Thr Cys Lys Ser Asn Ile Thr Gly
                420              425              430
    Leu Leu Leu Thr Arg Asp Gly Gly Asn Asn Ser Thr Glu Glu Thr
                435              440              445
    Phe Arg Pro Gly Gly Gly Asn Met Arg Asp Asn Trp Arg Ser Glu Leu
                450              455              460
    Tyr Lys Tyr Lys Val Val Glu Val Lys Pro Leu Gly Ile Ala Pro Thr
    465              470              475              480
    Glu Ala Arg Arg Arg Val Val Gln Gln Gly Gly Gly Ser Gly Gly
                485              490              495
    Gly Gly Ser Ala Val Val Gly Leu Gly Ala Val Phe Leu Gly Phe Leu
                500              505              510
    Gly Thr Ala Gly Ser Thr Met Gly Ala Ala Ser Ile Thr Leu Thr Val
                515              520              525
    Gln Ala Arg Gln Leu Leu Ser Gly Ile Val Gln Gln Gln Ser Asn Leu
                530              535              540
    Leu Arg Ala Pro Glu Ala Gln Gln His Met Leu Gln Leu Thr Val Trp
    545              550              555              560
    Gly Ile Lys Gln Leu Gln Ala Arg Val Leu Ala Ile Glu Arg Tyr Leu
                565              570              575
    Lys Asp Gln Gln Leu Leu Gly Met Trp Gly Cys Ser Gly Lys Leu Ile
                580              585              590
    Cys Thr Thr Asn Val Tyr Trp Asn Ser Ser Trp Ser Asn Lys Thr Tyr
                595              600              605
    Asn Glu Ile Trp Asp Asn Met Thr Trp Met Gln Trp Asp Arg Glu Ile
                610              615              620
    Asp Asn Tyr Thr Asp Thr Ile Tyr Lys Leu Leu Glu Val Ser Gln Lys
    625              630              635              640
    Gln Gln Glu Ser Asn Glu Lys Asp Leu Leu Ala Leu Asp Ser Trp Asn
                645              650              655
    Asn Leu Trp Asn Trp Phe Asp Ile Ser Lys Trp Leu Trp Tyr Ile Lys
                660              665              670
    Ile Phe Ile Met Ile Val Gly Gly Leu Ile Gly Leu Arg Ile Ile Phe
                675              680              685
```

```
Ala Val Leu Ser Leu Val Asn Arg Val Arg Gln Gly Tyr Ser Pro Leu
        690                 695                 700

Ser Phe Gln Thr Leu Thr Pro Asn Pro Arg Glu Leu Asp Arg Leu Gly
705                 710                 715                 720

Gly Ile Glu Glu Glu Gly Gly Glu Gln Asp Arg Asp Arg Ser Ile Arg
                725                 730                 735

Leu Val Ser Gly Phe Phe Ser Leu Ala Trp Asn Asp Leu Arg Ser Leu
            740                 745                 750

Cys Leu Phe Cys Tyr His Arg Leu Arg Asp Phe Ile Leu Ile Ala Gly
        755                 760                 765

Arg Ala Val Glu Leu Leu Gly Arg Ser Ser Leu Gln Gly Leu Gln Arg
770                 775                 780

Gly Trp Glu Ile Leu Lys Tyr Leu Gly Ser Leu Val Gln Tyr Trp Gly
785                 790                 795                 800

Leu Glu Leu Lys Lys Ser Ala Ile Asn Leu Phe Asp Thr Ile Ala Ile
                805                 810                 815

Ala Val Ala Glu Gly Thr Asp Arg Ile Ile Glu Glu Phe Leu Gln Arg
                820                 825                 830

Ile Val Arg Ala Ile Leu His Ile Pro Arg Arg Ile Arg Gln Gly Phe
            835                 840                 845

Glu Ala Ala Leu Gln
    850

<210> SEQ ID NO 8
<211> LENGTH: 646
<212> TYPE: PRT
<213> ORGANISM: Artificial
<220> FEATURE:
<223> OTHER INFORMATION: Du151 Gp140NFL

<400> SEQUENCE: 8

Met Glu Trp Ser Trp Ile Phe Leu Phe Leu Leu Ser Gly Thr Ala Gly
1               5                   10                  15

Val His Ser Ser Gly Val Gly Asn Leu Asn Leu Trp Val Thr Val Tyr
                20                  25                  30

Tyr Gly Val Pro Val Trp Lys Glu Ala Lys Thr Thr Leu Phe Cys Ala
            35                  40                  45

Ser Asp Ala Lys Ala Tyr Asp Lys Glu Val His Asn Val Trp Ala Thr
        50                  55                  60

His Ala Cys Val Pro Thr Asp Pro Asn Pro Arg Glu Ile Val Leu Glu
65                  70                  75                  80

Asn Val Thr Glu Asn Phe Asn Met Trp Lys Asn Asp Met Val Asp Gln
                85                  90                  95

Met His Glu Asp Ile Ile Ser Leu Trp Asp Gln Ser Leu Lys Pro Cys
            100                 105                 110

Val Lys Leu Thr Pro Leu Cys Val Thr Leu Asn Cys Thr Asn Ala Pro
        115                 120                 125

Ala Tyr Asn Asn Ser Met His Gly Glu Met Lys Asn Cys Ser Phe Asn
    130                 135                 140

Thr Thr Thr Glu Ile Arg Asp Arg Lys Gln Lys Ala Tyr Ala Leu Phe
145                 150                 155                 160

Tyr Lys Pro Asp Val Val Pro Leu Asn Arg Arg Glu Glu Asn Asn Gly
                165                 170                 175

Thr Gly Glu Tyr Ile Leu Ile Asn Cys Asn Ser Ser Thr Ile Thr Gln
            180                 185                 190
```

```
Ala Cys Pro Lys Val Thr Phe Asp Pro Ile Pro Ile His Tyr Cys Ala
        195                 200                 205

Pro Ala Gly Tyr Ala Ile Leu Lys Cys Asn Asn Lys Thr Phe Asn Gly
        210                 215                 220

Thr Gly Pro Cys Asn Asn Val Ser Thr Val Gln Cys Thr His Gly Ile
225                 230                 235                 240

Met Pro Val Val Ser Thr Gln Leu Leu Leu Asn Gly Ser Leu Ala Glu
                245                 250                 255

Glu Glu Ile Ile Ile Arg Ser Glu Asn Leu Thr Asn Asn Ile Lys Thr
            260                 265                 270

Ile Ile Val His Leu Asn Lys Ser Val Glu Ile Val Cys Thr Arg Pro
        275                 280                 285

Asn Asn Asn Thr Arg Lys Ser Ile Arg Ile Gly Pro Gly Gln Thr Phe
        290                 295                 300

Tyr Ala Thr Gly Glu Ile Ile Gly Asn Ile Arg Glu Ala His Cys Asn
305                 310                 315                 320

Ile Ser Lys Ser Asn Trp Thr Ser Thr Leu Glu Gln Val Lys Lys Lys
                325                 330                 335

Leu Lys Glu His Tyr Asn Lys Thr Ile Glu Phe Asn Pro Pro Ser Gly
            340                 345                 350

Gly Asp Leu Glu Val Thr Thr His Ser Phe Asn Cys Arg Gly Glu Phe
        355                 360                 365

Phe Tyr Cys Asn Thr Thr Lys Leu Phe Ser Asn Asn Ser Asp Ser Asn
        370                 375                 380

Asn Glu Thr Ile Thr Leu Pro Cys Lys Ile Lys Gln Ile Ile Asn Met
385                 390                 395                 400

Trp Gln Lys Val Gly Arg Ala Met Tyr Ala Pro Pro Ile Glu Gly Asn
                405                 410                 415

Ile Thr Cys Lys Ser Asn Ile Thr Gly Leu Leu Leu Thr Arg Asp Gly
            420                 425                 430

Gly Lys Asn Thr Thr Asn Glu Ile Phe Arg Pro Gly Gly Gly Asn Met
        435                 440                 445

Lys Asp Asn Trp Arg Ser Glu Leu Tyr Lys Tyr Lys Val Val Glu Ile
        450                 455                 460

Glu Pro Leu Gly Val Ala Pro Thr Lys Ser Lys Arg Arg Val Val Glu
465                 470                 475                 480

Gly Gly Gly Gly Ser Gly Gly Gly Ser Ala Val Gly Leu Gly Ala
                485                 490                 495

Val Leu Leu Gly Phe Leu Gly Ala Ala Gly Ser Thr Met Gly Ala Ala
            500                 505                 510

Ser Ile Thr Leu Thr Val Gln Ala Arg Gln Leu Leu Ser Gly Ile Val
        515                 520                 525

Gln Gln Gln Ser Asn Leu Leu Arg Ala Pro Glu Ala Gln Gln His Met
        530                 535                 540

Leu Gln Leu Thr Val Trp Gly Ile Lys Gln Leu Gln Thr Arg Val Leu
545                 550                 555                 560

Ala Ile Glu Arg Tyr Leu Lys Asp Gln Gln Leu Leu Gly Leu Trp Gly
                565                 570                 575

Cys Ser Gly Lys Ile Ile Cys Thr Thr Ala Val Pro Trp Asn Ser Ser
            580                 585                 590

Trp Ser Asn Lys Ser Gln Glu Asp Ile Trp Asp Asn Met Thr Trp Met
        595                 600                 605
```

```
Gln Trp Asp Arg Glu Ile Ser Asn Tyr Thr Gly Thr Ile Tyr Arg Leu
            610                 615                 620
Leu Glu Asp Ser Gln Asn Gln Gln Glu Lys Asn Glu Lys Asp Leu Leu
625                 630                 635                 640
Ala Leu Asp Ala Ala Ala
                645

<210> SEQ ID NO 9
<211> LENGTH: 699
<212> TYPE: PRT
<213> ORGANISM: Artificial
<220> FEATURE:
<223> OTHER INFORMATION: Du151 Gp140FL fused to truncated HA2 of
      influenza

<400> SEQUENCE: 9

Met Glu Trp Ser Trp Ile Phe Leu Phe Leu Leu Ser Gly Thr Ala Gly
1               5                   10                  15
Val His Ser Ser Gly Val Gly Asn Leu Asn Leu Trp Val Thr Val Tyr
                20                  25                  30
Tyr Gly Val Pro Val Trp Lys Glu Ala Lys Thr Thr Leu Phe Cys Ala
            35                  40                  45
Ser Asp Ala Lys Ala Tyr Asp Lys Glu Val His Asn Val Trp Ala Thr
50                  55                  60
His Ala Cys Val Pro Thr Asp Pro Asn Pro Arg Glu Ile Val Leu Glu
65                  70                  75                  80
Asn Val Thr Glu Asn Phe Asn Met Trp Lys Asn Asp Met Val Asp Gln
                85                  90                  95
Met His Glu Asp Ile Ile Ser Leu Trp Asp Gln Ser Leu Lys Pro Cys
            100                 105                 110
Val Lys Leu Thr Pro Leu Cys Val Thr Leu Asn Cys Thr Asn Ala Pro
            115                 120                 125
Ala Tyr Asn Asn Ser Met His Gly Glu Met Lys Asn Cys Ser Phe Asn
130                 135                 140
Thr Thr Thr Glu Ile Arg Asp Arg Lys Gln Lys Ala Tyr Ala Leu Phe
145                 150                 155                 160
Tyr Lys Pro Asp Val Val Pro Leu Asn Arg Arg Glu Glu Asn Asn Gly
                165                 170                 175
Thr Gly Glu Tyr Ile Leu Ile Asn Cys Asn Ser Ser Thr Ile Thr Gln
            180                 185                 190
Ala Cys Pro Lys Val Thr Phe Asp Pro Ile Pro Ile His Tyr Cys Ala
            195                 200                 205
Pro Ala Gly Tyr Ala Ile Leu Lys Cys Asn Asn Lys Thr Phe Asn Gly
210                 215                 220
Thr Gly Pro Cys Asn Asn Val Ser Thr Val Gln Cys Thr His Gly Ile
225                 230                 235                 240
Met Pro Val Val Ser Thr Gln Leu Leu Leu Asn Gly Ser Leu Ala Glu
                245                 250                 255
Glu Glu Ile Ile Ile Arg Ser Glu Asn Leu Thr Asn Asn Ile Lys Thr
            260                 265                 270
Ile Ile Val His Leu Asn Lys Ser Val Glu Ile Val Cys Thr Arg Pro
            275                 280                 285
Asn Asn Asn Thr Arg Lys Ser Ile Arg Ile Gly Pro Gly Gln Thr Phe
290                 295                 300
Tyr Ala Thr Gly Glu Ile Ile Gly Asn Ile Arg Glu Ala His Cys Asn
305                 310                 315                 320
```

```
Ile Ser Lys Ser Asn Trp Thr Ser Thr Leu Glu Gln Val Lys Lys Lys
            325                 330                 335

Leu Lys Glu His Tyr Asn Lys Thr Ile Glu Phe Asn Pro Pro Ser Gly
            340                 345                 350

Gly Asp Leu Glu Val Thr Thr His Ser Phe Asn Cys Arg Gly Glu Phe
            355                 360                 365

Phe Tyr Cys Asn Thr Thr Lys Leu Phe Ser Asn Asn Ser Asp Ser Asn
            370                 375                 380

Asn Glu Thr Ile Thr Leu Pro Cys Lys Ile Lys Gln Ile Ile Asn Met
385                 390                 395                 400

Trp Gln Lys Val Gly Arg Ala Met Tyr Ala Pro Pro Ile Glu Gly Asn
            405                 410                 415

Ile Thr Cys Lys Ser Asn Ile Thr Gly Leu Leu Leu Thr Arg Asp Gly
            420                 425                 430

Gly Lys Asn Thr Thr Asn Glu Ile Phe Arg Pro Gly Gly Gly Asn Met
            435                 440                 445

Lys Asp Asn Trp Arg Ser Glu Leu Tyr Lys Tyr Lys Val Val Glu Ile
            450                 455                 460

Glu Pro Leu Gly Val Ala Pro Thr Lys Ser Lys Arg Arg Val Val Glu
465                 470                 475                 480

Gly Gly Gly Gly Ser Gly Gly Gly Ser Ala Val Gly Leu Gly Ala
            485                 490                 495

Val Leu Leu Gly Phe Leu Gly Ala Ala Gly Ser Thr Met Gly Ala Ala
            500                 505                 510

Ser Ile Thr Leu Thr Val Gln Ala Arg Gln Leu Leu Ser Gly Ile Val
            515                 520                 525

Gln Gln Gln Ser Asn Leu Leu Arg Ala Pro Glu Ala Gln Gln His Met
            530                 535                 540

Leu Gln Leu Thr Val Trp Gly Ile Lys Gln Leu Gln Thr Arg Val Leu
545                 550                 555                 560

Ala Ile Glu Arg Tyr Leu Lys Asp Gln Gln Leu Leu Gly Leu Trp Gly
            565                 570                 575

Cys Ser Gly Lys Ile Ile Cys Thr Thr Ala Val Pro Trp Asn Ser Ser
            580                 585                 590

Trp Ser Asn Lys Ser Gln Glu Asp Ile Trp Asp Asn Met Thr Trp Met
            595                 600                 605

Gln Trp Asp Arg Glu Ile Ser Asn Tyr Thr Gly Thr Ile Tyr Arg Leu
            610                 615                 620

Leu Glu Asp Ser Gln Asn Gln Gln Glu Lys Asn Glu Lys Asp Leu Leu
625                 630                 635                 640

Ala Leu Asp Ser Trp Lys Asn Leu Trp Asn Trp Phe Asn Ile Thr Asn
            645                 650                 655

Trp Leu Trp Tyr Ile Gln Ile Leu Ser Ile Tyr Ser Thr Val Ala Ser
            660                 665                 670

Ser Leu Ala Leu Ala Ile Met Val Ala Gly Leu Ser Leu Trp Met Cys
            675                 680                 685

Ser Asn Gly Ser Leu Gln Cys Arg Ala Ala Ala
            690                 695

<210> SEQ ID NO 10
<211> LENGTH: 702
<212> TYPE: PRT
<213> ORGANISM: Artificial
<220> FEATURE:
```

<223> OTHER INFORMATION: Du151 Gp120FL fused to HA2 of influenza

<400> SEQUENCE: 10

```
Met Glu Trp Ser Trp Ile Phe Leu Phe Leu Leu Ser Gly Thr Ala Gly
1               5                   10                  15

Val His Ser Ser Gly Val Gly Asn Leu Asn Leu Trp Val Thr Val Tyr
            20                  25                  30

Tyr Gly Val Pro Val Trp Lys Glu Ala Lys Thr Thr Leu Phe Cys Ala
        35                  40                  45

Ser Asp Ala Lys Ala Tyr Asp Lys Glu Val His Asn Val Trp Ala Thr
    50                  55                  60

His Ala Cys Val Pro Thr Asp Pro Asn Pro Arg Glu Ile Val Leu Glu
65                  70                  75                  80

Asn Val Thr Glu Asn Phe Asn Met Trp Lys Asn Asp Met Val Asp Gln
                85                  90                  95

Met His Glu Asp Ile Ile Ser Leu Trp Asp Gln Ser Leu Lys Pro Cys
            100                 105                 110

Val Lys Leu Thr Pro Leu Cys Val Thr Leu Asn Cys Thr Asn Ala Pro
        115                 120                 125

Ala Tyr Asn Asn Ser Met His Gly Glu Met Lys Asn Cys Ser Phe Asn
    130                 135                 140

Thr Thr Thr Glu Ile Arg Asp Arg Lys Gln Lys Ala Tyr Ala Leu Phe
145                 150                 155                 160

Tyr Lys Pro Asp Val Val Pro Leu Asn Arg Arg Glu Glu Asn Asn Gly
                165                 170                 175

Thr Gly Glu Tyr Ile Leu Ile Asn Cys Asn Ser Ser Thr Ile Thr Gln
            180                 185                 190

Ala Cys Pro Lys Val Thr Phe Asp Pro Ile Pro Ile His Tyr Cys Ala
        195                 200                 205

Pro Ala Gly Tyr Ala Ile Leu Lys Cys Asn Asn Lys Thr Phe Asn Gly
    210                 215                 220

Thr Gly Pro Cys Asn Asn Val Ser Thr Val Gln Cys Thr His Gly Ile
225                 230                 235                 240

Met Pro Val Val Ser Thr Gln Leu Leu Leu Asn Gly Ser Leu Ala Glu
                245                 250                 255

Glu Glu Ile Ile Ile Arg Ser Glu Asn Leu Thr Asn Asn Ile Lys Thr
            260                 265                 270

Ile Ile Val His Leu Asn Lys Ser Val Glu Ile Val Cys Thr Arg Pro
        275                 280                 285

Asn Asn Asn Thr Arg Lys Ser Ile Arg Ile Gly Pro Gly Gln Thr Phe
    290                 295                 300

Tyr Ala Thr Gly Glu Ile Ile Gly Asn Ile Arg Glu Ala His Cys Asn
305                 310                 315                 320

Ile Ser Lys Ser Asn Trp Thr Ser Thr Leu Glu Gln Val Lys Lys Lys
                325                 330                 335

Leu Lys Glu His Tyr Asn Lys Thr Ile Glu Phe Asn Pro Pro Ser Gly
            340                 345                 350

Gly Asp Leu Glu Val Thr Thr His Ser Phe Asn Cys Arg Gly Glu Phe
        355                 360                 365

Phe Tyr Cys Asn Thr Thr Lys Leu Phe Ser Asn Asn Ser Asp Ser Asn
    370                 375                 380

Asn Glu Thr Ile Thr Leu Pro Cys Lys Ile Lys Gln Ile Ile Asn Met
385                 390                 395                 400
```

```
Trp Gln Lys Val Gly Arg Ala Met Tyr Ala Pro Pro Ile Glu Gly Asn
            405                 410                 415

Ile Thr Cys Lys Ser Asn Ile Thr Gly Leu Leu Leu Thr Arg Asp Gly
        420                 425                 430

Gly Lys Asn Thr Thr Asn Glu Ile Phe Arg Pro Gly Gly Gly Asn Met
    435                 440                 445

Lys Asp Asn Trp Arg Ser Glu Leu Tyr Lys Tyr Lys Val Val Glu Ile
450                 455                 460

Glu Pro Leu Gly Val Ala Pro Thr Lys Ser Lys Arg Arg Val Val Glu
465                 470                 475                 480

Gly Gly Gly Gly Ser Gly Gly Gly Ser Glu Gly Gly Trp Gln Gly
                485                 490                 495

Met Val Asp Gly Trp Tyr Gly Tyr His His Ser Asn Glu Gln Gly Ser
                500                 505                 510

Gly Tyr Ala Ala Asp Lys Glu Ser Thr Gln Lys Ala Ile Asp Gly Val
            515                 520                 525

Thr Asn Lys Val Asn Ser Ile Ile Asp Lys Met Asn Thr Gln Phe Glu
        530                 535                 540

Ala Val Gly Arg Glu Phe Asn Asn Leu Glu Arg Arg Ile Glu Asn Leu
545                 550                 555                 560

Asn Lys Lys Met Glu Asp Gly Phe Leu Asp Val Trp Thr Tyr Asn Ala
                565                 570                 575

Glu Leu Leu Val Leu Met Glu Asn Glu Arg Thr Leu Asp Phe His Asp
                580                 585                 590

Ser Asn Val Lys Asn Leu Tyr Asp Lys Val Arg Leu Gln Leu Arg Asp
            595                 600                 605

Asn Ala Lys Glu Leu Gly Asn Gly Cys Phe Glu Phe Tyr His Lys Cys
610                 615                 620

Asp Asn Glu Cys Met Glu Ser Val Arg Asn Gly Thr Tyr Asp Tyr Pro
625                 630                 635                 640

Gln Tyr Ser Glu Glu Ala Arg Leu Lys Arg Glu Glu Ile Ser Gly Val
                645                 650                 655

Lys Leu Glu Ser Ile Gly Ile Tyr Gln Ile Leu Ser Ile Tyr Ser Thr
                660                 665                 670

Val Ala Ser Ser Leu Ala Leu Ala Ile Met Val Ala Gly Leu Ser Leu
            675                 680                 685

Trp Met Cys Ser Asn Gly Ser Leu Gln Cys Arg Ala Ala
        690                 695                 700

<210> SEQ ID NO 11
<211> LENGTH: 725
<212> TYPE: PRT
<213> ORGANISM: Artificial
<220> FEATURE:
<223> OTHER INFORMATION: Du151 Gp150FL

<400> SEQUENCE: 11

Met Glu Trp Ser Trp Ile Phe Leu Phe Leu Leu Ser Gly Thr Ala Gly
1               5                   10                  15

Val His Ser Ser Gly Val Gly Asn Leu Asn Leu Trp Val Thr Val Tyr
            20                  25                  30

Tyr Gly Val Pro Val Trp Lys Glu Ala Lys Thr Thr Leu Phe Cys Ala
        35                  40                  45

Ser Asp Ala Lys Ala Tyr Asp Lys Glu Val His Asn Val Trp Ala Thr
50                  55                  60
```

```
His Ala Cys Val Pro Thr Asp Pro Asn Pro Arg Glu Ile Val Leu Glu
 65                  70                  75                  80

Asn Val Thr Glu Asn Phe Asn Met Trp Lys Asn Asp Met Val Asp Gln
                 85                  90                  95

Met His Glu Asp Ile Ile Ser Leu Trp Asp Gln Ser Leu Lys Pro Cys
            100                 105                 110

Val Lys Leu Thr Pro Leu Cys Val Thr Leu Asn Cys Thr Asn Ala Pro
        115                 120                 125

Ala Tyr Asn Asn Ser Met His Gly Glu Met Lys Asn Cys Ser Phe Asn
    130                 135                 140

Thr Thr Thr Glu Ile Arg Asp Arg Lys Gln Lys Ala Tyr Ala Leu Phe
145                 150                 155                 160

Tyr Lys Pro Asp Val Val Pro Leu Asn Arg Arg Glu Glu Asn Asn Gly
                165                 170                 175

Thr Gly Glu Tyr Ile Leu Ile Asn Cys Asn Ser Ser Thr Ile Thr Gln
            180                 185                 190

Ala Cys Pro Lys Val Thr Phe Asp Pro Ile Pro Ile His Tyr Cys Ala
        195                 200                 205

Pro Ala Gly Tyr Ala Ile Leu Lys Cys Asn Asn Lys Thr Phe Asn Gly
    210                 215                 220

Thr Gly Pro Cys Asn Asn Val Ser Thr Val Gln Cys Thr His Gly Ile
225                 230                 235                 240

Met Pro Val Val Ser Thr Gln Leu Leu Leu Asn Gly Ser Leu Ala Glu
                245                 250                 255

Glu Glu Ile Ile Ile Arg Ser Glu Asn Leu Thr Asn Asn Ile Lys Thr
            260                 265                 270

Ile Ile Val His Leu Asn Lys Ser Val Glu Ile Val Cys Thr Arg Pro
        275                 280                 285

Asn Asn Asn Thr Arg Lys Ser Ile Arg Ile Gly Pro Gly Gln Thr Phe
    290                 295                 300

Tyr Ala Thr Gly Glu Ile Ile Gly Asn Ile Arg Glu Ala His Cys Asn
305                 310                 315                 320

Ile Ser Lys Ser Asn Trp Thr Ser Thr Leu Glu Gln Val Lys Lys Lys
                325                 330                 335

Leu Lys Glu His Tyr Asn Lys Thr Ile Glu Phe Asn Pro Pro Ser Gly
            340                 345                 350

Gly Asp Leu Glu Val Thr Thr His Ser Phe Asn Cys Arg Gly Glu Phe
        355                 360                 365

Phe Tyr Cys Asn Thr Thr Lys Leu Phe Ser Asn Asn Ser Asp Ser Asn
    370                 375                 380

Asn Glu Thr Ile Thr Leu Pro Cys Lys Ile Lys Gln Ile Ile Asn Met
385                 390                 395                 400

Trp Gln Lys Val Gly Arg Ala Met Tyr Ala Pro Pro Ile Glu Gly Asn
                405                 410                 415

Ile Thr Cys Lys Ser Asn Ile Thr Gly Leu Leu Leu Thr Arg Asp Gly
            420                 425                 430

Gly Lys Asn Thr Thr Asn Glu Ile Phe Arg Pro Gly Gly Gly Asn Met
        435                 440                 445

Lys Asp Asn Trp Arg Ser Glu Leu Tyr Lys Tyr Lys Val Val Glu Ile
    450                 455                 460

Glu Pro Leu Gly Val Ala Pro Thr Lys Ser Lys Arg Arg Val Val Glu
465                 470                 475                 480

Gly Gly Gly Gly Ser Gly Gly Gly Gly Ser Ala Val Gly Leu Gly Ala
```

```
                   485                 490                 495
Val Leu Leu Gly Phe Leu Gly Ala Ala Gly Ser Thr Met Gly Ala Ala
                500                 505                 510

Ser Ile Thr Leu Thr Val Gln Ala Arg Gln Leu Leu Ser Gly Ile Val
            515                 520                 525

Gln Gln Gln Ser Asn Leu Leu Arg Ala Pro Glu Ala Gln Gln His Met
        530                 535                 540

Leu Gln Leu Thr Val Trp Gly Ile Lys Gln Leu Gln Thr Arg Val Leu
545                 550                 555                 560

Ala Ile Glu Arg Tyr Leu Lys Asp Gln Gln Leu Leu Gly Leu Trp Gly
                565                 570                 575

Cys Ser Gly Lys Ile Ile Cys Thr Thr Ala Val Pro Trp Asn Ser Ser
            580                 585                 590

Trp Ser Asn Lys Ser Gln Glu Asp Ile Trp Asp Asn Met Thr Trp Met
        595                 600                 605

Gln Trp Asp Arg Glu Ile Ser Asn Tyr Thr Gly Thr Ile Tyr Arg Leu
    610                 615                 620

Leu Glu Asp Ser Gln Asn Gln Gln Glu Lys Asn Glu Lys Asp Leu Leu
625                 630                 635                 640

Ala Leu Asp Ser Trp Lys Asn Leu Trp Asn Trp Phe Asn Ile Thr Asn
                645                 650                 655

Trp Leu Trp Tyr Ile Lys Ile Phe Ile Met Ile Val Gly Gly Leu Ile
            660                 665                 670

Gly Leu Arg Ile Ile Phe Gly Val Leu Ala Ile Val Lys Arg Val Arg
        675                 680                 685

Gln Gly Tyr Ser Pro Leu Ser Phe Gln Thr Leu Thr Pro Ser Pro Arg
    690                 695                 700

Gly Pro Asp Arg Leu Gly Arg Ile Glu Glu Glu Gly Gly Glu Gln Asp
705                 710                 715                 720

Lys Asp Ala Ala Ala
                725

<210> SEQ ID NO 12
<211> LENGTH: 842
<212> TYPE: PRT
<213> ORGANISM: Artificial
<220> FEATURE:
<223> OTHER INFORMATION: Du151 Gp160FL

<400> SEQUENCE: 12

Met Glu Trp Ser Trp Ile Phe Leu Phe Leu Leu Ser Gly Thr Ala Gly
1               5                   10                  15

Val His Ser Ser Gly Val Gly Asn Leu Asn Leu Trp Val Thr Val Tyr
            20                  25                  30

Tyr Gly Val Pro Val Trp Lys Glu Ala Lys Thr Thr Leu Phe Cys Ala
        35                  40                  45

Ser Asp Ala Lys Ala Tyr Asp Lys Glu Val His Asn Val Trp Ala Thr
    50                  55                  60

His Ala Cys Val Pro Thr Asp Pro Asn Pro Arg Glu Ile Val Leu Glu
65                  70                  75                  80

Asn Val Thr Glu Asn Phe Asn Met Trp Lys Asn Asp Met Val Asp Gln
                85                  90                  95

Met His Glu Asp Ile Ile Ser Leu Trp Asp Gln Ser Leu Lys Pro Cys
            100                 105                 110

Val Lys Leu Thr Pro Leu Cys Val Thr Leu Asn Cys Thr Asn Ala Pro
```

-continued

```
                115                 120                 125
Ala Tyr Asn Asn Ser Met His Gly Glu Met Lys Asn Cys Ser Phe Asn
        130                 135                 140
Thr Thr Thr Glu Ile Arg Asp Arg Lys Gln Lys Ala Tyr Ala Leu Phe
145                 150                 155                 160
Tyr Lys Pro Asp Val Val Pro Leu Asn Arg Glu Glu Asn Asn Gly
                165                 170                 175
Thr Gly Glu Tyr Ile Leu Ile Asn Cys Asn Ser Ser Thr Ile Thr Gln
                180                 185                 190
Ala Cys Pro Lys Val Thr Phe Asp Pro Ile Pro Ile His Tyr Cys Ala
                195                 200                 205
Pro Ala Gly Tyr Ala Ile Leu Lys Cys Asn Asn Lys Thr Phe Asn Gly
            210                 215                 220
Thr Gly Pro Cys Asn Asn Val Ser Thr Val Gln Cys Thr His Gly Ile
225                 230                 235                 240
Met Pro Val Val Ser Thr Gln Leu Leu Leu Asn Gly Ser Leu Ala Glu
                245                 250                 255
Glu Glu Ile Ile Ile Arg Ser Glu Asn Leu Thr Asn Asn Ile Lys Thr
                260                 265                 270
Ile Ile Val His Leu Asn Lys Ser Val Glu Ile Val Cys Thr Arg Pro
            275                 280                 285
Asn Asn Asn Thr Arg Lys Ser Ile Arg Ile Gly Pro Gly Gln Thr Phe
290                 295                 300
Tyr Ala Thr Gly Glu Ile Ile Gly Asn Ile Arg Glu Ala His Cys Asn
305                 310                 315                 320
Ile Ser Lys Ser Asn Trp Thr Ser Thr Leu Glu Gln Val Lys Lys Lys
                325                 330                 335
Leu Lys Glu His Tyr Asn Lys Thr Ile Glu Phe Asn Pro Pro Ser Gly
            340                 345                 350
Gly Asp Leu Glu Val Thr Thr His Ser Phe Asn Cys Arg Gly Glu Phe
            355                 360                 365
Phe Tyr Cys Asn Thr Thr Lys Leu Phe Ser Asn Asn Ser Asp Ser Asn
        370                 375                 380
Asn Glu Thr Ile Thr Leu Pro Cys Lys Ile Lys Gln Ile Ile Asn Met
385                 390                 395                 400
Trp Gln Lys Val Gly Arg Ala Met Tyr Ala Pro Pro Ile Glu Gly Asn
                405                 410                 415
Ile Thr Cys Lys Ser Asn Ile Thr Gly Leu Leu Leu Thr Arg Asp Gly
                420                 425                 430
Gly Lys Asn Thr Thr Asn Glu Ile Phe Arg Pro Gly Gly Gly Asn Met
            435                 440                 445
Lys Asp Asn Trp Arg Ser Glu Leu Tyr Lys Tyr Lys Val Val Glu Ile
        450                 455                 460
Glu Pro Leu Gly Val Ala Pro Thr Lys Ser Lys Arg Arg Val Val Glu
465                 470                 475                 480
Gly Gly Gly Gly Ser Gly Gly Gly Ser Ala Val Gly Leu Gly Ala
                485                 490                 495
Val Leu Leu Gly Phe Leu Gly Ala Ala Gly Ser Thr Met Gly Ala Ala
            500                 505                 510
Ser Ile Thr Leu Thr Val Gln Ala Arg Gln Leu Leu Ser Gly Ile Val
            515                 520                 525
Gln Gln Gln Ser Asn Leu Leu Arg Ala Pro Glu Ala Gln Gln His Met
        530                 535                 540
```

| | | | | | | | | | | | |
|---|---|---|---|---|---|---|---|---|---|---|---|
| Leu | Gln | Leu | Thr | Val | Trp | Gly | Ile | Lys | Gln | Leu | Gln | Thr | Arg | Val | Leu |
| 545 | | | | | 550 | | | | | 555 | | | | | 560 |

Leu Gln Leu Thr Val Trp Gly Ile Lys Gln Leu Gln Thr Arg Val Leu
545                 550                 555                 560

Ala Ile Glu Arg Tyr Leu Lys Asp Gln Gln Leu Leu Gly Leu Trp Gly
                565                 570                 575

Cys Ser Gly Lys Ile Ile Cys Thr Thr Ala Val Pro Trp Asn Ser Ser
            580                 585                 590

Trp Ser Asn Lys Ser Gln Glu Asp Ile Trp Asp Asn Met Thr Trp Met
        595                 600                 605

Gln Trp Asp Arg Glu Ile Ser Asn Tyr Thr Gly Thr Ile Tyr Arg Leu
    610                 615                 620

Leu Glu Asp Ser Gln Asn Gln Glu Lys Asn Glu Lys Asp Leu Leu
625                 630                 635                 640

Ala Leu Asp Ser Trp Lys Asn Leu Trp Asn Trp Phe Asn Ile Thr Asn
                645                 650                 655

Trp Leu Trp Tyr Ile Lys Ile Phe Ile Met Ile Val Gly Gly Leu Ile
            660                 665                 670

Gly Leu Arg Ile Ile Phe Gly Val Leu Ala Ile Val Lys Arg Val Arg
        675                 680                 685

Gln Gly Tyr Ser Pro Leu Ser Phe Gln Thr Leu Thr Pro Ser Pro Arg
    690                 695                 700

Gly Pro Asp Arg Leu Gly Arg Ile Glu Glu Gly Gly Glu Gln Asp
705                 710                 715                 720

Lys Asp Arg Ser Ile Arg Leu Val Ser Gly Phe Leu Ala Leu Ala Trp
                725                 730                 735

Asp Asp Leu Arg Ser Leu Cys Leu Phe Ser Tyr His His Leu Arg Asp
            740                 745                 750

Phe Ile Leu Ile Ala Ala Arg Ala Ala Glu Leu Leu Gly Arg Ser Ser
        755                 760                 765

Leu Arg Gly Leu Gln Arg Gly Trp Glu Ala Leu Lys Tyr Leu Gly Asn
    770                 775                 780

Leu Val Gln Tyr Gly Gly Leu Glu Leu Lys Arg Ser Ala Ile Lys Leu
785                 790                 795                 800

Phe Asp Thr Ile Ala Ile Ala Val Ala Glu Gly Thr Asp Arg Ile Leu
                805                 810                 815

Glu Val Ile Gln Arg Ile Cys Arg Ala Ile Arg His Ile Pro Ile Arg
            820                 825                 830

Ile Arg Gln Gly Phe Glu Ala Ala Leu Gln
        835                 840

<210> SEQ ID NO 13
<211> LENGTH: 1971
<212> TYPE: DNA
<213> ORGANISM: Artificial
<220> FEATURE:
<223> OTHER INFORMATION: CAP256SU Gp140NFL

<400> SEQUENCE: 13
atggagtggt cttggatctt cctgtttctg ctgagcggga ctgctggagt gcattcttcc     60
ggagggctgt gggtcactgt ctactatggc gtgcctgtct ggagagaggc caagaccaca    120
ctgttctgcg cttccgatgc aaagtcttac gaaaagagg tgcacaacgt ctgggccaca    180
catgcttgcg tgccaactga ccccaaccct caggaactgg tgctgaagaa tgtcaccgag    240
aactttaata tgtggaaaaa tgacatggtg atcagatgc acgaggatat cattagtctg    300
tgggaccagt cactgaagcc ctgcgtgaaa ctgacacctc tgtgcgtcac tctgaactgt    360

| | | | | |
|---|---|---|---|---|
| agcgatgcaa | aggtgaacat | taatgccaca | tacaatggca | ctcgcgagga aatcaaaaac | 420 |
| tgttccttca | atgcaactac | cgaactgagg | acaagaaga | agaaggagta cgccctgttt | 480 |
| tatcgcctgg | acatcgtgcc | cctgaacaag | gaagggaaca | ataacagtga gtatcggctg | 540 |
| attaactgca | ataccagcgt | gattacccag | gcctgtccta | aagtcacctt cgatccaatt | 600 |
| cccatccact | actgcgcacc | agccggatat | gctattctga | agtgtaacaa caaaactttt | 660 |
| aacgggaccg | accctgcaa | taacgtgtct | acagtccagt | gtactcatgg catcaagcct | 720 |
| gtggtctcaa | cccagctgct | gctgaatggg | agcctggccg | aggaagagat cattatcaga | 780 |
| agcgagaacc | tgaccgacaa | tgtgaagaca | attatcgtcc | acctgaacga atccgtggag | 840 |
| attaattgca | ccaggccaaa | caacaacaca | cgaaaatcta | ttcggatcgg accaggacag | 900 |
| accttctacg | caacagggga | cattatcgga | gatatcaggc | aggctcattg taacatttct | 960 |
| gaaatcaagt | gggagaaaac | cctgcagcgc | gtgagtgaaa | agctgcgaga gcacttcaac | 1020 |
| aaaacaatca | tctttaatca | gagctccggc | ggggacctgg | aaatcacaac tcattcattc | 1080 |
| aactgcggag | gcgagttctt | ttactgtaac | actagcgatc | tgttctttaa taagaccttt | 1140 |
| gacgagacct | attccacagg | ctcaaacagc | actaattcta | ccattacact gccatgccga | 1200 |
| atcaaacaga | ttatcaacat | gtggcaggaa | gtgggccggg | caatgtatgc cagccccatt | 1260 |
| gccggagaga | tcacctgtaa | gtccaatatc | actggactgc | tgctgaccag agatggggga | 1320 |
| ggcaacaatt | ctactgaaga | gacctttagg | cccggggag | gcaacatgag agacaattgg | 1380 |
| aggagcgaac | tgtacaagta | taaagtggtc | gaggtgaagc | ctctgggaat cgcaccaacc | 1440 |
| gaggcccgga | gaagggtggt | ccagcagggc | ggtggaggct | caggtggagg cggatccgct | 1500 |
| gtggtcggac | tggagcagt | gttcctgggg | tttctgggaa | ctgctggcag caccatggga | 1560 |
| gccgcttcca | ttactctgac | cgtgcaggca | cgccagctgc | tgtctggcat cgtccagcag | 1620 |
| cagagtaacc | tgctgcgggc | tcctgaagca | cagcagcata | tgctgcagct gaccgtgtgg | 1680 |
| gggattaagc | agctgcaggc | ccgggtcctg | gctatcgaga | gatacctgaa ggatcagcag | 1740 |
| ctgctgggga | tgtggggatg | cagtggcaaa | ctgatttgca | ccacaaacgt gtactggaac | 1800 |
| agcagctggt | ccaacaagac | atataatgaa | atctgggaca | catgacttg gatgcagtgg | 1860 |
| gaccgcgaga | tcgataacta | cacagacact | atctataaac | tgctggaagt ctcacagaaa | 1920 |
| cagcaggagt | caaatgaaaa | ggacctgctg | gcactggatg | cggccgcatg a | 1971 |

<210> SEQ ID NO 14
<211> LENGTH: 2073
<212> TYPE: DNA
<213> ORGANISM: Artificial
<220> FEATURE:
<223> OTHER INFORMATION: CAP256SU Gp140FL fused to HA2 of influenza

<400> SEQUENCE: 14

| | | | | |
|---|---|---|---|---|
| atggagtggt | cttggatctt | cctgtttctg | ctgagcggga | ctgctggagt gcattcttcc | 60 |
| ggagggctgt | gggtcactgt | ctactatggc | gtgcctgtct | ggagagaggc caagaccaca | 120 |
| ctgttctgcg | cttccgatgc | aaagtcttac | gaaaagagg | tgcacaacgt ctgggccaca | 180 |
| catgcttgcg | tgccaactga | ccccaacct | caggaactgg | tgctgaagaa tgtcaccgag | 240 |
| aactttaata | tgtggaaaaa | tgacatggtg | gatcagatgc | acgaggatat cattagtctg | 300 |
| tgggaccagt | cactgaagcc | ctgcgtgaaa | ctgacacctc | tgtgcgtcac tctgaactgt | 360 |
| agcgatgcaa | aggtgaacat | taatgccaca | tacaatggca | ctcgcgagga aatcaaaaac | 420 |

```
tgttccttca atgcaactac cgaactgagg gacaagaaga agaaggagta cgccctgttt    480
tatcgcctgg acatcgtgcc cctgaacaag gaagggaaca ataacagtga gtatcggctg    540
attaactgca ataccagcgt gattacccag gcctgtccta agtcacctt cgatccaatt     600 cccatccact actgcgcacc agccggatat gctattctga agtgtaacaa caaaactttt    660
aacgggaccg gaccctgcaa taacgtgtct acagtccagt gtactcatgg catcaagcct    720
gtggtctcaa cccagctgct gctgaatggg agcctggccg aggaagagat cattatcaga    780
agcgagaacc tgaccgacaa tgtgaagaca attatcgtcc acctgaacga atccgtggag    840
attaattgca ccaggccaaa caacaacaca cgaaaatcta ttcggatcgg accaggacag    900
accttctacg caacagggga cattatcgga gatatcaggc aggctcattg taacatttct    960
gaaatcaagt gggagaaaac cctgcagcgc gtgagtgaaa agctgcgaga gcacttcaac   1020
aaaacaatca tctttaatca gagctccggc ggggacctgg aaatcacaac tcattcattc   1080
aactgcggag cgagttcttt tactgtaac actagcgatc tgttctttaa taagaccttt    1140
gacgagacct attccacagg ctcaaacagc actaattcta ccattacact gccatgccga   1200
atcaaacaga ttatcaacat gtggcaggaa gtgggccggg caatgtatgc cagccccatt   1260
gccgagagaa tcacctgtaa gtccaatatc actggactgc tgctgaccag agatggggga   1320
ggcaacaatt ctactgaaga gacctttagg cccggggag gcaacatgag agacaattgg    1380
aggagcgaac tgtacaagta taagtggtc gaggtgaagc ctctgggaat cgcaccaacc    1440
gaggcccgga aagggtggt ccagcagggc ggtggaggct caggtggagg cggatccgct    1500
gtggtcggac tgggagcagt gttcctgggg tttctgggaa ctgctggcag caccatggga   1560
gccgcttcca ttactctgac cgtgcaggca cgccagctgc tgtctggcat cgtccagcag   1620
cagagtaacc tgctgcgggc tcctgaagca gcagcagcata tgctgcagct gaccgtgtgg   1680
gggattaagc agctgcaggc ccgggtcctg gctatcgaga gatacctgaa ggatcagcag    1740
ctgctgggga tgtggggatg cagtggcaaa ctgatttgca ccacaaacgt gtactggaac   1800
agcagctggt ccaacaagac atataatgaa atctgggaca catgacttg gatgcagtgg    1860 gaccgcgaga tcgataacta cacagacact atctataaac tgctggaagt ctcacagaaa    1920
cagcaggagt caaatgaaaa ggacctgctg gcactggata gctggaacaa tctgtggaat    1980
tggttcgata tttccaagtg gctgtggtac attcagatcc tgagtatcta ttcaaccgtg    2040
gcttcaagcc tggctctggc aattatggtc gca                                 2073
```

<210> SEQ ID NO 15
<211> LENGTH: 2136
<212> TYPE: DNA
<213> ORGANISM: Artificial
<220> FEATURE:
<223> OTHER INFORMATION: CAP256SU Gp120FL fused to HA2 of influenza

<400> SEQUENCE: 15

```
atggagtggt cttggatctt cctgtttctg ctgagcggga ctgctggagt gcattcttcc     60
ggagggctgt gggtcactgt ctactatggc gtgcctgtct ggagagaggc caagaccaca   120
ctgttctgcg cttccgatgc aaagtcttac gaaaaagagg tgcacaacgt ctgggccaca   180
catgcttgcg tgccaactga ccccaaccct caggaactgg tgctgaagaa tgtcaccgag   240
aactttaata tgtggaaaaa tgacatggtg gatcagatgc acgaggatat cattagtctg   300
tgggaccagt cactgaagcc ctgcgtgaaa ctgacacctc tgtgcgtcac tctgaactgt    360
agcgatgcaa aggtgaacat taatgccaca tacaatgcca ctcgcgagga aatcaaaaac    420
```

```
tgttccttca atgcaactac cgaactgagg gacaagaaga agaaggagta cgccctgttt      480
tatcgcctgg acatcgtgcc cctgaacaag gaagggaaca taacagtga gtatcggctg      540 attaactgca ataccagcgt gattacccag gcctgtccta aagtcacctt cgatccaatt     600
cccatccact actgcgcacc agccggatat gctattctga agtgtaacaa caaaactttt     660
aacgggaccg gaccctgcaa taacgtgtct acagtccagt gtactcatgg catcaagcct    720
gtggtctcaa cccagctgct gctgaatggg agcctggccg aggaagagat cattatcaga    780
agcgagaacc tgaccgacaa tgtgaagaca attatcgtcc acctgaacga atccgtggag    840
attaattgca ccaggccaaa caacaacaca cgaaaatcta ttcggatcgg accaggacag    900
accttctacg caacagggga cattatcgga gatatcaggc aggctcattg taacatttct   960
gaaatcaagt gggagaaaac cctgcagcgc gtgagtgaaa agctgcgaga gcacttcaac    1020
aaaacaatca tctttaatca gagctccggc ggggacctgg aaatcacaac tcattcattc    1080
aactgcggag gcgagttctt ttactgtaac actagcgatc tgttctttaa taagaccttt    1140
gacgagacct attccacagg ctcaaacagc actaattcta ccattacact gccatgccga    1200
atcaaacaga ttatcaacat gtggcaggaa gtgggccggg caatgtatgc cagccccatt   1260
gccggagaga tcacctgtaa gtccaatatc actggactgc tgctgaccag agatggggga   1320
ggcaacaatt ctactgaaga gacctttagg cccgggggag gcaacatgag agacaattgg    1380
aggagcgaac tgtacaagta taaagtggtc gaggtgaagc ctctgggaat cgcaccaacc    1440
gaggcccgga aagggtggt ccagcagggc ggtggaggct caggtggagg cggatccgag     1500
gggggatggc agggaatggt ggacgggtgg tacggatatc accattcaaa cgaacagggg   1560
agcggatatg ccgctgacaa ggagtctaca cagaaagcaa tcgatggggt gactaacaag   1620
gtcaatagta tcatcgataa gatgaatacc cagttcgaag ccgtgggacg cgagtttaac    1680
aatctggaac gccgaatcga gaacctgaat aagaaaatgg aagacggctt cctggatgtg   1740 tggaccctaca acgctgagct gctggtcctg atggaaaatg agcggacact ggactttcac   1800
gatagcaacg tgaagaatct gtatgacaaa gtcagactgc agctgaggga taacgccaag   1860
gaactgggca atgggtgctt cgagttttac cataaatgcg acaacgaatg tatggagagt   1920
gtgcgcaatg gcacctacga ttatcctcag tattcagaag aggcccggct gaagagagaa    1980
gagattagcg gcgtgaaact ggagtctatt ggcatctacc agatcctgag tatctattca    2040
accgtggctt caagcctggc tctggcaatt atggtcgcag gcctgtctct gtggatgtgc   2100
agcaacgggt ccctgcagtg tcgagcggcc gcatga                             2136
```

<210> SEQ ID NO 16
<211> LENGTH: 2208
<212> TYPE: DNA
<213> ORGANISM: Artificial
<220> FEATURE:
<223> OTHER INFORMATION: CAP256SU Gp150FL

<400> SEQUENCE: 16

```
atggagtggt cttggatctt cctgtttctg ctgagcggga ctgctggagt gcattcttcc    60
ggagggctgt gggtcactgt ctactatggc gtgcctgtct ggagagaggc caagaccaca   120
ctgttctgcg cttccgatgc aaagtcttac gaaaagagg tgcacaacgt ctgggccaca    180
catgcttgcg tgccaactga ccccaaccct caggaactgg tgctgaagaa tgtcaccgag   240
aactttaata tgtggaaaaa tgacatggtg atcagatgca cgaggatat cattagtctg    300
```

```
tgggaccagt cactgaagcc ctgcgtgaaa ctgacacctc tgtgcgtcac tctgaactgt      360
agcgatgcaa aggtgaacat taatgccaca tacaatggca ctcgcgagga aatcaaaaac      420
tgttccttca atgcaactac cgaactgagg gacaagaaga agaaggagta cgccctgttt      480
tatcgcctgg acatcgtgcc cctgaacaag gaagggaaca taacagtgaa gtatcggctg      540
attaactgca ataccagcgt gattacccag gcctgtccta agtcaccttc gatccaatt      600 cccatccact actgcgcacc agccggatat gctattctga agtgtaacaa caaaactttt      660
aacgggaccg gaccctgcaa taacgtgtct acagtccagt gtactcatgg catcaagcct      720
gtggtctcaa cccagctgct gctgaatggg agcctggccg aggaagagat cattatcaga      780
agcgagaacc tgaccgacaa tgtgaagaca attatcgtcc acctgaacga atccgtggag      840
attaattgca ccaggccaaa caacaacaca cgaaaatcta ttcggatcgg accaggacag      900
accttctacg caacagggga cattatcgga gatatcaggc aggctcattg taacatttct      960
gaaatcaagt gggagaaaac cctgcagcgc gtgagtgaaa agctgcgaga gcacttcaac      1020
aaaacaatca tctttaatca gagctccggc ggggacctgg aaatcacaac tcattcattc      1080
aactgcggag gcgagttctt ttactgtaac actagcgatc tgttctttaa taagaccttt      1140
gacgagacct attccacagg ctcaaacagc actaattcta ccattacact gccatgccga      1200
atcaaacaga ttatcaacat gtggcaggaa gtgggccggg caatgtatgc cagccccatt      1260
gccgagagat cacctgtaa gtccaatatc actggactgc tgctgaccag agatggggga      1320
ggcaacaatt ctactgaaga gacctttagg cccggggag gcaacatgag agacaattgg      1380
aggagcgaac tgtacaagta taaagtggtc gaggtgaagc ctctgggaat cgcaccaacc      1440
gaggcccgga aagggtggt ccagcagggc ggtggaggct caggtggagg cggatccgct      1500 gtggtcgac tgggagcagt gttcctgggg tttctgggaa ctgctggcag caccatggga      1560
gccgcttcca ttactctgac cgtgcaggca cgccagctgc tgtctggcat cgtccagcag      1620
cagagtaacc tgctgcgggc tcctgaagca cagcagcata tgctgcagct gaccgtgtgg      1680
gggattaagc agctgcaggc ccgggtcctg gctatcgaga gatacctgaa ggatcagcag      1740
ctgctgggga tgtggggatg cagtggcaaa ctgatttgca ccacaaacgt gtactggaac      1800
agcagctggt ccaacaagac atataatgaa atctgggaca catgacttg gatgcagtgg      1860 gaccgcgaga tcgataacta cacagacact atctataaac tgctggaagt ctcacagaaa      1920
cagcaggagt caaatgaaaa ggacctgctg gcactggata gctggaacaa tctgtggaat      1980
tggttcgata tttccaagtg ctgtggtac attaagatct tcatcatgat cgtgggggga      2040
ctgatcgggc tgcgcattat cttcgcagtg ctgagcctgg tgaaccgcgt ccgacaggga      2100
tattcccccc tgtctttttca gactctgacc cctaatccac gagaactgga ccggctgggc      2160
gggatcgaag aggaaggagg cgagcaggac cgggatgcgg ccgcatga                  2208
```

<210> SEQ ID NO 17
<211> LENGTH: 1941
<212> TYPE: DNA
<213> ORGANISM: Artificial
<220> FEATURE:
<223> OTHER INFORMATION: Du151 Gp140NFL

<400> SEQUENCE: 17

```
atggagtggt cttggatctt cctgttcctg ctgtctggga ctgctggagt gcatagttcc       60
ggagtcggca acctgaatct gtgggtgacc gtgtactatg gcgtgcccgt ctggaaagaa      120
gcaaagacca cactgttttg cgccagcgac gctaaagcat acgataagga ggtgcacaat      180
```

```
gtctgggcca cacatgcttg tgtgcctact gaccctaatc cacgggagat cgtgctggaa      240
aacgtcactg agaatttcaa catgtggaag aacgacatgg tggatcagat gcacgaggac      300
atcatttctc tgtgggatca gagtctgaaa ccatgcgtga agctgacccc cctgtgcgtc      360
acactgaatt gtactaacgc ccctgcttac aacaatagca tgcatgggga aatgaagaac      420
tgttccttta cactaccac agagatccga gaccggaaac agaaggcata cgccctgttc       480
tataagcctg atgtggtccc actgaaccgg agagaggaaa caatggaac aggcgagtat       540 attctgatta actgcaacag ctccacaatt actcaggcct gtccaaaagt gacttttgat      600
cccattccta tccactactg cgctcccgca ggctatgcta tcctgaaatg taacaataag      660
accttcaatg gacaggacc ttgcaacaat gtgagcactg tccagtgtac ccatgggatc       720
atgccagtgg tcagtaccca gctgctgctg aacggatcac tggccgagga agagatcatt      780
atccggtccg aaaatctgac caacaatatc aagaccatta tcgtgcacct gaacaagtcc      840
gtggagatcg tctgcaccag acctaacaat aacacaagga aatctattcg catcggccca      900
gggcagacat tttacgctac tggggaaatt atcggaaata ttcgggaggc acattgcaat      960
atctcaaaga gcaactggac cagcacactg gagcaggtga agaagaagct gaaggaacac      1020
tacaataaga caatcgagtt caacccccct tctggcgggg acctggaagt gactacccat      1080
agttttaatt gcagaggcga gttcttttat tgtaacacaa ctaaactgtt ctctaacaac      1140
tccgattcta caacgaaac tattaccctg ccatgcaaaa tcaagcagat tatcaacatg       1200
tggcagaaag tggggagggc aatgtatgcc ccacccattg agggaaatat cacctgtaaa      1260
agtaacatta ctggcctgct gctgacccgc gacggaggca agaataccac aaacgaaatc      1320
tttagacccg gggaggcaa tatgaaagat aactggagga gtgagctgta caaatataag       1380
gtggtcgaga ttgaacccct gggcgtggcc cctaccaaat caaagaggcg agtggtcgag      1440
ggcggtggag gctcaggtgg aggcggatcc gcagtgggac tggagctgt cctgctgggg       1500 ttcctgggag cagctggctc aacaatgggc gcagccagca tcacactgac tgtgcaggca      1560
cgacagctgc tgtccgggat tgtccagcag cagtctaacc tgctgagagc tcccgaagca      1620
cagcagcaca tgctgcagct gactgtgtgg ggaattaagc agctgcagac ccgagtcctg      1680
gcaatcgagc ggtacctgaa agaccagcag ctgctgggac tgtggggatg ctccggcaag      1740
attatctgta ctaccgctgt gccctggaac agcagctgga gtaacaagtc acaggaggac      1800
atctgggata atatgacatg gatgcagtgg gaccgcgaaa tttcaaacta caccggcaca      1860
atctatcgac tgctggagga tagccagaat cagcaggaga gaacgaaaaa ggacctgctg      1920
gccctggatg cggccgcatg a                                                1941
```

<210> SEQ ID NO 18
<211> LENGTH: 2100
<212> TYPE: DNA
<213> ORGANISM: Artificial
<220> FEATURE:
<223> OTHER INFORMATION: Du151 Gp140FL fused to truncated HA2 of
      influenza

<400> SEQUENCE: 18

```
atggagtggt cttggatctt cctgttcctg ctgtctggga ctgctggagt gcatagttcc       60
ggagtcggca acctgaatct gtgggtgacc gtgtactatg cgtgcccgt ctggaaagaa       120 gcaaagacca cactgttttg cgccagcgac gctaaagcat acgataagga ggtgcacaat       180
gtctgggcca cacatgcttg tgtgcctact gaccctaatc cacgggagat cgtgctggaa      240
```

```
aacgtcactg agaatttcaa catgtggaag aacgacatgg tggatcagat gcacgaggac    300
atcatttctc tgtgggatca gagtctgaaa ccatgcgtga agctgacccc cctgtgcgtc    360
acactgaatt gtactaacgc ccctgcttac aacaatagca tgcatgggga atgaagaac    420
tgttccttta acactaccac agagatccga daccggaaac agaaggcata cgccctgttc    480
tataagcctg atgtggtccc actgaaccgg agagaggaaa acaatggaac aggcgagtat    540
attctgatta actgcaacag ctccacaatt actcaggcct gtccaaaagt gacttttgat    600
cccattccta tccactactg cgctcccgca ggctatgcta tcctgaaatg taacaataag    660
accttcaatg gacaggacc ttgcaacaat gtgagcactg tccagtgtac ccatgggatc    720
atgccagtgg tcagtaccca gctgctgctg aacggatcac tggccgagga agagatcatt    780
atccggtccg aaaatctgac caacaatatc aagaccatta cgtgcacct gaacaagtcc    840
gtggagatcg tctgcaccag acctaacaat aacacaagga aatctattcg catcggccca    900
gggcagacat tttacgctac tggggaaatt atcggaaata ttcggaggc acattgcaat    960
atctcaaaga gcaactggac cagcacactg gagcaggtga agaagaagct gaaggaacac   1020
tacaataaga caatcgagtt caacccccct tctggcgggg acctggaagt gactacccat    1080
agttttaatt gcagaggcga gttctttat tgtaacacaa ctaaactgtt ctctaacaac   1140
tccgattcta caacgaaac tattaccctg ccatgcaaaa tcaagcagat tatcaacatg   1200
tggcagaaag tggggagggc aatgtatgcc ccacccattg agggaaatat cacctgtaaa   1260
agtaacatta ctggcctgct gctgacccgc gacggaggca agaataccac aaacgaaatc   1320
tttagacccg ggggaggcaa tatgaaagat aactggagga gtgagctgta caaatataag   1380
gtggtcgaga ttgaaccccct gggcgtggcc cctaccaaat caagaggcg agtggtcgag   1440
ggcggtggag gctcaggtgg aggcggatcc gcagtgggac tgggagctgt cctgctgggg   1500
ttcctgggag cagctggctc aacaatgggc gcagccagca tcacactgac tgtgcaggca   1560
cgacagctgc tgtccgggat tgtccagcag cagtctaacc tgctgagagc tcccgaagca   1620
cagcagcaca tgctgcagct gactgtgtgg ggaattaagc agctgcagac ccgagtcctg   1680
gcaatcgagc ggtacctgaa agaccagcag ctgctggac tgtggggatg ctccggcaag   1740
attatctgta ctaccgctgt gccctggaac agcagctgga gtaacaagtc acaggaggac   1800
atctgggata tatgacatg gatgcagtgg gaccgcgaaa tttcaaacta caccggcaca   1860
atctatcgac tgctggagga tagccagaat cagcaggaga agaacgaaaa ggacctgctg    1920
gccctggatt cttggaaaaa tctgtggaac tggttcaata tcaccaactg gctgtggtac   1980
attcagatcc tgagtatcta ttcaaccgtg gcttcaagcc tggctctggc aattatggtc   2040
gcaggcctgt ctctgtggat gtgcagcaac gggtccctgc agtgtcgagc ggccgcatga   2100
```

<210> SEQ ID NO 19
<211> LENGTH: 2109
<212> TYPE: DNA
<213> ORGANISM: Artificial
<220> FEATURE:
<223> OTHER INFORMATION: Du151 Gp120FL fused to HA2 of influenza

<400> SEQUENCE: 19

```
atggagtggt cttggatctt cctgttcctg ctgtctggga ctgctggagt gcatagttcc    60
ggagtcggca acctgaatct gtgggtgacc gtgtactatg cgtgcccgt ctggaaagaa   120
gcaaagacca cactgttttg cgccagcgac gctaaagcat acgataagga ggtgcacaat    180
```

```
gtctgggcca cacatgcttg tgtgcctact gaccctaatc cacgggagat cgtgctggaa    240
aacgtcactg agaatttcaa catgtggaag aacgacatgg tggatcagat gcacgaggac    300
atcatttctc tgtgggatca gagtctgaaa ccatgcgtga agctgacccc cctgtgcgtc    360
acactgaatt gtactaacgc ccctgcttac aacaatagca tgcatgggga aatgaagaac    420 tgttcctttā acactaccac agagatccga gaccggaaac agaaggcata cgccctgttc    480
tataagcctg atgtggtccc actgaaccgg agagaggaaa acaatggaac aggcgagtat    540
attctgatta actgcaacag ctccacaatt actcaggcct gtccaaaagt gacttttgat    600
cccattccta tccactactg cgctcccgca ggctatgcta tcctgaaatg taacaataag    660
accttcaatg ggacaggacc ttgcaacaat gtgagcactg tccagtgtac ccatgggatc    720
atgccagtgg tcagtaccca gctgctgctg aacggatcac tggccgagga agagatcatt    780
atccggtccg aaaatctgac caacaatatc aagaccatta tcgtgcacct gaacaagtcc    840
gtggagatcg tctgcaccag acctaacaat aacacaagga atctattcg catcggccca     900 gggcagacat tttacgctac tggggaaatt atcggaaata ttcggaggc acattgcaat      960 atctcaaaga gcaactggac cagcacactg gagcaggtga agaagaagct gaaggaacac    1020
tacaataaga caatcgagtt caaccccct tctggcgggg acctggaagt gactacccat     1080
agttttaatt gcagaggcga gttcttttat tgtaacacaa ctaaactgtt ctctaacaac    1140
tccgattcta caacgaaac tattaccctg ccatgcaaaa tcaagcagat tatcaacatg      1200
tggcagaaag tggggagggc aatgtatgcc ccacccattg agggaaatat cacctgtaaa    1260
agtaacatta ctggcctgct gctgacccgc gacggaggca agaataccac aaacgaaatc    1320
tttagacccg gggaggcaa tatgaaagat aactggagga gtgagctgta caaatataag      1380
gtggtcgaga ttgaacccct gggcgtggcc cctaccaaat caagaggcg agtggtcgag    1440 ggcggtggag gctcaggtgg aggcggatcc gagggggat ggcagggaat ggtggacggg      1500
tggtacggat atcaccattc aaacgaacag gggagcggat atgccgctga caaggagtct    1560
acacagaaag caatcgatgg ggtgactaac aaggtcaata gtatcatcga taagatgaat    1620
acccagttcg aagccgtggg acgcgagttt aacaatctgg aacgccgaat cgagaacctg    1680
aataagaaaa tggaagacgg cttcctggat gtgtggacct acaacgctga gctgctggtc    1740
ctgatggaaa atgagcggac actggacttt cacgatagca acgtgaagaa tctgtatgac    1800
aaagtcagac tgcagctgag ggataacgcc aaggaactgg gcaatgggtg cttcgagttt    1860
taccataaat gcgacaacga atgtatggag agtgtgcgca atggcaccta cgattatcct    1920
cagtattcag aagaggcccg gctgaagaga aagagattac gcggcgtgaa actggagtct    1980
attggcatct accagatcct gagtatctat tcaaccgtgg cttcaagcct ggctctggca    2040
attatggtcg caggcctgtc tctgtggatg tgcagcaacg ggtccctgca gtgtcgagcg    2100
gccgcatga                                                            2109

<210> SEQ ID NO 20
<211> LENGTH: 2178
<212> TYPE: DNA
<213> ORGANISM: Artificial
<220> FEATURE:
<223> OTHER INFORMATION: Du151 Gp150FL

<400> SEQUENCE: 20
atggagtggt cttggatctt cctgttcctg ctgtctggga ctgctggagt gcatagttcc     60
ggagtcggca acctgaatct gtgggtgacc gtgtactatg gcgtgcccgt ctggaaagaa    120
```

```
gcaaagacca cactgttttg cgccagcgac gctaaagcat acgataagga ggtgcacaat        180
gtctgggcca cacatgcttg tgtgcctact gaccctaatc cacgggagat cgtgctggaa        240
aacgtcactg agaatttcaa catgtggaag aacgacatgg tggatcagat gcacgaggac        300
atcatttctc tgtgggatca gagtctgaaa ccatgcgtga agctgacccc cctgtgcgtc        360
acactgaatt gtactaacgc ccctgcttac aacaatagca tgcatgggga atgaagaac        420 tgttcctta acactaccac agagatccga gaccggaaac agaaggcata cgccctgttc        480
tataagcctg atgtggtccc actgaaccgg agagaggaaa acaatggaac aggcgagtat        540
attctgatta actgcaacag ctccacaatt actcaggcct gtccaaaagt gacttttgat        600
cccattccta tccactactg cgctcccgca ggctatgcta tcctgaaatg taacaataag        660
accttcaatg ggacaggacc ttgcaacaat gtgagcactg tccagtgtac ccatgggatc        720
atgccagtgg tcagtaccca gctgctgctg aacggatcac tggccgagga agagatcatt        780
atccggtccg aaaatctgac caacaatatc aagaccatta tcgtgcacct gaacaagtcc        840
gtggagatcg tctgcaccag acctaacaat aacacaagga aatctattcg catcggccca        900
gggcagacat tttacgctac tggggaaatt atcggaaata ttcggaggc acattgcaat        960 atctcaaaga gcaactggac cagcacactg gagcaggtga agaagaagct gaaggaacac       1020
tacaataaga caatcgagtt caacccccct tctggcgggg acctggaagt gactacccat       1080
agttttaatt gcagaggcga gttcttttat tgtaacacaa ctaaactgtt ctctaacaac       1140
tccgattcta caacgaaac tattaccctg ccatgcaaaa tcaagcagat tatcaacatg       1200
tggcagaaag tggggagggc aatgtatgcc ccacccattg agggaaatat cacctgtaaa       1260
agtaacatta ctggcctgct gctgacccgc gacggaggca agaataccac aaacgaaatc       1320
tttagacccg gggaggcaa tatgaaagat aactggagga gtgagctgta caaatataag       1380
gtggtcgaga ttgaaccccct gggcgtggcc cctaccaaat caagagagcg agtggtcgag       1440
ggcggtggag gctcaggtgg aggcggatcc gcagtgggac tgggagctgt cctgctgggg       1500
ttcctgggag cagctggctc aacaatgggc gcagccagca tcacactgac tgtgcaggca       1560
cgacagctgc tgtccgggat tgtccagcag cagtctaacc tgctgagagc tcccgaagca       1620
cagcagcaca tgctgcagct gactgtgtgg ggaattaagc agctgcagac ccgagtcctg       1680
gcaatcgagc ggtacctgaa agaccagcag ctgctggac tgtggggatg ctccggcaag       1740
attatctgta ctaccgctgt gccctggaac agcagctgga gtaacaagtc acaggaggac       1800
atctgggata tatgacatg gatgcagtgg gaccgcgaaa tttcaaacta caccggcaca       1860
atctatcgac tgctggagga tagccagaat cagcaggaga agaacgaaaa ggacctgctg       1920
gccctggatt cttggaaaaa tctgtggaac tggttcaata tcaccaactg gctgtggtac       1980
attaagatct ttattatgat cgtgggggga ctgattggac tgaggattat ctttggcgtg       2040
ctggccatcg tgaagagagt caggcagggc tatagccccc tgtccttcca gactctgacc       2100 ccaagcccc gcggccctga tcggctgggg agaatcgaag aggaaggcgg ggagcaggac       2160
aaggatgcgg ccgcatga                                                    2178
```

<210> SEQ ID NO 21
<211> LENGTH: 21
<212> TYPE: PRT
<213> ORGANISM: Artificial
<220> FEATURE:
<223> OTHER INFORMATION: LPH Secretory Signal Peptide

```
<400> SEQUENCE: 21

Met Glu Trp Ser Trp Ile Phe Leu Phe Leu Leu Ser Gly Thr Ala Gly
1               5                   10                  15

Val His Ser Ser Gly
            20

<210> SEQ ID NO 22
<211> LENGTH: 10
<212> TYPE: PRT
<213> ORGANISM: Artificial
<220> FEATURE:
<223> OTHER INFORMATION: Flexible Linker

<400> SEQUENCE: 22

Gly Gly Gly Gly Ser Gly Gly Gly Gly Ser
1               5                   10
```

PRODUCTION OF SOLUBLE HIV ENVELOPE TRIMERS IN PLANTA

CROSS-REFERENCE TO RELATED APPLICATIONS

This application is a national stage filing under 35 U.S.C. 371 of PCT/IB2017/056349 filed Oct. 13, 2017, which International Application was published by the International Bureau in English on Apr. 19, 2018, which claims priority to Great Britain Application No. 1617480.7, filed on Oct. 14, 2016, which are both hereby incorporated herein in their entirety by reference.

BACKGROUND OF THE INVENTION

This invention relates to methods for producing recombinant HIV glycoprotein polypeptides in a plant and trimeric Env complexes of the recombinant, plant-produced HIV glycoprotein polypeptide which mimic the wildtype HIV Env complex. The invention also provides for nucleic acids encoding the recombinant HIV glycoprotein polypeptides and to pharmaceutical compositions, uses and methods of eliciting an immune response against HIV in a subject using the recombinant HIV glycoprotein polypeptides and trimeric complexes.

The HIV pandemic is a global public health challenge and is particularly problematic in developing countries, which are often disproportionately affected and lack the infrastructure necessary for manufacturing of their own vaccines. A major focal point of current HIV vaccine research is the development of native-like envelope protein trimers that are capable of inducing neutralizing antibodies. These antigens are typically produced by transfection of mammalian cells, such as HEK 293T, HEK 293F, CHO-K1 or GnTI-/- cell lines. In recent years, plants have emerged as a viable alternative to conventional expression platforms, particularly in developing countries where the infrastructure is limited and costs are prohibitive.

The present invention relates to the production of recombinant HIV glycoprotein polypeptides, preferably the HIV glycoprotein polypeptides are selected from the group consisting of soluble HIV Env gp140 mimetics, membrane-associated gp150 mimetics, membrane-associated gp160 mimetics or chimaeric HIV polypeptides in plants which exploit a native flexible linker to allow proper folding in the absence of furin cleavage. This is to the present inventors' knowledge the largest portion of the HIV-1 envelope glycoprotein (Env) that has been successfully expressed in plants and the first time that is has been shown that plants are capable of reproducing the trimeric structure of the protein. This is also the first report showing that soluble gp140 proteins from HIV Subtype C isolates have been expressed. The recombinant proteins demonstrate reactivity with several prototype monoclonal antibodies isolated from people with natural infections. Most importantly, the immunogens show reactivity with PGT145, which specifically reacts with well-ordered trimers. This confirms that plants have the capacity to reproduce the quaternary structure of the native protein. Additionally, the antigens are immunogenic in rabbits, inducing HIV Env-specific antibodies after a single immunization. This is also the only report to our knowledge that describes the immunogenicity of a plant produced HIV-1 gp140 antigen in animals.

Few other studies have explored the potential of plants as an expression platform for HIV Env vaccines. A number of studies have successfully expressed variable regions of gp120 or portions of gp41 as fusions with either plant virus capsid proteins or using cholera toxin B as a carrier. Although these vaccines are immunogenic they are unlikely to ever be protective because they do not faithfully reproduce the structure of these regions (Rybicki, 2010). More recently, Kessans et al. have produced Gag VLPs presenting the membrane-proximal external region (MPER) of gp41 in N. benthamiana plants (Kessans et al., 2016). The most promising study to date was conducted by Rosenberg and colleagues who expressed a truncated, soluble Env protein in N. benthamiana plants. Although the immunogenicity of the antigen was not reported, the protein was reported to react with several prototype monoclonal antibodies (Rosenberg et al., 2013). However, the Subtype B Env gp140 protein produced by Rosenberg et al was extensively modified to remove the cleavage site, fusion peptide and immunodominant region of gp41. Further, there is no evidence that the protein produced by Rosenberg et al is capable of forming trimers or that it is immunogenic. Given subsequent insights into the structure of the Env glycoprotein since the study, this protein is unlikely to be properly processed due to truncation of the cleavage site at the interface of gp120 and gp41 which prevents the formation of properly folded Env unless it is replaced with a linker peptide (Ringe et al., 2013; Sharma et al., 2015). Further, no one has successfully expressed whole HIV Env gp160 protein or a major portion of the protein in plants at a reasonable yield (Rybicki, 2010).

It is further submitted that while it may be possible to some extent to determine ways of increasing recombinant protein expression in plants, this is dependent on a number of factors that are not predictable at all. For example, there is no single suitable host or production system, as well as no single organelle or export targeting option (Rybicki, 2010).

SUMMARY OF THE INVENTION

According to a first aspect of the invention there is provided for a method for producing a recombinant polypeptide capable of forming a trimeric Env glycoprotein complex, the method comprising the steps of:
(i) providing a codon-optimised nucleotide sequence encoding a recombinant polypeptide having the formula:

$$X_1-X_2-X_3-X_4$$

wherein, $X_1$ represents a secretory signal peptide; $X_2$ represents an HIV gp120 envelope polypeptide; $X_3$ is a linker peptide; and $X_4$ is a HIV gp41 polypeptide, wherein the gp41 polypeptide is selected from either a full-length gp41 polypeptide or a truncated gp41 polypeptide, wherein if the gp41 polypeptide is a truncated gp41 polypeptide then it is truncated after the LALD motif of the gp41 polypeptide;
(ii) cloning the codon-optimised nucleic acid encoding the recombinant polypeptide into an expression vector adapted to express the recombinant polypeptide in a plant cell;
(iii) transforming the plant cell with the expression vector of step (ii);
(iv) expressing the recombinant polypeptide in the plant cell; and
(v) recovering the recombinant polypeptide from the plant cell.

In an alternative embodiment of the invention the recombinant polypeptide has the formula:

$$X_1-X_2-X_3-X_4-X_5$$

wherein, $X_5$ is optionally included and when included $X_5$ is a truncated influenza virus $HA_2$ molecule with transmembrane and cytoplasmic domains. In one embodiment the recombinant polypeptide comprises an I559P mutation.

In a second embodiment the secretory signal peptide is LPH having the amino acid sequence MEWSWIFLFLLSGTAGVHSSG (SEQ ID NO:21).

In a third embodiment the linker peptide is a flexible linker comprising the amino acid sequence GGGGSGGGGS (SEQ ID NO:22). Those of skill in the art will appreciate that various additional stabilizing mutations may be introduced to the sequences of the invention, these may include but are not limited to the introduction of artificial disulphide bonds to limit structural plasticity or other mutations to improve the efficiency at which native-like trimers assemble.

In yet another embodiment of the invention the plant cell is a *Nicotiana bethamiana* plant cell. It will however be appreciated that other plants or plant cells may be used.

In a further embodiment of the invention it will be appreciated that the step of transforming the plant cell may be performed by *Agrobacterium* mediated transformation. Preferably, the *Agrobacterium* is *A. tumefaciens* and more preferably the *A. tumefaciens* strain may be selected from the group consisting of LBA4404, GV3101(pM90RK) and AGL1.

In a second aspect of the invention there is provided for a recombinant polypeptide capable of forming a trimeric Env glycoprotein complex produced according to the methods described herein, having the formula:

$$X_1-X_2-X_3-X_4$$

wherein, $X_1$ represents a secretory signal peptide; $X_2$ represents an HIV gp120 envelope polypeptide; $X_3$ is a linker peptide; and $X_4$ is a HIV gp41 polypeptide, wherein the gp41 polypeptide is selected from either a full-length gp41 polypeptide or a truncated gp41 polypeptide, wherein if the gp41 polypeptide is a truncated gp41 polypeptide then it is truncated after the LALD motif of the gp41 polypeptide.

In an alternative embodiment the recombinant polypeptide has the formula:

$$X_1-X_2-X_3-X_4-X_5$$

wherein, $X_5$ is optionally included and further wherein $X_5$ is a truncated influenza virus $HA_2$ molecule with cytoplasmic and membrane localisation domains.

In a third aspect of the invention there is provided for a trimeric Env glycoprotein complex, comprising three recombinant polypeptides.

A fourth aspect of the invention provides for a nucleic acid encoding the recombinant polypeptide and a fifth aspect provides for an expression vector comprising the nucleic acid.

A further aspect of the invention provides for a pharmaceutical composition comprising the recombinant polypeptide or the trimeric Env glycoprotein complex. In one embodiment the pharmaceutical composition further comprises a pharmaceutically acceptable carrier or adjuvant.

In yet another aspect of the invention there is provided for the polypeptide described herein, the trimeric Env glycoprotein complex or the pharmaceutical composition for use in a method of eliciting an immune response against HIV in a subject, the method comprising administering an effective amount of the polypeptide, trimeric Env glycoprotein complex or the pharmaceutical composition to the subject. It will be appreciated that in a preferred embodiment of the invention the subject is a human.

In a further aspect of the invention there is provided for the use of the polypeptides described herein or the trimeric Env glycoprotein complex for the preparation of a medicament.

In yet another aspect of the invention there is provided for a method of eliciting an immune response against HIV in a subject, the method comprising administering an effective amount of the polypeptides of the invention, the trimeric Env glycoprotein complex or the pharmaceutical composition to the subject.

It will be appreciated that in a preferred embodiment of the invention the subject is a human.

BRIEF DESCRIPTION OF THE FIGURES

Non-limiting embodiments of the invention will now be described by way of example only and with reference to the following figures:

FIG. 10: Amino acid sequence of CAP256SU Gp140Gly fused to $HA_2$ of influenza (SEQ ID NO:4) and encoded by the nucleotide sequence of SEQ ID NO:14 the LPH amino acid leader sequence is underlined, the flexible linker is shown in italics and the $HA_2$ amino acid sequences are shown in bold.

FIG. 11: Amino acid sequence of CAP256SU Gp120Gly fused to $HA_2$ of influenza (SEQ ID NO:5) and encoded by the nucleotide sequence of SEQ ID NO:15 the LPH amino acid leader sequence is underlined, the flexible linker is shown in italics and the $HA_2$ amino acid sequences are shown in bold.

FIG. 12: Amino acid sequence of CAP256SU Gp150Gly SEQ ID NO:6) and encoded by the nucleotide sequence of SEQ ID NO:16 the LPH amino acid leader sequence is underlined and the flexible linker is shown in italics.

FIG. 13: Amino acid sequence of CAP256SU Gp160Gly (SEQ ID NO:7) the LPH amino acid leader sequence is underlined and the flexible linker is shown in italics.

FIG. 14: Amino acid sequence of Du151 Gp140Gly fused to $HA_2$ of influenza (SEQ ID NO:8) and encoded by the nucleotide sequence of SEQ ID NO:17 the LPH amino acid leader sequence is underlined, the flexible linker is shown in italics and the $HA_2$ amino acid sequences are shown in bold.

FIG. 15: Amino acid sequence of Du151 Gp120Gly fused to $HA_2$ of influenza (SEQ ID NO:10) and encoded by the nucleotide sequence of SEQ ID NO:19 the LPH amino acid leader sequence is underlined, the flexible linker is shown in italics and the $HA_2$ amino acid sequences are shown in bold.

FIG. 16: Amino acid sequence of Du151 Gp150Gly (SEQ ID NO:11) and encoded by the nucleotide sequence of SEQ ID NO:20 the LPH amino acid leader sequence is underlined and the flexible linker is shown in italics.

FIG. 17: Amino acid sequence of Du151 Gp160Gly (SEQ ID NO:12) the LPH amino acid leader sequence is underlined and the flexible linker is shown in italics.

FIG. 18: Amino acid sequence of CAP256SU Gp140NFL (SEQ ID NO:3) and encoded by the nucleotide sequence of SEQ ID NO:13 the LPH amino acid leader sequence is underlined and the flexible linker is shown in italics.

FIG. 19: Amino acid sequence of Du151 Gp140FL fused to truncated $HA_2$ of influenza (SEQ ID NO:9) and encoded by the nucleotide sequence of SEQ ID NO:18 the LPH amino acid leader sequence is underlined, the flexible linker is shown in italics and the $HA_2$ amino acid sequences are shown in bold.

SEQUENCE LISTING

Figure 1:
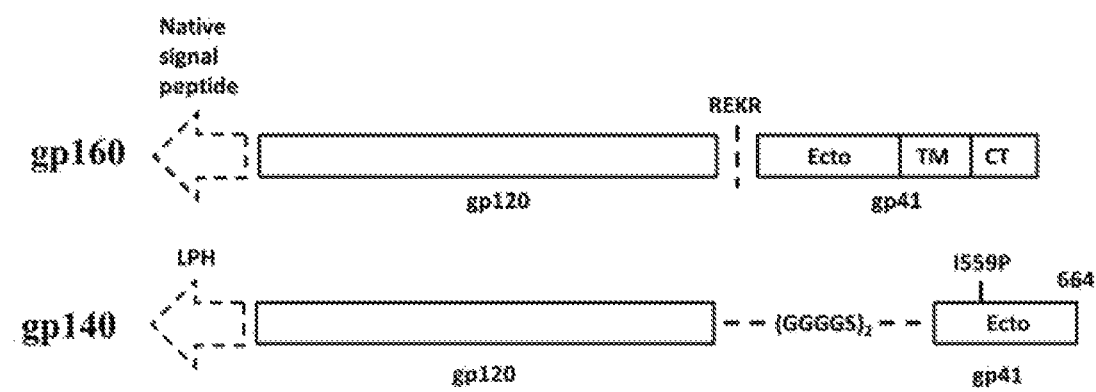
FIG. 1: Schematic of the coding sequences of (A) the native gp160 gene and (B) the gp140 NFL antigen. The gp120 and gp41 portions of the proteins are delineated with either the native cleavage sequence (REKR) or flexible (GGGGS)2 linker peptide at the interface of the two subunits. The ectodomain (Ecto), transmembrane (TM) and cytoplasmic (CT) regions of gp41 are indicated. The location of the I559P helix breaking mutation and amino acid residue 664, where the coding sequence was terminated, is reflected for the gp140 NFL antigen. The native and LPH signal sequences are indicated by the dashed arrows respectively.

The nucleic acid and amino acid sequences listed in the accompanying sequence listing are shown using standard letter abbreviations for nucleotide bases, and the standard three letter abbreviations for amino acids. It will be understood by those of skill in the art that only one strand of each nucleic acid sequence is shown, but that the complementary strand is included by any reference to the displayed strand. The accompanying sequence listing is hereby incorporated by reference in its entirety.

DETAILED DESCRIPTION OF THE INVENTION

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

The present invention relates to recombinant, soluble gp140 polypeptides, recombinant membrane-associated gp150 polypeptides, membrane-associated gp160 polypeptides or chimaeric HIV polypeptides. In the recombinant polypeptides the natural furin cleavage site has been deleted and replaced with an amino acid linker, preferably the amino acid linker comprises a peptide comprising two repeats of the sequence GGGGS. In one embodiment of the invention the isoleucine residue at position 559 of the polypeptide was mutated to be replaced by a proline residue. In yet a further embodiment of the invention the coding sequence is prematurely terminated after amino acid residue 664 and in so doing the recombinant polypeptide does not contain the transmembrane and/or cytoplasmic regions of gp41. In an alternative embodiment of the invention the coding sequence of the gp41 polypeptide is not truncated and contains the transmembrane and/or cytoplasmic regions of gp41. The Applicants have also designed the recombinant protein to include a LPH signal sequence in order to allow targeting through the secretory pathway. The recombinant gp140 polypeptides, recombinant membrane-associated gp150 polypeptides, membrane-associated gp160 polypeptides or chimaeric HIV polypeptides of the invention are capable of assembling into trimers.

A "protein," "peptide" or "polypeptide" is any chain of two or more amino acids, including naturally occurring or non-naturally occurring amino acids or amino acid analogues, irrespective of post-translational modification (e.g., glycosylation or phosphorylation).

The terms "nucleic acid", "nucleic acid molecule" and "polynucleotide" are used herein interchangeably and encompass both ribonucleotides (RNA) and deoxyribonucleotides (DNA), including cDNA, genomic DNA, and synthetic DNA. The nucleic acid may be double-stranded or single-stranded. Where the nucleic acid is single-stranded, the nucleic acid may be the sense strand or the antisense strand. A nucleic acid molecule may be any chain of two or more covalently bonded nucleotides, including naturally occurring or non-naturally occurring nucleotides, or nucleotide analogs or derivatives. By "RNA" is meant a sequence of two or more covalently bonded, naturally occurring or modified ribonucleotides. The term "DNA" refers to a sequence of two or more covalently bonded, naturally occurring or modified deoxyribonucleotides.

The term "isolated", is used herein and means having been removed from its natural environment.

The term "purified", relates to the isolation of a molecule or compound in a form that is substantially free of contamination or contaminants. Contaminants are normally associated with the molecule or compound in a natural environment, purified thus means having an increase in purity as a result of being separated from the other components of an original composition. The term "purified nucleic acid" describes a nucleic acid sequence that has been separated from other compounds including, but not limited to polypeptides, lipids and carbohydrates which it is ordinarily associated with in its natural state.

The term "complementary" refers to two nucleic acid molecules, e.g., DNA or RNA, which are capable of forming Watson-Crick base pairs to produce a region of double-strandedness between the two nucleic acid molecules. It will be appreciated by those of skill in the art that each nucleotide in a nucleic acid molecule need not form a matched Watson-Crick base pair with a nucleotide in an opposing complementary strand to form a duplex. One nucleic acid molecule is thus "complementary" to a second nucleic acid molecule if it hybridizes, under conditions of high stringency, with the second nucleic acid molecule. A nucleic acid molecule according to the invention includes both complementary molecules.

As used herein a "substantially identical" sequence is an amino acid or nucleotide sequence that differs from a reference sequence only by one or more conservative substitutions, or by one or more non-conservative substitutions, deletions, or insertions located at positions of the sequence that do not destroy or substantially reduce the antigenicity of one or more of the expressed polypeptides or of the polypeptides encoded by the nucleic acid molecules. Alignment for purposes of determining percent sequence identity can be achieved in various ways that are within the knowledge of those with skill in the art. These include using, for instance, computer software such as ALIGN, Megalign (DNASTAR), CLUSTALW or BLAST software. Those skilled in the art can readily determine appropriate parameters for measuring alignment, including any algorithms needed to achieve maximal alignment over the full length of the sequences being compared. In one embodiment of the invention there is provided for a polypeptide or polynucleotide sequence that has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or 100% sequence identity to the sequences described herein.

Alternatively, or additionally, two nucleic acid sequences may be "substantially identical" if they hybridize under high stringency conditions. The "stringency" of a hybridisation reaction is readily determinable by one of ordinary skill in the art, and generally is an empirical calculation which depends upon probe length, washing temperature, and salt concentration. In general, longer probes required higher temperatures for proper annealing, while shorter probes require lower temperatures. Hybridisation generally depends on the ability of denatured DNA to re-anneal when complementary strands are present in an environment below their melting temperature. A typical example of such "stringent" hybridisation conditions would be hybridisation carried out for 18 hours at 65° C. with gentle shaking, a first wash for 12 min at 65° C. in Wash Buffer A (0.5% SDS; 2×SSC), and a second wash for 10 min at 65° C. in Wash Buffer B (0.1% SDS; 0.5% SSC).

Those skilled in the art will appreciate that polypeptides, peptides or peptide analogues can be synthesised using standard chemical techniques, for instance, by automated synthesis using solution or solid phase synthesis methodology. Automated peptide synthesisers are commercially available and use techniques known in the art. Polypeptides, peptides and peptide analogues can also be prepared from their corresponding nucleic acid molecules using recombinant DNA technology.

As used herein, the term "gene" refers to a nucleic acid that encodes a functional product, for instance a RNA, polypeptide or protein. A gene may include regulatory sequences upstream or downstream of the sequence encoding the functional product.

As used herein, the term "coding sequence" refers to a nucleic acid sequence that encodes a specific amino acid sequence. On the other hand a "regulatory sequence" refers to a nucleotide sequence located either upstream, downstream or within a coding sequence. Generally regulatory sequences influence the transcription, RNA processing or stability, or translation of an associated coding sequence. Regulatory sequences include but are not limited to: effector binding sites, enhancers, introns, polyadenylation recognition sequences, promoters, RNA processing sites, stem-loop structures, translation leader sequences and the like.

In some embodiments, the genes used in the method of the invention may be operably linked to other sequences. By "operably linked" is meant that the nucleic acid molecules encoding the recombinant gp140 antigen polypeptides, the recombinant gp150 antigen polypeptides, the gp160 antigen polypeptides or the chimaeric HIV antigen polypeptides of the invention and regulatory sequences are connected in such a way as to permit expression of the proteins when the appropriate molecules are bound to the regulatory sequences. Such operably linked sequences may be contained in vectors or expression constructs which can be transformed or transfected into host cells for expression. Alternatively the operably linked sequences may be transformed into a bacterial vector to mediate expression in planta. It will be appreciated that any vector or vectors can be used for the purposes of expressing the recombinant antigenic polypeptides of the invention.

The term "promoter" refers to a DNA sequence that is capable of controlling the expression of a nucleic acid coding sequence or functional RNA. A promoter may be based entirely on a native gene or it may be comprised of different elements from different promoters found in nature or a promoter could be an entirely synthetic construct. Different promoters are capable of directing the expression of a gene in different cell types, or at different stages of development, or in response to different environmental or physiological conditions. A "constitutive promoter" is a promoter that directs the expression of a gene of interest in most host cell types most of the time.

The term "recombinant" means that something has been recombined. When used with reference to a nucleic acid construct the term refers to a molecule that comprises nucleic acid sequences that are joined together or produced by means of molecular biological techniques. The term "recombinant" when used in reference to a protein or a polypeptide refers to a protein or polypeptide molecule which is expressed from a recombinant nucleic acid construct created by means of molecular biological techniques. Recombinant nucleic acid constructs may include a nucleotide sequence which is ligated to, or is manipulated to become ligated to, a nucleic acid sequence to which it is not ligated in nature, or to which it is ligated at a different location in nature. Accordingly, a recombinant nucleic acid construct indicates that the nucleic acid molecule has been manipulated using genetic engineering, i.e. by human intervention. Recombinant nucleic acid constructs may be introduced into a host cell by transformation. Such recombinant nucleic acid constructs may include sequences derived from the same host cell species or from different host cell species.

As used herein, the term "chimaeric", means that a sequence comprises of sequences that have been "recombined". By way of example sequences are recombined and are not found together in nature. The term "recombine" or "recombination" refers to any method of joining two or more polynucleotides. The term includes end to end joining, and insertion of one sequence into another. The term is intended to include physical joining techniques, for instance, sticky-end ligation, blunt-end ligation, as well as PCR-mediated fusion by overlap extension PCR. Sequences may also be artificially synthesized to contain a recombined sequence. The term may also encompass the integration of one sequence into a second sequence by way of, for example, homologous recombination.

The term "vector" refers to a means by which polynucleotides or gene sequences can be introduced into a cell. There are various types of vectors known in the art including plasmids, viruses, bacteriophages and cosmids. Generally polynucleotides or gene sequences are introduced into a vector by means of a cassette. The term "cassette" refers to a polynucleotide or gene sequence that is expressed from a vector, for example, the polynucleotide or gene sequences encoding the acyl transferase polypeptides of the invention. A cassette generally comprises a gene sequence inserted into a vector, which in some embodiments, provides regulatory sequences for expressing the polynucleotide or gene sequences. In other embodiments, the vector provides the regulatory sequences for the expression of the acyl transferase polypeptides. In further embodiments, the vector provides some regulatory sequences and the nucleotide or gene sequence provides other regulatory sequences. "Regulatory sequences" include but are not limited to promoters, transcription termination sequences, enhancers, splice acceptors, donor sequences, introns, ribosome binding sequences, poly(A) addition sequences, and/or origins of replication.

The recombinant gp140 antigen, the recombinant gp150 antigen, the recombinant gp160 antigen and/or the chimaeric HIV antigen or compositions of the invention containing these antigens can be provided either alone or in combination with other compounds (for example, nucleic acid molecules, small molecules, peptides, or peptide analogues), in the presence of a liposome, an adjuvant, or any carrier, such as a pharmaceutically acceptable carrier and in a form suitable for administration to mammals, for example, humans, cattle, sheep, etc.

In one embodiment of the invention the trimer protein of the invention is formulated for immunization together with an adjuvant. Adjuvants are well known to those of skill in the art of vaccine development and are not limited to the adjuvants specifically exemplified herein.

As used herein a "pharmaceutically acceptable carrier" or "excipient" includes any and all antibacterial and antifungal agents, coatings, dispersion media, solvents, isotonic and absorption delaying agents, and the like that are physiologically compatible. A "pharmaceutically acceptable carrier" may include a solid or liquid filler, diluent or encapsulating substance which may be safely used for the administration of the recombinant antigen or vaccine composition to a subject. The pharmaceutically acceptable carrier can be suitable for intramuscular, intradermal, intravenous, intraperitoneal, subcutaneous, oral or sublingual administration. Pharmaceutically acceptable carriers include sterile aqueous solutions, dispersions and sterile powders for the preparation of sterile solutions. The use of media and agents for the preparation of pharmaceutically active substances is well known in the art. Where any conventional media or agent is incompatible with the active compound, use thereof in the pharmaceutical compositions of the invention is not contemplated. Supplementary active compounds can also be incorporated into the compositions.

Suitable formulations or compositions to administer the recombinant gp140 antigen, the recombinant gp150 antigen, the recombinant gp160 antigen or the chimaeric HIV antigen polypeptides and compositions to subjects infected with HIV or subjects which are presymptomatic for a condition associated with HIV infection fall within the scope of the invention. Any appropriate route of administration may be employed, such as, parenteral, intravenous, subcutaneous, intramuscular, intracranial, intraorbital, ophthalmic, intraventricular, intracapsular, intraspinal, intrathecal, intracisternal, intraperitoneal, intranasal, aerosol, topical, or oral administration.

For vaccine formulations and pharmaceutical compositions, an effective amount of the recombinant gp140 antigen, the recombinant gp150 antigen, the recombinant gp160 antigen or the chimaeric HIV antigen polypeptides or compositions of the invention can be provided, either alone or in combination with other compounds, with immunological adjuvants, for example, aluminium hydroxide dimethyldioctadecyl-ammonium hydroxide or Freund's incomplete adjuvant. The recombinant gp140 antigen, the recombinant gp150 antigen, the recombinant gp160 antigen or the chimaeric HIV antigen polypeptides or compositions of the invention may also be linked with suitable carriers and/or other molecules, such as bovine serum albumin or keyhole limpet haemocyanin in order to enhance immunogenicity.

In some embodiments, the recombinant gp140 antigen, the recombinant gp150 antigen, the recombinant gp160 antigen or the chimaeric HIV antigen polypeptides or compositions according to the invention may be provided in a kit, optionally with a carrier and/or an adjuvant, together with instructions for use.

An "effective amount" of a recombinant gp140 antigen, the recombinant gp150 antigen, the recombinant gp160 antigen or the chimaeric HIV antigen polypeptides or composition according to the invention includes a therapeutically effective amount, immunologically effective amount, or a prophylactically effective amount. A "therapeutically effective amount" refers to an amount effective, at dosages and for periods of time necessary, to achieve the desired therapeutic result, such as treatment of an infection or a condition associated with such infection. The outcome of the treatment may for example be measured by a decrease in viraemia, inhibition of viral gene expression, delay in development of a pathology associated with HIV infection, stimulation of the immune system, or any other method of determining a therapeutic benefit. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects.

The dosage of any of the recombinant gp140 antigen, the recombinant gp150 antigen, the recombinant gp160 antigen or the chimaeric HIV antigen polypeptides or compositions of the present invention will vary depending on the symptoms, age and body weight of the subject, the nature and severity of the disorder to be treated or prevented, the route of administration, and the form of the composition. Any of the compositions of the invention may be administered in a single dose or in multiple doses. The dosages of the compositions of the invention may be readily determined by techniques known to those of skill in the art or as taught herein.

By "immunogenically effective amount" is meant an amount effective, at dosages and for periods of time necessary, to achieve a desired immune response. The desired immune response may include stimulation or elicitation of an immune response, for instance a T-cell response.

A "prophylactically effective amount" refers to an amount effective, at dosages and for periods of time necessary, to achieve a desired prophylactic result, such as prevention of onset of a condition associated with HIV infection. Typically, a prophylactic dose is used in a subject prior to or at an earlier stage of disease, so that a prophylactically effective amount may be less than a therapeutically effective amount.

Dosage values may vary and be adjusted over time according to the individual need and the judgment of the person administering or supervising the administration of the recombinant gp140 antigen, the recombinant gp150 antigen, the recombinant gp160 antigen or the chimaeric HIV antigen polypeptides or compositions of the invention. Dosage ranges set forth herein are exemplary only and do not limit the dosage ranges that may be selected. The amount of active compound(s) in the composition may vary according to factors such as the disease state, age, sex, and weight of the individual. Dosage regimens may be adjusted to provide the optimum therapeutic response. For example, a single dose may be administered, or multiple doses may be administered over time. It may be advantageous to formulate the compositions in dosage unit forms for ease of administration and uniformity of dosage.

The term "preventing", when used in relation to an infectious disease, or other medical disease or condition, is well understood in the art, and includes administration of a composition which reduces the frequency of or delays the onset of symptoms of a condition in a subject relative to a subject which does not receive the composition. Prevention of a disease includes, for example, reducing the number of diagnoses of the infection in a treated population versus an untreated control population, and/or delaying the onset of symptoms of the infection in a treated population versus an untreated control population.

The term "prophylactic or therapeutic" treatment is well known to those of skill in the art and includes administration to a subject of one or more of the compositions of the invention. If the composition is administered prior to clinical manifestation of the unwanted condition (e.g., disease or other unwanted state of the subject) then the treatment is prophylactic, i.e., it protects the host against developing the unwanted condition, whereas if it is administered after manifestation of the unwanted condition, the treatment is therapeutic (i.e., it is intended to diminish, ameliorate, or stabilise the existing unwanted condition or side effects thereof).

Toxicity and therapeutic efficacy of compositions of the invention may be determined by standard pharmaceutical procedures in cell culture or using experimental animals, such as by determining the $LD_{50}$ and the $ED_{50}$. Data obtained from the cell cultures and/or animal studies may be used to formulate a dosage range for use in a subject. The dosage of any composition of the invention lies preferably within a range of circulating concentrations that include the $ED_{50}$ but which has little or no toxicity. The dosage may vary within this range depending upon the dosage form employed and the route of administration utilised. For compositions of the present invention, the therapeutically effective dose may be estimated initially from cell culture assays.

The following examples are offered by way of illustration and not by way of limitation.

Example 1

Antigen Design and Cloning into pEAQ-HT

The coding sequence of the full length gp160 envelope from the HIV-1 subtype C CAP256 SU virus (clone 256.2.06.c7) (SEQ ID NO:1) was provided by Dr Penny Moore (Senior Medical Scientist, Centre for HIV and STIs, National Institute for Communicable Diseases, Johannesburg). The Du151 envelope sequence (SEQ ID NO:2) was retrieved from GenBank (Accession number AF544008.1). Soluble gp140 antigens were designed based on the native flexible linker approach to enable the production of native-like trimers in the absence of furin cleavage (Sharma et al., 2015). The native HIV Env cleavage site was replaced with a 10 amino acid flexible linker comprising of 2 repeats of the Glycine-Serine based (GGGGS) motif. The isoleucine at residue 559 in the N-terminal heptad repeat of gp41 was mutated to a proline and the coding sequence prematurely terminated by the introduction of a stop codon after amino acid residue 664. The gene coding sequences were optimized to reflect the preferred human codon usage and Age1 and Xho1 restriction sites added to the 5' and 3' terminal ends of the genes respectively. Lastly, the native signal sequence was replaced with the murine mAB24 heavy chain-derived LPH signal peptide, to direct translocation of the recombinant protein through the plant secretory pathway (FIG. 1). The genes were synthesized to reflect the optimal human codon usage; the recombinant CAP256 gp140 polypeptide is shown in SEQ ID NO:3 and the recombinant Du151 gp140 polypeptide is shown in SEQ ID NO:8 and then cloned into the pEAQ-HT expression cassette provided by Dr George Lomonossoff (Biological Chemistry Department, John Innes Centre, Norwich, UK). The recombinant plasmids were then transformed into *Agrobacterium tumefaciens* AGL1.

Recombinant CAP256 SU gp120 (SEQ ID NO:5), gp140 fused to HA2 of influenza (SEQ ID NO:4), gp150 (SEQ ID NO:6) and gp160 (SEQ ID NO:7) polypeptides and recombinant Du151 gp120 (SEQ ID NO:10), gp140 fused to HA2 of influenza (SEQ ID NO:9), gp150 (SEQ ID NO:11) and gp160 (SEQ ID NO:12) polypeptides were synthesized in a similar manner.

Example 2

Small Scale Transient Expression in Planta

Cultures of recombinant *A. tumefaciens* AGL1, adjusted to a density of $OD_{600}=1$, were vacuum infiltrated into 4-6 week old *N. benthamiana* plants. The plants were incubated at 22° C., under a regulated 16 hour light/8 hour dark photocycle. Crude total soluble protein was harvested from leaves on alternate days for a 9 day period. Six leaf clippings were harvested from agroinfiltrated leaves (2 leaves per plant, 1 clipping per leaf) and finely ground in liquid nitrogen. The leaf material was resuspended in 300 µl of PBS, supplemented with cOmplete™ EDTA-free protease inhibitor (Roche), and incubated at 4° C. for 1 hour, with shaking. The plant slurries were clarified by centrifugation at 14000 rpm, for 15 minutes, and the supernatant retained at 4° C. Expression of the recombinant proteins was verified by western blotting.

Figure 2:
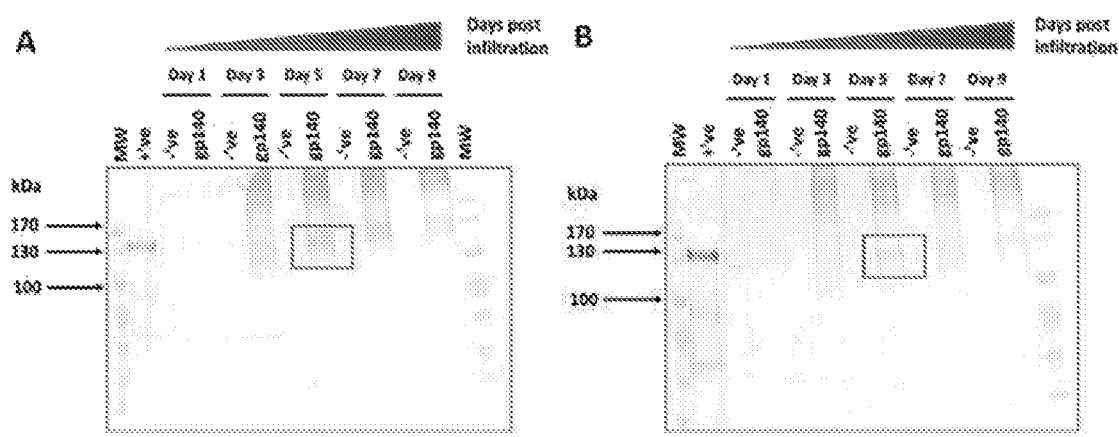
FIG. 2: Western blotting to detect transient expression of recombinant HIV-1 Envelope protein in plants infiltrated with *A. tumefaciens* strains expressing A) CAP256 SU and B) Du151 gp140 NFL. The area highlighted by the block indicates the peak of protein expression 5 days post agroinfiltration.

Low levels of both the CAP256 SU and DU151 gp140 antigens were apparent by 3 days post infiltration and appeared to peak in expression on day 5. In both cases western blotting revealed a faint band in the region of the expected 140 kDa size as well as indistinct bands above the 170 kDa molecular weight marker (FIG. 2). These larger products are presumed to be aggregates that aren't fully resolved by SDS-PAGE.

Example 3

Large Scale Expression and Purification

Recombinant *A. tumefaciens* cultures were scaled up to 2.5 litres enabling the vacuum infiltration of 50-70 plants. The aerial parts of the plants were harvested 5 days post agroinfiltration and homogenized in 2 buffer volumes of PBS, supplemented with cOmplete™ EDTA-free protease inhibitor (Roche). The crude homogenate was incubated for 1 hour, at 4° C., with shaking and then filtered through 4 layers of Miracloth (Merck). The crude plant sap was then clarified by sequential centrifugation steps; twice at 15 344×g for 20 minutes and then again at 17 000×g for 20 minutes.

The supernatant was vacuum filtered through a 0.22 µM Stericup-GP device (Merck Millipore) and applied to a *Galanthuis nivalis* lectin column (Sigma) with a 0.25-0.5 ml/min flow rate. The column was sequentially washed with 100 ml of 0.5M NaCl and then 100 ml of PBS (Lonza). The column was filled with 1M methyl αD-manno-pyranoside (MMP) (Sigma), incubated for 30 minutes and the protein eluted in 40 ml. The elution step was repeated a second time with an elution volume of 20 ml. The eluted protein was buffer exchanged into PBS and concentrated using a Vivaspin Protein Concentrator with a 30 kDa cut off (GE Healthcare).

Figure 3:
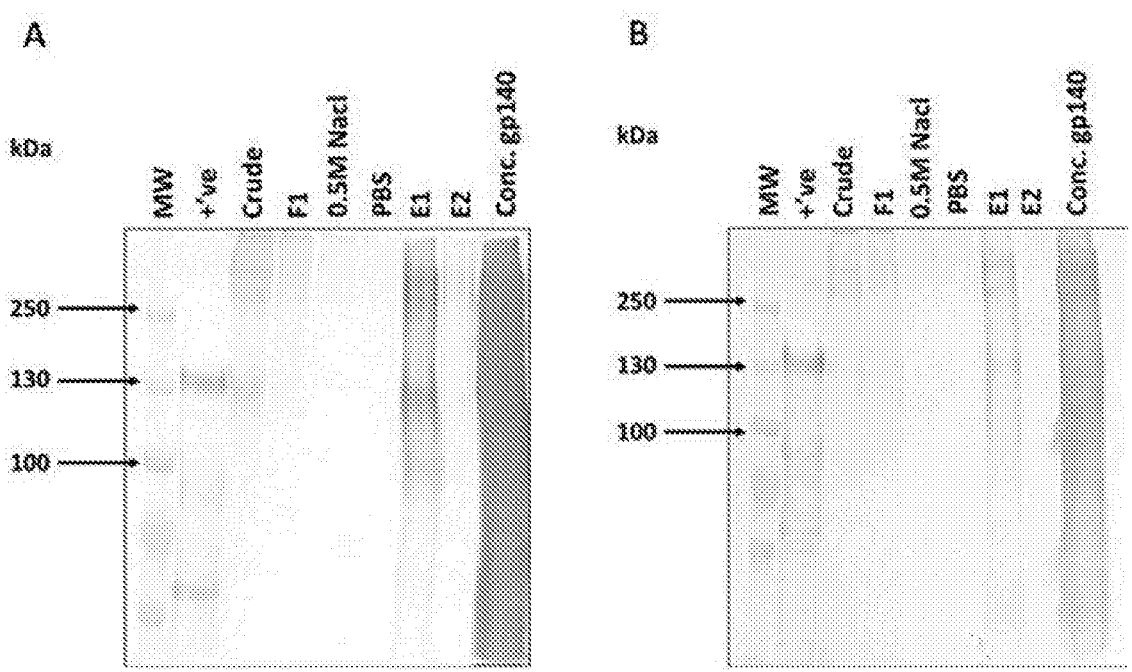
FIG. 3: Western blotting of flow through fractions sampled during purification of A) CAP256 and B) DU151 gp140 NFL antigens. (+'ve=100 ng HIV-1 CN54 gp120 Envelope, crude=crude homogenate, F1=flow through of homogenate, 0.5M NaCl and PBS were used to wash the resin, E1 and E2=eluate 1 and 2 respectively, conc. gp140=concentrated gp140 NFL protein)

Western blotting using polyclonal anti-gp120 antibody was performed on samples taken from the column flow-through during the purification process. Low levels of expression were evident in the crude protein extract which bound efficiently to the resin. Low levels of protein were detected in the flow through with minimal loss of the antigens observed in the 2 wash steps. The protein was efficiently eluted (mostly during the first elution) and then concentrated. The smear observed for the concentrated protein is due to overloading (FIG. 3A and FIG. 3B).

Figure 4:
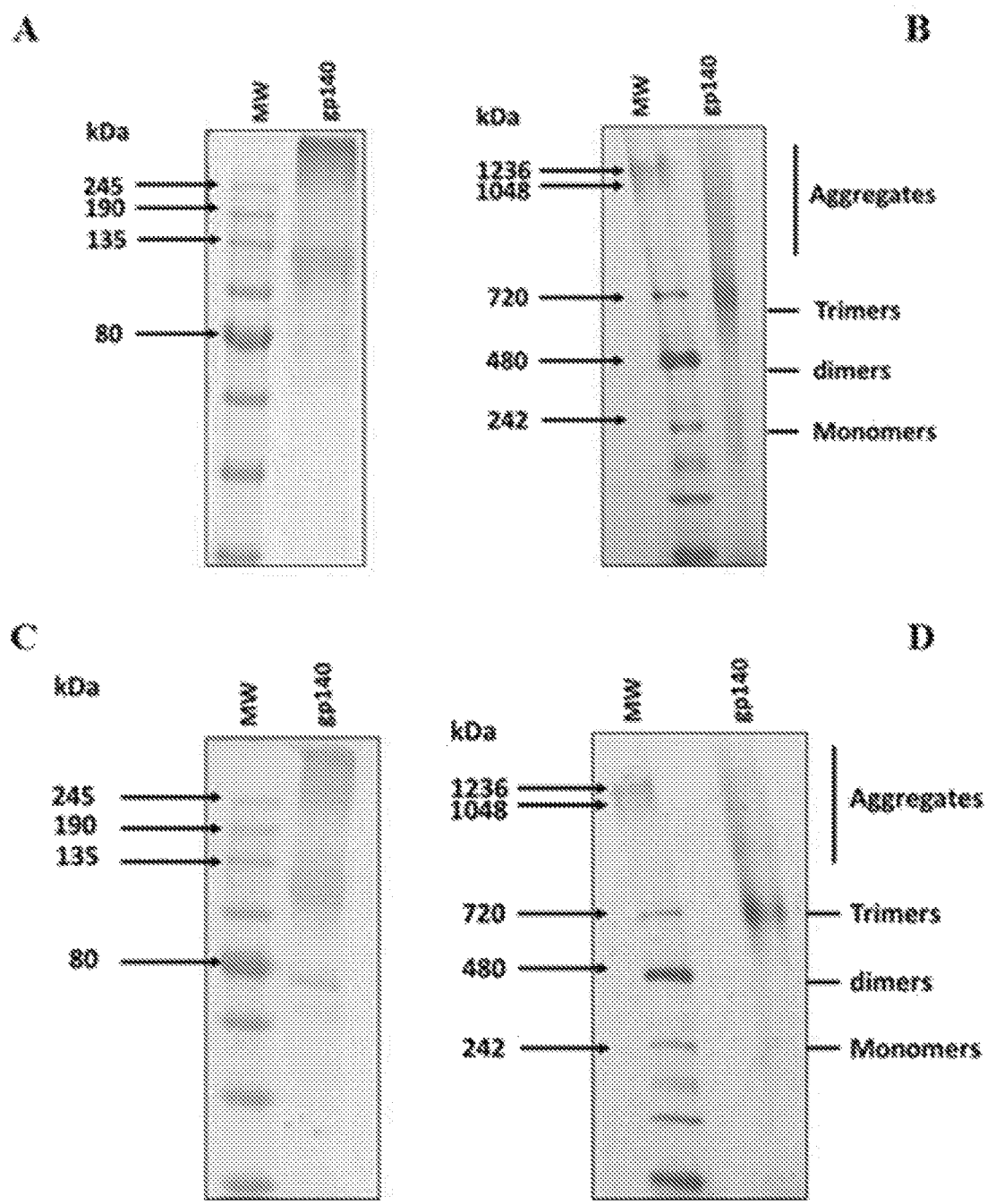
FIG. 4: Coomassie blue staining of purified CAP256 SU and Du151 gp140 NFL antigens after resolution on SDS-PAGE and BN-PAGE gels. (A) and (B) show CAP256 SU gp140 NFL resolved by SDS-PAGE and BN-PAGE respectively whereas (C) and (D) show DU151 gp140 NFL resolved by SDS-PAGE and BN-PAGE respectively. The expected sizes of aggregates, trimers, dimers and monomers are indicated alongside the BN-PAGE gels in (B) and (D).

Coomassie brilliant blue staining was performed on standard SDS-PAGE gels as well as BN-PAGE gels which enable the resolution of proteins under native conditions. Coomassie staining of SDS-PAGE gels for both CAP256 SU and Du151 gp140 NFL yielded distinct bands just below the 135 kDA and above the 245 kDa molecular weight markers (FIG. 4A and FIG. 4C). The identities of both bands were independently verified as HIV Envelope, by the CPGR, using LCMS. Low levels of contamination with endogenous plant proteins were evident just below the 80 kDa marker. BN-PAGE revealed that the predominant product was trimeric for both CAP256 SU and Du151 gp140 NFL antigens (FIG. 4B and FIG. 4D). Both aggregates and monomers were also present.

Example 4

Characterization with Prototype Broadly Neutralizing Monoclonal Antibodies

The ability of the plant-produced antigens to reproduce the structure of the native glycoprotein was determined by evaluating the reactivity of prototype monoclonal antibodies with the purified proteins in an indirect binding ELISA assay. The reactivity of each monoclonal antibody was also compared to the equivalent protein produced in mammalian cell culture as part of an independent study. These proteins were purified by *Galanthus nivalis* lectin affinity chromatography from transfected HEK293 cells.

TABLE 1

Summary of prototype monoclonal antibodies used to interrogate the structure of plant-produced gp140 NFL antigens.

| Region | Antibody | Epitope | Reference |
|---|---|---|---|
| V1/V2-glycan | PG9 | trimer specific, | (Walker et al., 2009) |
| | PG16 | dependant on glycan | (Walker et al., 2009) |
| | PGT145 | N160 | (Walker et al., 2011) |
| V3-glycan | PGT 135 | Dependant on glycan N332 | (Walker et al., 2011) (Kong et al., 2013) |
| OD-glycan* | PGT128 | Dependant on glycan N332 | (Walker et al., 2011) (Pejchal et al., 2011) |
| CD4bs | VRC01 | Initial site of CD4 binding | (Wu et al., 2010; Zhou et al., 2010) |

*OD = outer domain

A 96-well Maxisorb® microtitre plate (NunC) was coated overnight, at 4° C., with 100 µl of 1 µg/ml purified HIV gp140 protein. The plate was washed 3 times with 200 µl of PBS and blocked for 1 hour, at room temperature, with 200 µl 5% skim milk powder (Oxoid) in PBS. Plates were washed 5 times with PBS containing 0.1% TWEEN® 20 (Sigma) and incubated for 2 hours with human monoclonal antibodies, serially-diluted in 2.5% Skim milk powder in PBS. The wash step was repeated, as before, and the plates incubated with 1:5000 dilution of polyclonal rabbit anti-human IgG/HRP (Dako), for 1 hour. The wash step was repeated and the plates developed by adding 100 µl TMB ELISA substrate (high sensitivity) (Abcam®). The reaction was terminated after 10 minutes by the addition of 100 µl 1N $H_2SO_4$ and the signal read at 450 nm. All samples were run in triplicate alongside a negative control whereby primary antibody was omitted. A positive control was included comprising of goat anti-HIV-1 gp120 primary antibody (AbD Serotec) which was detected with 1:5000 polyclonal rabbit anti-goat Immunoglobulins HRP (Dako). The data was plotted as a 4 point linear regression using GraphPad Prism 5.

Figure 5:
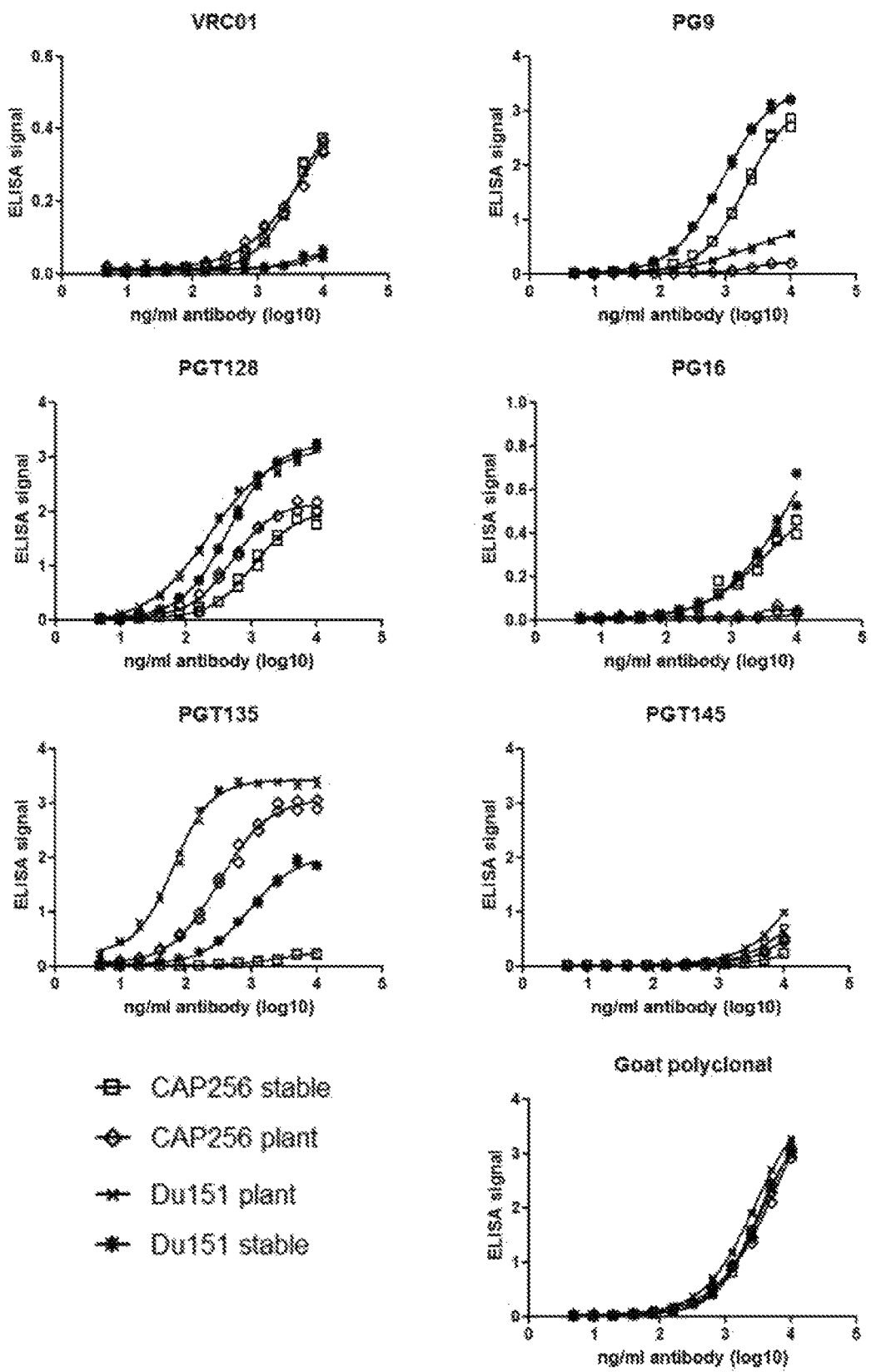
FIG. 5: Binding ELISA to assess the reactivity of prototype monoclonal antibodies with plant-produced CAP256 SU and Du151 gp140 NFL. Equivalent antigens produced in stable HEK293 cell lines were included as controls (CAP256 stable and Du151 stable).

A similar trend was seen for the binding of most antibodies to both plant-produced and mammalian-derived antigens (FIG. 5). The CAP256 SU gp140 NFL antigen exhibited higher levels of binding to VRC01 than Du151 which has a partial escape mutation in the core epitope. The N332-dependent antibodies, PGT128 and PGT135, both exhibited higher reactivity with the plant produced antigens. Similar reactivity was observed for the trimer preferring antibodies which distinguish well-ordered glycoproteins from misfolded envelope. Low levels of binding were evident for plant-produced antigens with PG9. Neither plant-produced antigen displayed any reactivity with PG16. No obvious differences were seen for the binding of the polyclonal antibody confirming that the protein levels on the ELISA plates were comparable. In conclusion the data confirms that plants can reproduce quaternary structure dependant epitopes, including those that depend on glycans. The data also shows a proportion of the purified protein comprises of well-ordered trimers and that this is comparable to mammalian cell-derived protein. Lastly, plant-produced antigens may reproduce high-mannose dependent epitopes found in native Env in humans better than mammalian cells such as CHO lines.

Example 5

Refined Recovery of Trimeric HIV Env gp140 Trimers

Figure 6:
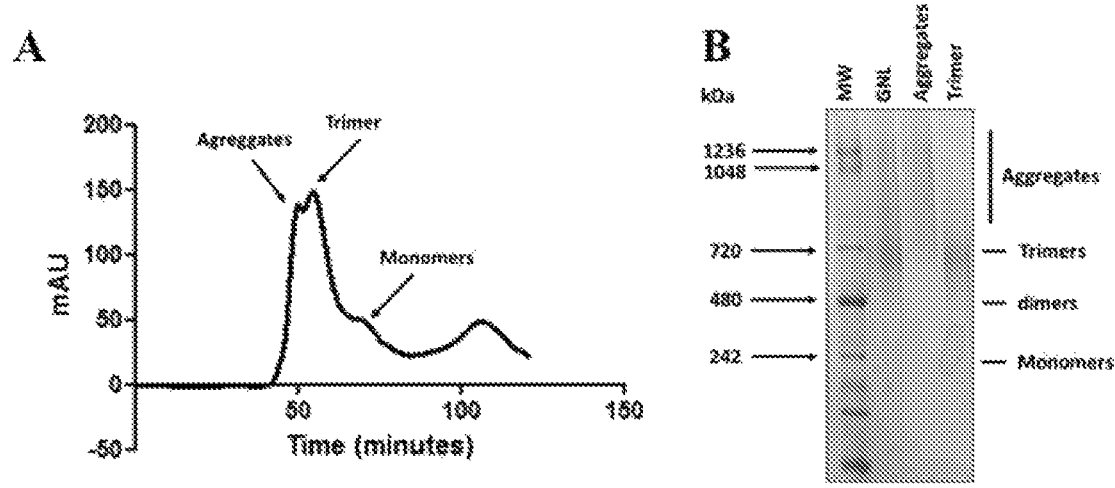
FIG. 6: Purification of recombinant CAP256 SU gp140 NFL trimers. (A) Superdex 200 Hiload 16/600 elution profile of fractionated Env species recovered by affinity chromatography. The identity of the different protein species is indicated. (B) Coomassie stained BN-PAGE confirming the recovery of trimeric protein and the removal of contaminating, non-trimeric Env aggregates. The affinity purified protein (GNL) that was resolved by SEC was run alongside aggregate and trimer samples for comparison.

Following elution from the GNL affinity resin, the recombinant protein was concentrated and buffer exchanged into 5 ml PBS (Lonza). The purified protein was then fractionated on the basis of size using a Superdex 200 HiLoad 16/600 column (GE Healthcare). Fractions corresponding to the trimeric protein were pooled and when necessary concentrated further using a Vivaspin Protein Concentrator with a 30 kDa cut off (GE Healthcare). The elution profile confirmed the successful separation of the different Env species enabling the recovery of trimeric protein from contaminating aggregates, monomers and endogenous plant protein. Coomassie staining of BN-PAGE gels confirmed the removal of contaminating aggregates from the affinity purified protein to yield purified trimers (FIG. 6).

Example 6

Immunization of Rabbits with Affinity Purified Gp140 NFL Antigens

Rabbit immunizations and blood sampling was conducted at the University of Cape Town, in accordance with the guidelines and approval of the appropriate ethics committee (AEC 014-30). Three month old New Zealand white rabbits were immunized with 50 μg of recombinant protein suspended in Alhydrogel® Adjuvant 2% (Invivogen) at a concentration of 1:1 (antigen:adjuvant). Groups of 5 rabbits were immunized intramuscularly into the quadriceps muscle of the hind leg. Animals were immunized at weeks 0, 4, 12 and 20 and blood was drawn at 0, 4, 8, 12, 16, 20 and 24 weeks for analysis.

Figure 7:
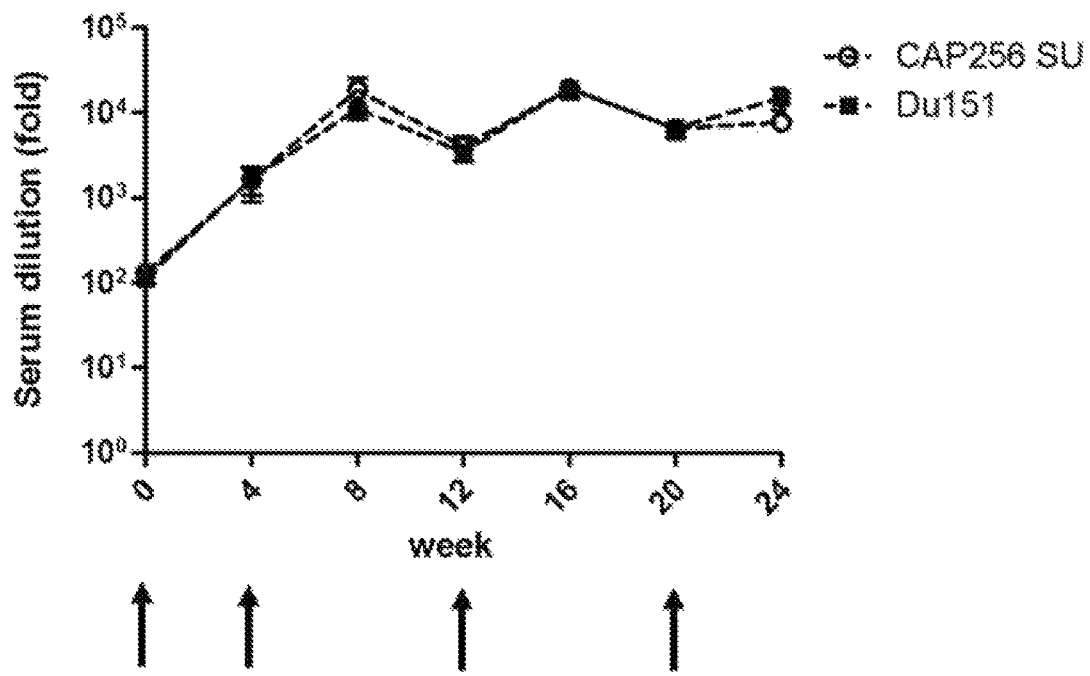
FIG. 7: Binding antibody titres elicited over the course of the immunization regimen. The levels of binding antibodies are indicated as the fold dilution required to generate an end point titre based on 2*geometric mean of week 0 dilution range. The error bars at each time point are indicated in black and the timing of each immunization indicated by a red arrow below the graph.

The levels of binding antibodies in the sera of immunized animals were determined by indirect binding ELISA with minor alterations to the protocol previously described. Briefly, 96-well Maxisorb® microtitre plates (NunC) were coated overnight with 10 ng of recombinant CAP256 SU or Du151 gp140 NFL proteins produced in mammalian cells. The primary antibody dilution was incubated on the plate overnight. There were no other deviations from the original protocol. All immunized rabbits developed detectable binding antibodies after a single immunization and peak binding antibody titres were observed after 3 inoculations (FIG. 7). Immunized animals also developed neutralizing antibodies against several tier 1 viral isolates (Table 2).

TABLE 2

Longitudinal neutralizing antibodies induced by the CAP256 SU and Du151 gp140 NFL antigens. Animals were immunized at weeks 0, 4, 12 and 20. Sera from immunized animals were assessed for neutralizing activity against a panel of Env-pseudotyped virions over the course of the experiment. Neutralization of each virus is represented as the serum dilution required for a 50% reduction in entry of the infecting virus into a reporter cell line ($ID_{50}$).

| | | Tier 1A | | | | | | Tier 1B | | |
| --- | --- | --- | --- | --- | --- | --- | --- | --- | --- | --- |
| | | MW965.26 | | | MN.3 | | | 6644 | | |
| Vaccine | Rabbit ID | WK 8 | WK 16 | WK 24 | WK 8 | WK 16 | WK 24 | WK 8 | WK 16 | WK 24 |
| CAP256 SU gp140 NFL | RB #2755 | 195 | 124 | 30 | <20 | <20 | <20 | <20 | <20 | <20 |
| | RB #2756 | 109 | 540 | 94 | <20 | <20 | <20 | <20 | <20 | <20 |
| | RB #2758 | <20 | 102 | 81 | <20 | 151 | 144 | <20 | <20 | <20 |
| | RB #2760 | 473 | 305 | 297 | 107 | <20 | <20 | 166 | 77 | 28 |
| | RB #2764 | 903 | 457 | 510 | 73 | 22 | <20 | <20 | 39 | <20 |
| Du151 gp140 NFL | RB #2757 | <20 | <20 | <20 | <20 | <20 | <20 | <20 | <20 | <20 |
| | RB #2759 | 105 | 319 | 420 | <20 | <20 | <20 | <20 | 21 | 22 |
| | RB #2761 | 268 | 308 | 325 | <20 | <20 | <20 | <20 | 21 | <20 |
| | RB #2762 | 39 | 167 | 198 | <20 | <20 | <20 | <20 | <20 | <20 |
| | RB #2763 | 29 | 153 | 552 | <20 | <20 | <20 | <20 | 21 | 25 |

(WK = week)

Example 7

Immunization of Rabbits with Size Exclusion Chromatography Purified Gp140 NFL Antigens Immunogenicity studies were conducted using New Zealand White rabbits at the Animal Unit of the University of Stellenbosch in accordance with the guidelines and approval of the UCT Animal Ethics Committee (AEC 014-30). Rabbits were immunized with 50 μg of purified trimer, formulated in Alhydrogel® Adjuvant 2% (Invivogen) at a concentration of 1:1 v:v (antigen:adjuvant).

Figure 8:
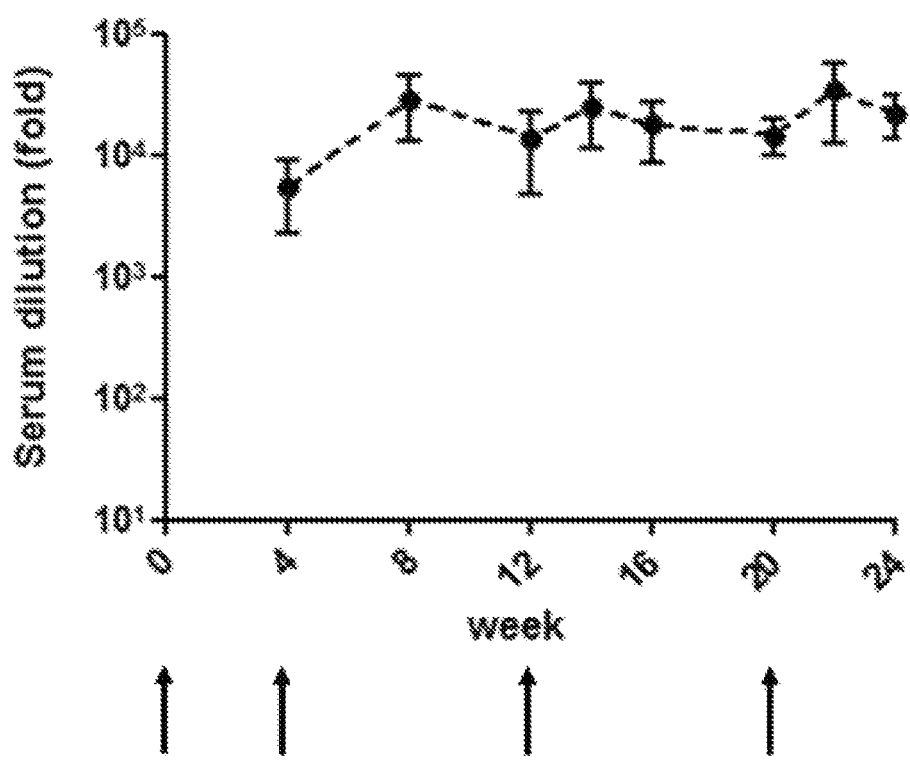
FIG. 8: Serum trimer-binding antibodies elicited by the purified CAP256 SU gp140 NFL trimer in rabbits. Binding antibody levels were determined as a fold-dilution derived from the fitted 4 point linear regression curve using a threshold of the minimum+standard error of the minimum for each time point. The timing of each immunization is indicated by an arrow below the X axis. Error bars at each time point are indicated in black.
Figure 9:
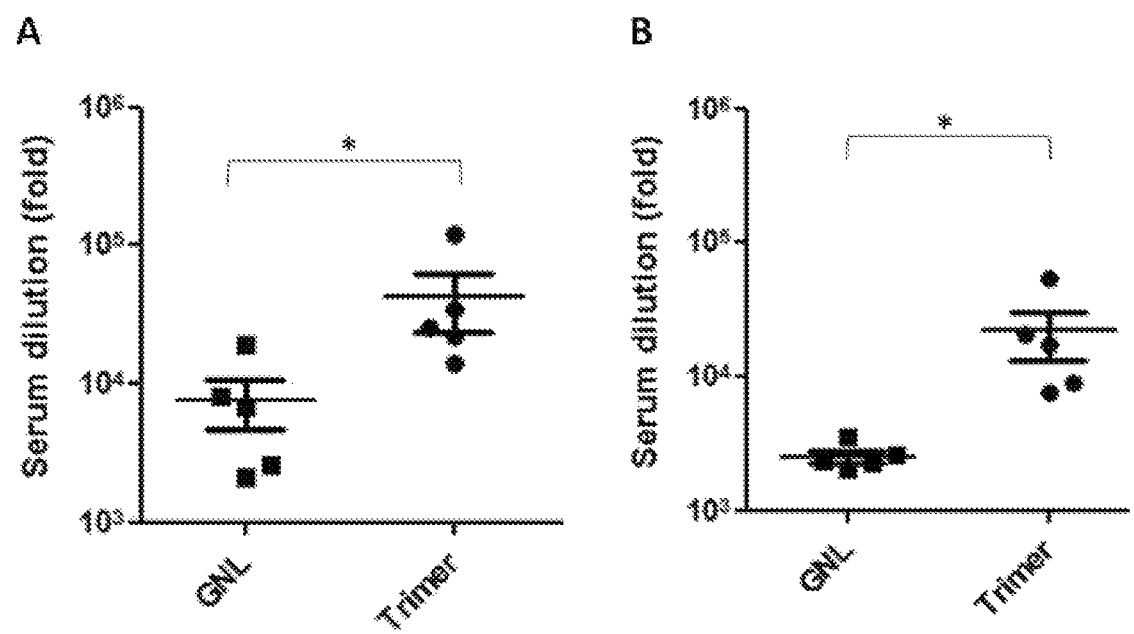
FIG. 9: Comparison of serum trimer-binding antibody titres elicited by the SEC-purified trimer and the same antigen purified by affinity-chromatography (GNL). Trimer binding antibodies elicited in this experiment were compared with the antibodies elicited in the study described in the companion article after the A) $3^{rd}$ and B) $4^{th}$ immunization. Statistical comparisons between groups were made using the Mann-Whitney two-tailed unpaired test (*P<0.05).

The animals were immunized intramuscularly in the quadriceps muscle of the hind leg at weeks 0, 4, 12 and 20. Blood was drawn at weeks 0, 4, 8, 12, 14, 16, 20, 22 and 24 weeks for analysis. The experiment was terminated after 24 weeks. Serum-binding antibodies were quantified as before using the equivalent protein produced in mammalian cells, purified to size homogeneity by SEC. This enabled quantification of antibodies that specifically recognized the trimeric glycoprotein, a more authentic representation of the protein than monomers or aggregates. All immunized animals developed robust trimer-binding antibodies (FIG. 8) and improved neutralizing antibodies (Table 3). Comparison of the trimer-binding antibody titres confirmed that the SEC-purified trimer was more immunogenic than the affinity purified trimer that was previously used (FIG. 9).

TABLE 3

Serum $ID_{50}$ neutralizing antibody titres induced by the CAP256 SU gp140 NFL trimer. Animals were immunized with 50 μg of trimeric protein at weeks 0, 4 and 12 and 20. Sera from immunized animals were assessed for neutralizing activity against a standard panel of Env-pseudotyped virions over the course of the experiment. Neutralization of each pseudovirus is presented as the serum dilution required for a 50% reduction in entry of the infecting virus into a reporter cell line ($ID_{50}$).

| | | Tier 1A | | | | | | | | Tier 1B | | | | | | | |
|---|---|---|---|---|---|---|---|---|---|---|---|---|---|---|---|---|---|
| | | MW965.26 | | | | MN.3 | | | | 6644 | | | | 1107356 | | | |
| Vaccine | Animal ID | WK 0 | WK 8 | WK 14 | WK 22 | WK 0 | WK 8 | WK 14 | WK 22 | WK 0 | WK 8 | WK 14 | WK 22 | WK 0 | WK 8 | WK 14 | WK 22 |
| Trimer | RB#1 | <20 | 2137 | 567 | 332 | <20 | 22 | <20 | <20 | <20 | <20 | 29 | 41 | <20 | 26 | <20 | <20 |
| | RB#2 | <20 | 558 | 796 | 473 | <20 | <20 | <20 | <20 | <20 | <20 | 39 | 69 | <20 | <20 | <20 | <20 |
| | RB#3 | <20 | 2481 | 11520 | 1055 | <20 | <20 | <20 | <20 | <20 | 150 | 1052 | 99 | <20 | 27 | 90 | 23 |
| | RB#4 | <20 | 176 | 378 | 750 | <20 | <20 | <20 | <20 | <20 | <20 | 30 | 45 | <20 | <20 | <20 | <20 |
| | RB#5 | <20 | 214 | 2462 | 709 | <20 | 26 | 54 | 45 | <20 | <20 | 57 | 62 | <20 | <20 | <20 | <20 |

(WK = week)

REFERENCES

Rybicki, E. P., (2010) Plant-made Vaccines for Humans and Animals. Plant Biotechnol J 8, 620-637.

Kessans, S. A. et al., (2016) Immunological Characterization of Plant-Based HIV-1 Gag/Dgp41 Virus-Like Particles. PLoS One 11, e0151842.

Rosenberg, Y. et al., (2013) Rapid high-level production of functional HIV broadly neutralizing monoclonal antibodies in transient plant expression systems. PLoS One 8, e58724.

Ringe, R. P. et al., (2013) Cleavage strongly influences whether soluble HIV-1 envelope glycoprotein trimers adopt a native-like conformation. Proc Natl Acad Sci USA 110, 18256-18261.

Sharma, S. K. et al., (2015) Cleavage-independent HIV-1 Env trimers engineered as soluble native spike mimetics for vaccine design. Cell Rep 11, 539-550.

The invention claimed is:

1. A method for producing a recombinant polypeptide capable of forming a trimeric Env glycoprotein complex, the method comprising the steps of:
   (i) providing a codon-optimised nucleotide sequence encoding a recombinant polypeptide having the formula:

$X_1—X_2—X_3—X_4$ wherein,
   $X_1$ is a secretory signal peptide;
   $X_2$ is a HIV gp120 envelope polypeptide comprising an amino acid sequence as set forth in SEQ ID NO. 5 or SEQ ID NO. 10;
   $X_3$ is a linker peptide; and
   $X_4$ is a HIV gp41 polypeptide,
   wherein the gp41 polypeptide is selected from either a full-length gp41 polypeptide or a truncated gp41 polypeptide, and wherein if the gp41 polypeptide is a truncated gp41 polypeptide then it is truncated after the LALD motif of the gp41 polypeptide;
   further wherein the recombinant polypeptide comprises an I559P mutation;
   (ii) cloning the codon-optimised nucleic acid encoding the recombinant polypeptide into an expression vector adapted to express the recombinant polypeptide in a plant cell;
   (iii) transforming the plant cell with the expression vector of step (ii);
   (iv) expressing the recombinant polypeptide in the plant cell; and
   (v) recovering the recombinant polypeptide from the plant cell.

2. The method of claim 1, wherein the secretory signal peptide is LPH.

3. The method of claim 1, wherein the linker peptide is a flexible linker comprising the amino acid sequence GGGGSGGGGS.

4. The method of claim 1, wherein the plant cell is a *Nicotiana benthamiana* cell.

5. A recombinant polypeptide capable of forming a trimeric Env glycoprotein complex, the recombinant polypeptide comprising the formula:

$X_1—X_2—X_3—X_4$ wherein,
$X_2$ is a secretory signal peptide;
$X_2$ is a HIV gp120 envelope polypeptide comprising an amino acid sequence as set forth in SEQ ID NO. 5 or SEQ ID NO. 10;
$X_3$ is a linker peptide; and
$X_4$ is a HIV gp41 polypeptide,
wherein the gp41 polypeptide is selected from either a full-length gp41 polypeptide or a truncated gp41 polypeptide, and wherein if the gp41 polypeptide is a truncated gp41 polypeptide then it is truncated after the LALD motif of the gp41 polypeptide;
further wherein the recombinant polypeptide comprises an I559P mutation.

6. A trimeric Env glycoprotein complex, comprising three recombinant polypeptides of claim 5.

7. A nucleic acid encoding the recombinant polypeptide of claim 5.

8. An expression vector comprising the nucleic acid of claim 7.

9. A pharmaceutical composition comprising the recombinant polypeptide of claim 5.

10. The pharmaceutical composition of claim 9, further comprising a pharmaceutically acceptable carrier or adjuvant.

11. The recombinant polypeptide of claim 5 for use in a method of eliciting an immune response against HIV in a subject, the method comprising administering an effective amount of the polypeptide or trimeric Env glycoprotein complex to the subject.

12. The recombinant polypeptide for use, the trimeric Env glycoprotein complex for use or the pharmaceutical composition for use of claim 11, wherein the subject is a human.

13. Use of the recombinant polypeptide of claim 5 for the preparation of a medicament.

14. A method of eliciting an immune response against HIV in a subject, the method comprising administering an effective amount of the recombinant polypeptide of claim 5 to the subject.

15. The method of claim 14, wherein the subject is a human.

16. A pharmaceutical composition comprising the trimeric Env glycoprotein complex of claim 6.

17. The trimeric Env glycoprotein complex of claim 6 for use in a method of eliciting an immune response against HIV in a subject, the method comprising administering an effective amount of the polypeptide or trimeric Env glycoprotein complex to the subject.

18. The pharmaceutical composition of claim 9 for use in a method of eliciting an immune response against HIV in a subject, the method comprising administering an effective amount of the polypeptide or trimeric Env glycoprotein complex to the subject.

19. Use of a trimeric Env glycoprotein complex of claim 6 for the preparation of a medicament.

20. A method of eliciting an immune response against HIV in a subject, the method comprising administering an effective amount of the trimeric Env glycoprotein complex of claim 6 to the subject.

* * * * *